US011041008B2

(12) United States Patent
Bergamaschi et al.

(10) Patent No.: US 11,041,008 B2
(45) Date of Patent: *Jun. 22, 2021

(54) HETERODIMERS OF IL-15 AND IL-15R ALPHA TO INCREASE THYMIC OUTPUT AND TO TREAT LYMPHOPENIA

(71) Applicant: the Government of the United States of America as Represented by the Secretary of the Department of Health and Human Services, Rockville, MD (US)

(72) Inventors: Cristina Bergamaschi, Frederick, MD (US); Barbara K. Felber, Rockville, MD (US); George N. Pavlakis, Rockville, MD (US); Antonio Valentin, Frederick, MD (US)

(73) Assignee: The Government of the United States of America as Represented by The Secretary of the Department of Health and Human Services, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/123,431

(22) Filed: Sep. 6, 2018

(65) Prior Publication Data

US 2019/0048056 A1    Feb. 14, 2019

Related U.S. Application Data

(60) Division of application No. 15/485,093, filed on Apr. 11, 2017, now Pat. No. 10,093,710, which is a continuation of application No. 14/512,913, filed on Oct. 13, 2014, now Pat. No. 9,975,937, which is a continuation of application No. 13/390,504, filed as application No. PCT/US2010/045511 on Aug. 13, 2010, now Pat. No. 8,871,191.

(60) Provisional application No. 61/234,152, filed on Aug. 14, 2009, provisional application No. 61/234,155, filed on Aug. 14, 2009.

(51) Int. Cl.
| | |
|---|---|
| C07K 14/54 | (2006.01) |
| C07K 14/715 | (2006.01) |
| C12N 15/62 | (2006.01) |
| C12P 19/30 | (2006.01) |
| C12N 5/16 | (2006.01) |
| A61K 38/17 | (2006.01) |
| A61K 45/06 | (2006.01) |
| A61K 48/00 | (2006.01) |
| A61K 47/68 | (2017.01) |
| A61K 38/20 | (2006.01) |
| C12N 15/09 | (2006.01) |
| A61K 38/14 | (2006.01) |
| A61K 38/00 | (2006.01) |
| C12N 5/07 | (2010.01) |
| C12N 15/113 | (2010.01) |
| C12P 21/02 | (2006.01) |

(52) U.S. Cl.
CPC ...... *C07K 14/5443* (2013.01); *A61K 38/1793* (2013.01); *A61K 38/2086* (2013.01); *A61K 45/06* (2013.01); *A61K 47/6813* (2017.08); *A61K 47/6835* (2017.08); *A61K 48/005* (2013.01); *C07K 14/54* (2013.01); *C07K 14/7155* (2013.01); *C12N 5/163* (2013.01); *C12N 15/09* (2013.01); *C12N 15/62* (2013.01); *C12P 19/30* (2013.01); *A61K 38/00* (2013.01); *C07K 2319/30* (2013.01); *C07K 2319/33* (2013.01); *C07K 2319/70* (2013.01); *C12N 5/06* (2013.01); *C12N 15/1138* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 5,552,303 A | 9/1996 | Grabstein et al. | |
| 5,574,138 A | 11/1996 | Grabstein et al. | |
| 6,001,973 A | 12/1999 | Strom et al. | |
| 6,063,911 A | 5/2000 | Vournakis et al. | |
| 6,451,308 B1 | 9/2002 | Strom et al. | |
| 6,548,065 B1 | 4/2003 | Anderson et al. | |
| 6,764,836 B2 | 7/2004 | Anderson et al. | |
| 6,787,132 B1 | 9/2004 | Gabizon et al. | |
| 6,864,245 B2 | 3/2005 | Helton et al. | |
| 6,998,476 B2 | 2/2006 | Strom et al. | |
| 7,067,132 B2 | 6/2006 | Grabstein et al. | |
| 7,112,436 B1 | 9/2006 | Rose-John et al. | |
| 7,258,853 B2 | 8/2007 | Strom et al. | |
| 7,435,596 B2 | 10/2008 | Imai et al. | |
| 7,638,604 B2 | 12/2009 | Li et al. | |
| 8,124,084 B2 | 2/2012 | Stoklasek et al. | |
| 8,163,879 B2 | 4/2012 | Wong et al. | |
| 8,224,578 B2 | 7/2012 | Raab et al. | |
| 8,871,191 B2* | 10/2014 | Pavlakis | A61K 48/005 424/85.2 |
| 9,975,937 B2* | 5/2018 | Pavlakis | A61K 48/005 |

(Continued)

FOREIGN PATENT DOCUMENTS

| | | |
|---|---|---|
| EP | 1777294 | 4/2007 |
| WO | 1995027722 | 10/1995 |

(Continued)

OTHER PUBLICATIONS

Doerks et al., 1998, Trends in Genetics 14:248-250.*

(Continued)

*Primary Examiner* — Bridget E Bunner
*Assistant Examiner* — Fozia Hamud
(74) *Attorney, Agent, or Firm* — Yichen Liu

(57) ABSTRACT

The present invention provides method for promoting the maturation and export of T cells from thymic tissue by contacting the thymic tissue with supraphysiological levels of interleukin (IL)-15. The present invention also provides methods for preventing, alleviating, reducing, and/or inhibiting lymphopenia or peripheral depletion of lymphocytes in a patient in need thereof by administering to the patient IL-15.

12 Claims, 23 Drawing Sheets

Specification includes a Sequence Listing.

(56) References Cited

U.S. PATENT DOCUMENTS

| | | |
|---|---|---|
| 2002/0022030 A1 | 2/2002 | Marrack et al. |
| 2002/0114781 A1 | 8/2002 | Strom et al. |
| 2002/0127201 A1 | 9/2002 | Boussiotis et al. |
| 2002/0128436 A1 | 9/2002 | Strom et al. |
| 2002/0182178 A1 | 12/2002 | Grooten et al. |
| 2003/0105295 A1 | 6/2003 | Strom et al. |
| 2003/0236255 A1 | 12/2003 | Waer et al. |
| 2004/0087015 A1 | 5/2004 | Vournakis et al. |
| 2004/0170604 A1 | 9/2004 | Ekida et al. |
| 2004/0253587 A1 | 12/2004 | Grabstein et al. |
| 2005/0032167 A1 | 2/2005 | Anderson et al. |
| 2005/0042220 A1 | 2/2005 | Li et al. |
| 2005/0202005 A1 | 9/2005 | Winchester et al. |
| 2006/0057102 A1 | 3/2006 | Zheng et al. |
| 2006/0057680 A1 | 3/2006 | Zheng et al. |
| 2006/0093605 A1 | 5/2006 | Campana et al. |
| 2006/0104945 A1 | 5/2006 | Choi et al. |
| 2006/0147419 A1 | 7/2006 | Perera et al. |
| 2006/0165668 A1 | 7/2006 | Liu et al. |
| 2006/0257361 A1 | 11/2006 | Watanabe et al. |
| 2006/0263857 A1 | 11/2006 | Lefrancois et al. |
| 2007/0110714 A1 | 5/2007 | Hayashi et al. |
| 2007/0134718 A1 | 6/2007 | Grooten et al. |
| 2007/0141557 A1 | 6/2007 | Raab et al. |
| 2007/0160578 A1 | 7/2007 | Waldmann et al. |
| 2008/0255039 A1 | 10/2008 | Bernard et al. |
| 2009/0017000 A1 | 1/2009 | Cai et al. |
| 2009/0082299 A1 | 3/2009 | Felber et al. |
| 2009/0238791 A1 | 9/2009 | Jacques et al. |
| 2011/0081311 A1 | 4/2011 | Pavlakis et al. |
| 2012/0230946 A1 | 9/2012 | Wong et al. |

FOREIGN PATENT DOCUMENTS

| | | |
|---|---|---|
| WO | 9530695 | 11/1995 |
| WO | 9637223 | 11/1996 |
| WO | 9741232 | 11/1997 |
| WO | 9836768 | 8/1998 |
| WO | 0002582 | 1/2000 |
| WO | 0036918 | 6/2000 |
| WO | 0062805 | 10/2000 |
| WO | 0180889 | 11/2001 |
| WO | 0222805 | 3/2002 |
| WO | 2004059556 | 7/2004 |
| WO | 2005085282 | 9/2005 |
| WO | 2006020849 | 2/2006 |
| WO | 2007001677 | 1/2007 |
| WO | 2007046006 | 4/2007 |
| WO | 2007084342 | 7/2007 |
| WO | 2007095643 | 8/2007 |
| WO | 2008089144 | 7/2008 |
| WO | 2009002562 | 12/2008 |

OTHER PUBLICATIONS

Chapoval et al, Journal of Immunology, 1998; vol. 161, pp. 6977-6984.*

EMBL Database accession No. BC074726, Homo sapiens interleukin 15 receptor, alpha, transcript variant 1, m RNA (cDNA clone MGC:103798 IMAGE: 30915179), complete cds, dated Aug. 4, 2004.

U.S. Appl. No. 11/435,497, Examiner Interview Summary Record, dated Jun. 27, 2011, 4 pages.

U.S. Appl. No. 11/435,497, Final Office Action, dated Jan. 13, 2011, 10 pages.

U.S. Appl. No. 11/435,497, Final Office Action, dated Oct. 30, 2009, 13 pages.

U.S. Appl. No. 11/435,497, Non-Final Office Action, dated Jun. 7, 2010, 11 pages.

U.S. Appl. No. 11/435,497, Non-Final Office Action, dated Feb. 25, 2009, 16 pages.

U.S. Appl. No. 11/435,497, Notice of Allowance, dated Oct. 19, 2011, 7 pages.

U.S. Appl. No. 11/435,497, Restriction Requirement, dated Jun. 27, 2008, 7 pages.

European Patent Application No. 11154217.1, Extended European Search Report, dated Nov. 14, 2011, 13 pages.

U.S. Appl. No. 13/390,504 , Final Office Action, dated Oct. 7, 2013, 22 pages.

U.S. Appl. No. 13/390,504, Notice of Allowance, dated Jun. 25, 2014, 9 pages.

U.S. Appl. No. 13/390,504, Office Action, dated Jan. 2, 2013, 20 pages.

U.S. Appl. No. 14/512,913, Final Office Action, dated Dec. 15, 2016, 8 pages.

U.S. Appl. No. 14/512,913, Non-Final Office Action, dated May 3, 2016, 8 pages.

U.S. Appl. No. 14/512,913, Restriction Requirement, dated Jul. 13, 2015, 8 pages.

Alpdogan , "IL-7 and IL-15: therapeutic cytokines for Immunodeficiency", Trends Immunol, vol. 26(1), 2005, pp. 56-64.

Alpdogan et al., "Interleukin-15 enhances immune reconstitution after allogeneic bone marrow transplantation", Blood, vol. 15,271922, Jan. 15, 2001, pp. 865-873.

Altman et al., "Phenotypic analysis of antigen-specific T lymphocytes", Science, vol. 274(5284), 1996, pp. 94-96.

Anderson et al., "Functional Characterization of the Human Interleukin-15 Receptor a Chain and Close Linkage of IL15RA and IL2RA Genes (*)", The Journal of Biological Chemistry, vol. 270, No. 50, Dec. 15, 1995, pp. 29862-29869.

Armitage et al., "IL-15 has stimulatory activity for the induction of B cell proliferation and differentiation", J. Immunol, vol. 154(2), Jan. 15, 1995, pp. 483-490.

Ausubel et al., "Current Protocols in Molecular Biology", John Wiley & Sons, 1993, pp. 2.10.1-2.10.16.

Baccala , "Tumor immunity via homeostatic T cell proliferation: mechanistic aspects and clinical perspectives", Springer Semin Immunopathol published online. vol. 27(1), 2005, pp. 75-85.

Badoual et al., "The soluble alpha chain of interleukin-15 receptor: a proinflammatory molecule associated with tumor progression in head and neck cancer", Cancer Res, vol. 68 (10), May 15, 2008, pp. 3907-3914.

Bamford et al., "Interleukin (IL)15/IL-T production by the adult T-cell leukemia cell line HuT-102 is associated with a human T-celilymphotrophic virus type I region /IL-15 fusion message that lacks many upstream AUGs that normally attenuates IL-15 mRNA translation", Proc. Natl. Acad. Sci. USA; vol. 93(7), Apr. 2, 1996, pp. 2897-2902.

Bamford et al., "The 5' untranslated region, signal peptide, and the coding sequence of the carboxyl terminus of IL-15 participate in its multifaceted translational control", Journal of Immunology, vol. 160(9), May 1, 1998, pp. 4418-4426.

Bamford et al., "The interleukin (IL) 2 receptor beta chain is shared by IL-2 and a cytokine, provisionally designated IL-T, that stimulates T-cell proliferation and the induction of lymphokine-activated killer cells", Proceedings of the National Academy of Sciences USA, vol. 91(11), May 24, 1994, pp. 4940-4944.

Becker et al., "Interleukin 15 is required for proliferative renewal of virus-specific memory CD8 T cells", J Expl Med. vol. 195(12), Jun. 17, 2002, pp. 1541-1548.

Berard et al., "IL-15 Promotes the Survival of Naive and Memory Phenotype CD8(+) T Cells", Journal of Immunology, vol. 170, 2003, pp. 5018-5026.

Bergamaschi et al., "Secretion and Biological Activity of Short Signal Peptide IL-15 Is Chaperoned by IL-15 Receptor Alpha In Vivo", The Journal of Immunology, vol. 183, No. 5, Sep. 2009, pp. 3064-3072.

Berger et al., "Safety and immunologic effects of IL-15 administration in nonhuman primates", Blood, vol. 114(12), Sep. 17, 2009, pp. 2417-2426.

Bernard et al., "Identification of an interleukin-15alpha receptor-binding site on human interleukin-15", J Biol Chem. vol. 279(23), Jun. 4, 2004, pp. 24313-24322.

Bindon et al., "Clearance rates and systemic effects of intravenously administered interleukin 2 (IL-2) containing preparations in human subjects", Br. J. Cancer, vol. 47(1), 1983, pp. 123-133.

(56) References Cited

OTHER PUBLICATIONS

Bork, "Powers and Pitfalls in Sequence Analysis: The 70% Hurdle", Genome Research vol. 10, 2000, pp. 398-400.
Brocker et al., "Survival of mature CD4 T lymphocytes is dependent on major histocompatibility complex class II-expressina dendritic cells", J Exp Med, vol. 186(8), Oct. 20, 1997, pp. 1223-1232.
Budagian et al., "Reverse signaling through membrane-bound interleukin-15", J Bioi Chem, vol. 279(40), Oct. 1, 2004, pp. 42192-42201.
Burkett et al., "Coordinate expression and trans presentation of interleukin (IL)-15Ralpha and IL-15 supports natural killer cell and memory CD8+ T cell homeostasis", J Exp Med., vol. 200(7), Oct. 4, 2004, pp. 825-834.
Burkett et al., "IL-15R alpha expression on CD8+ T cells is dispensable forT cell Memory", Proc Natl Acad Sci USA. vol. 100, 2003, pp. 4724-4729.
Burton et al., "A lymphokin, provisionally designated interleukin-t and produced by a human adult T-cellleukemia line, stimulates T-cell proliferation and the induction of lymphokine-activated killer-cells", Proc Natl Acad Sci USA, vol. 91 (11), May 24, 1994, pp. 4935-4939.
Cao et al., "Interleukin 15 Protects against Toxicity and Potentiates Antitumor Activity of 5-Fluorouracil Alone and in Combination with Leucovorin in Rats Bearing Colorectal Cancer", Cancer Research vol. 58, 1998, 1695-1699.
Carson et al., "Interleukin (IL) 15 is a novel cytokine that activates human natural killer cells via components of the IL-2 receptor", J Exp Med, vol. 180(4), Oct. 1, 1994, pp. 1395-1403.
Castelli et al., "Mature dendritic cells can enhance CDS+ cell non cytotoxic anti-HIV responses: the role of IL-15", Blood, vol. 103, 2004, pp. 2699-2704.
Chapoval et al., "Combination chemotherapy and IL-15 administration induce permanent tumor regression in a mouse lung tumor model: NK and T cell-mediated effects antagonized by B cells", J Immunol, vol. 161(12), Dec. 15, 1998, pp. 6977-6984.
Chehimi et al., "IL-15 enhances immune functions during HIV infection", Journal of Immunology, vol. 158(12), Jun. 15, 1997, pp. 5978-5987.
Chirifu et al., "Crystal structure of the IL-15-IL-15Ralpha complex, a cytokine-receptor unit presented in trans", Nat. Immunol., vol. 8(9), 2007, pp. 1001-1007.
Chitnis et al., "Determinants of HIV-Specific CDS T-cell responses in HIV-infected pediatric patients and enhancement of HIV-gagspecitic responses with exogenous IL-15", Clin Irnrnunol, vol. 107(1), 2003, pp. 36-45.
Cho et al., "Homeostasis-stimulated proliferation drives naive T cells to differentiate directly into memory T cells", J Exp Med, vol. 192(4), Aug. 21, 2000, pp. 549-556.
Cooper et al., "In vivo evidence for a dependence on interleukin 15 for survival of natural killer cells", Blood, vol. 100(10), Nov. 15, 2002, pp. 3633-3638.
Davis et al., "Reduction of Immunogenicity and Extension of Circulating Half-life of Peptides and Proteins", Peptide and Protein Drug Delivery, Marcel Deker Inc., New York, 1991, pp. 831-864.
De Jong et al., "Interaction of IL-15 with the shared IL-2 receptor beta and gamma c subunits. The IL-15/beta/gamma c receptor-ligand complex is less stable than the IL-2/beta/gamma c receptor-ligand complex", J Immunol; vol. 156(4), Feb. 15, 1996, pp. 1339-1348.
Dean et al., "Cloning and expression of feline interleukin 15", Cytokine, Academic Press Ltd., vol. 29, No. 2, Jan. 21, 2005, pp. 77-83.
Dubois et al., "IL-15Ralpha recycles and presents IL-15 in trans to neighboring cells", Immunity, vol. 17(5), Nov. 2002, pp. 537-547.
Dubois et al., "Natural splicing of exon 2 of human interleukin-15 receptor a-chain mRNA results in a shortened form with a distinct pattern of expression", J Bioi Chem, vol. 274(38), Sep. 17, 1999, pp. 26978-26984.

Dudley et al., "Adoptive cell transfer therapy following nonmyeloablative but lymphodepleting chemotherapy for the treatment of patients with refractory metastatic melanoma", J Clin Oncol, vol. 23 (10), Apr. 1, 2005, pp. 2346-2357.
Dummer et al., "T cell homeostatic proliferation elicits effective antitumor autoimmunity", J Clin Invest, vol. 110(2), 2002, pp. 185-192.
European Patent Application No. 06784439.9 , "Supplementary European Search Report", dated Apr. 22, 2009, 9 pages.
European Patent Application No. 10752466.2 , Office Action, dated Feb. 13, 2014, 5 pages.
Epardaud et al., "Interleukin-15/interleukin-15R alpha complexes promote destruction of established tumors by reviving tumor-resident CD8+ T cells", Cancer Res. vol. 68(8), Apr. 15, 2008, pp. 2972-2983.
Fehniger et al., "Interleukin 15: biology and relevance to human disease", Blood, vol. 97(1), Jan. 1, 2001, pp. 14-32.
Ferrari-Lacraz , "Targeting IL-15 receptor-bearing cells with an antagonist mutant IL-15/Fc protein prevents disease development and progression in murine collagen-induced arthritis", J Immunol. vol. 173(9), Nov. 1, 2004, pp. 58'18-5826.
Fewkes et al., "Novel gamma-chain cytokines as candidate immune modulators in immune therapies for cancer", Cancer J., vol. 16(4), 2010, pp. 392-398.
Fischer et al., "A bioactive designer cytokine for human hematopoietic progenitor cell expansion", Nat Biotechnol, vol. 15(2), 1997, pp. 142-145.
Forcina et al., "Interleukin-15 modulates interferon-gamma and betachemokine production in patients with HIV infection: implications for immune-based therapy", Cytokine, vol. 25(6), Mar. 21, 2004, pp. 2S3-290.
Giri et al., "Identification and cloning of a novelII-15 binding protein that is structurally related to the alpha chain of the IL-2 receptor", EMBO J, vol. 14(15), Aug. 1, 1995, pp. 3654-3663.
Giri et al., "IL-15, a novel T cell growth factor that shares activities and receptor components with IL-2", Leukocyte Biol, vol. 57(5), 1995, pp. 763-766.
Giri et al., "Utilization of the beta and gamma chains of the IL-2 receptor by the novel cytokine IL-15", EMBO J, vol. 13(12), 1994, pp. 2822-2830.
Giron-Michel et al., "Membrane-bound and soluble IL-15/IL-15Ralpha complexes display differential signaling and functions on human hematopoietic progenitors", Blood, vol. 106, No. 7, Oct. 1, 2005, pp. 2302-2310.
Goldrath et al., "Cytokine Requirements for Acute and Basal Homeostatic Proliferation of Naive and Memory CD8+ T Cells", J Exp Med, vol. 195(12), Jun. 17, 2002, pp. 1515-1522.
Goldrath et al., "Low-affinity ligands for the TCR drive proliferation of mature CD8+ T cells in lymphopenic hosts", Immunity, vol. 11(2), 1999, pp. 183-190.
Grabstein et al., "Cloning of a T cell growth factor that interacts with the beta chain of the interleukin-2 receptor", Science, vol. 264(5161), May 13, 1994, pp. 965-96S.
Hsu et al., "Primary Human T Lymphocytes Engineered with a Codon-Optimized IL-15 Gene Resist Cytokine Withdrawal-Induced Apoptosis and Persist Long-Term in the Absence of Exogenous Cytokine", The Journal of Immunology, vol. 175, No. 11, Dec. 2005, pp. 7226-7234.
Jalah , "Efficient systemic expression of bioactive IL-15 in mice upon delivery of optimized DNA expression plasmids", DNA and Cell Biology, Mary Ann Liebert, New York, NY, US.LNKD DOI 10.1089/DNA.2007.0645, vol. 26, No. 14, Dec. 1, 2007, pp. 827-840.
Johnston et al., "Tyrosine phosphorylation and activation of STAT5, STAT3, and Janus kinases by interleukins 2 and 15", Proc Natl Acad Sci USA. vol. 92(19), Sep. 12, 1995, pp. 8705-8709.
Judge et al., "Interleukin 15 controls both proliferation and survival of a subset of memory-phenotype CD8(+) T cells", J Exp Med, vol. 196(7), Oct. 7, 2002, pp. 935-946.
Jung et al., "In Vivo Depletion of CD11c+ Dendritic Cells Abrogates Priming of CD8+ T Cells by Exogenous Cell-Associated Antigens", Immunity, vol. 17(2), 2002, pp. 211-220.

(56) References Cited

OTHER PUBLICATIONS

Kassiotis et al., "Impairment of immunological memory in the absence of MHC despite survival of memory T cells", Nat Immunol, vol. 3(3), 2002, pp. 244-250.
Kennedy et al., "Reversible Defects in Natural Killer and Memory CD8 T Cell Lineages in Interleukin 15-Deficient Mice", J. Exp. Med., 2000, pp. 771-780.
Khan et al., "IL-15 augments CD8+ T cell-mediated immunity against Toxoplasma gondii infection in mice", J Immunol, vol. 157(5), 1996, pp. 2103-2108.
Khan et al., "Treatment with Soluble Interleukin-15Rα Exacerbates Intracellular Parasitic Infection by Blocking the Development of Memory CD8+ T Cell Response", J Exp Med, vol. 195(11), Jun. 3, 2002, pp. 1463-1470.
Kieper et al., "Homeostatic expansion and phenotypic conversion of naive T cells in response to self peptideyMHC ligands", PNAS vol. 96 No. 23, 2000, pp. 13306-13311.
Kim et al., "Generation of mucosal cytotoxic T cells against soluble protein by tissue-specific environmental and costimulatory signals", Proc Natl Acad Sci USA, vol. 95(18), Sep. 1, 1998, pp. 10814-10819.
Kishimoto, "IL-6: from its discovery to clinical applications", International Immunology, vol. 22(5), May, 2010, pp. 347-352.
Klebanoff et al., "IL-15 enhances the in vivo antitumor activity of tumor-reactive CD8+ T cells", Proc Natl Acad Sci USA, vol. 101(7), Feb. 17, 2004, pp. 1969-1974.
Kobayashi et al., "Differences in biodistribution, pharmacokinetics, and tumor targeting between interleukins 2 and 15", Cancer Research, vol. 60(13), Jul. 1, 2000, pp. 3577-3583.
Koka et al., "Interleukin (IL)-15R[alpha]-deficient natural killer cells survive in normal but not IL-15R[alpha]-deficient mice", J Exp Med, vol. 197(8), Apr. 21, 2003, pp. 977-984.
Krause et al., "Genomic structure and chromosomal localization of the human interleukin 15 gene (IL-15)", Cytokine. vol. 8(9), 1996, pp. 667-674.
Ku et al., "Control of homeostasis of CD8+ memory T cells by opposing cytokines", Science, vol. 288, 2000, pp. 675-678.
Kutzler et al., "Coimmunization with an Optimized IL-15 Plasmid Results in Enhanced Function and Longevity of CD8 T Cells that Are Partially Independent of CD4 T Cell Help.", Journal of Immunology, vol. 175, Jul. 2005, pp. 112-123.
Lodolce et al., "IL-15 Receptor Maintains Lymphoid Homeostasis by Supporting Lymphocyte Homing and Proliferation.", Immunity. vol. 9, 1998, pp. 669-676.
Lodolce et al., "T Cell-Independent Interleukin 15rα Signals Are Required for Bystander Proliferation", J Exp Med., vol. 194(8), Oct. 15, 2001, pp. 1187-1194.
Lum et al., "Differential effects of interleukin-7 and interleukin-15 on NK cell anti-human immunodeficiency virus activity", J Virol, vol. 78(11), Jun. 2004, pp. 6033-6042.
Lyons et al., "Determination of lymphocyte division by flow cytometry", J Immunol Methods, vol. 171(1), May 2, 1994, pp. 131-137.
Maeurer et al., "Interleukin-7 or interleukin-15 enhances survival of *Mycobacterium tuberculosis*-infected mice", Infect Immun, vol. 68(5), 2000, pp. 2962-2970.
Masopust et al., "Direct analysis of the dynamics of the intestinal mucosa CD8 T cell response to systemic virus infection", J Immunol, vol. 166(4), Feb. 15, 2001, pp. 2348-2356.
Mastroianni et al., "Interleukin-15 enhances neutrophil functional activity in patients with human immunodeficiency virus infection", Blood, vol. 96, Sep. 1, 2001, pp. 1979-1984.
Matsumoto et al., "On-column refolding and characterization of soluble human interleukin-15 receptor alpha-chain produced in *Escherichia coli*, Protein Expr Purif, vol. 31(1), Sep. 2003, pp. 64-71.
Mortier et al., "Natural, proteolytic release of a soluble form of human IL-15 receptor alpha-chain that behaves as a specific, high affinity IL-15 antagonist", J. Immunol., vol. 173, No. 3, 2004, pp. 1681-1688.

Mortier et al., "Soluble interleukin-15 receptor alpha (IL-15R alpha)-sushi as a selective and potent agonist of IL-15 action through IL-15R beta/gamma. Hyperagonist IL-15 x IL-15R alpha fusion proteins", Journal of Biological Chemistry, vol. 281, No. 3, Nov. 11, 2005, pp. 1612-1619.
Mueller et al., "IL-15 enhances survival and function of HIV-specific CD8+ T cells", Blood, vol. 101(3), Feb. 1, 2003, pp. 1024-1029.
Murali-Krishna et al., "Persistence of memory CD8 T cells in MHC class I-deficient mice", Science, vol. 286(5443), Nov. 12, 1999, pp. 1377-1381.
Nguyen et al., "TNF receptor 1 (TNFR1) and CD95 are not required for T cell deletion after virus infection but contribute to peptide-induced deletion under limited conditions", European Journal of Immunology, vol. 30, Issue 2, 2000, pp. 683-688.
Nishimura et al., "A novel autoregulatory mechanism for transcriptional activation of the IL-15 gene by a nonsecretable isoform of IL-15 generated by alternative splicing", FASEB J., vol. 19(1), 2005, pp. 19-28.
Oehen et al., "Differentiation of naive CTL to effector and memory CTL: correlation of effector function with phenotype and cell division", J Immunol, vol. 161(10), Nov. 15, 1998, pp. 5338-5346.
Oh et al., "Coadministration of HIV vaccine vectors with vaccinia viruses expressing IL-15 but not IL-2 induces long-lasting cellular immunity", Proc Natl Acad Sci U S A, vol. 100(6), Mar. 18, 2003, pp. 3392-3397.
Oh et al., "IL-15/IL-15Ra-Mediated Avidity Maturation of Memory CD8+ T Cells", PNAS, vol. 101, No. 42, Oct. 19, 2004, pp. 15154-15159.
Ohteki et al., "Critical role of IL-15-IL-15R for antigen-presenting cell functions in the innate immune response", Nat Immunol, vol. 2(12), 2001, pp. 1138-1143.
Olsen et al., "Crystal structure of the interleukin-15Interleukin-15 receptor alpha complex", Journal of Biological Chemistry, vol. 282(51), Dec. 21, 2007, pp. 37191-37204.
Overwijk et al., "Functions of γC cytokines in immune homeostasis: current and potential clinical applications", Clin Immunol, vol. 132(2), 2009, pp. 153-165.
Park et al., "Follicular dendritic cells produce IL-15 that enhances germinal center B cell proliferation in membrane-bound form", J Immunol, vol. 173(11), Dec. 1, 2004, pp. 6676-6683.
International Patent Application No. PCT/US2006/019403, International Search Report and Written Opinion, dated May 11, 2007, 7 pages.
International Patent Application No. PCT/US2008/008084, International Preliminary Report on Patentability, dated Jan. 5, 2010, 8 pages.
International Patent Application No. PCT/US2008/008084, International Search Report and Written Opinion, dated Dec. 30, 2008, 9 pages.
International Patent Application No. PCT/US2010/045511, International Search Report, dated Nov. 11, 2011, 5 pages.
Pereno et al., "IL-15/IL-15Ralpha intracellular trafficking in human melanoma cells and signal transduction through the IL-15Ralpha", Oncogene, vol. 19(45), Oct. 26, 2000, pp. 5153-5162.
Pettit et al., "Structure-function studies of interleukin 15 using site-specific mutagenesis, polyethylene glycol conjugation, and homology modeling", J Biol Chem, vol. 272(4), Jan. 24, 1997, pp. 2312-2318.
Pflanz, "A fusion protein of interleukin-11 and soluble interleukin-11 receptor acts as a superagonist on cells expressing gp130", FEBS Lett., 450(1-2), Apr. 30, 1999, pp. 117-122.
Porter et al., "T-cell reconstitution and expansion after hematopoietic stem cell transplantation: 'T' it up!", Bone Marrow Transplant, vol. 35(10), 2005, pp. 935-942.
Prlic et al., "In vivo survival and homeostatic proliferation of natural killer cells", J Exp Med, vol. 197(8), Apr. 21, 2003, pp. 967-976.
Roychowdhury, "Failed adoptive immunotherapy with tumor-specific T cells: reversal with low-dose interleukin 15 but not low-dose interleukin 2", Cancer Res. vol. 64(21), Nov. 1, 2004, pp. 8062-8067.

(56) References Cited

OTHER PUBLICATIONS

Rubinstein et al., "Converting IL-15 to a superagonist by binding to soluble IL-15R{alpha}", PNAS, vol. 103, No. 24, Jun. 13, 2006, pp. 9166-9171.

Rubinstein et al., "Systemic administration of IL-15 augments the antigen-specific primary CD8+ T cell response following vaccination with peptide-pulsed dendritic cells", J Immunol, vol. 169(9), Nov. 1, 2002, pp. 4928-4935.

Ruchatz et al., "Soluble IL-15 receptor alpha-chain administration prevents murine collagen-induced arthritis: a role for IL-15 in development of antigen-induced immunopathology", J Immunol., vol. 160, No. 11, 1998, pp. 5654-5660.

Ruckert, "Dendritic cell-derived IL-15 controls the induction of CD8 T cell immune responses", Eur J Immunol, vol. 33(12), Dec. 2003, pp. 3493-3503.

Sandau, "Cutting edge: transpresentation of IL-15 by bone marrow-derived cells necessitates expression of IL-15 and IL-15R alpha by the same cells", J Immunol, vol. 173(11), Dec. 1, 2004, pp. 6537-6541.

Sandau et al., "IL-15 Is Required for Sustained Lymphopenia-Driven Proliferation and Accumulation of CDS T Cells", The Journal of Immunology vol. 179, 2007, 120-125.

Sato et al., "The IL-15/IL-15Ralpha on cell surfaces enables sustained IL-15 activity and contributes to the long survival of CD8 memory T cells", Proc Natl Acad Sci USA, vol. 104(2), Jan. 9, 2007, pp. 588-593.

Scheeler et al., "Interleukin-6 and its receptor: from bench to bedside", Med Microbiol Immunol, vol. 195(4), Dec. 2006, pp. 173-183.

Schluns et al., "Distinct cell types control lymphoid subset development by means of IL-15 and IL-15 receptor alpha expression", Proc Natl Acad Sci USA, vol. 101(15), Apr. 13, 2004, pp. 5616-5621.

Schluns et al., "Interleukin-7 mediates the homeostasis of naive and memory CD8 T cells in vivo", Nat Immunol, vol. 1(5), Nov. 2000, pp. 426-432.

Schluns et al., "Requirement for IL-15 in the generation of primary and memory antigen-specific CD8 T cells", J Immunol, vol. 168(10), May 15, 2002, pp. 4827-4831.

Schluns et al., "The roles of interleukin-15 receptor α: Trans-presentation, receptor component, or both", The International Journal of Biochemistry & Cell Biology vol. 37, Issue 8, Aug. 2005, pp. 1567-1571.

Schluns, "Trans-regulation of memory CDS T cell proliferation by IL-15Ra+ bone marrow-derived cells", Blood, vol. 103(3), 2004, pp. 988-994.

Skolnick, "From Genes to Protein Structure and Function: Novel Applications of Computational Approaches in the Genomic Era", Trends in Biotech., vol. 18, No. 1, 2000, pp. 34-39.

Smith et al., "Selective blockade of IL-15 by soluble IL-15 receptor alpha-chain enhances cardiac allograft survival", J Immunol., vol. 165, No. 6, 2000, pp. 3444-3450.

Stoklasek et al., "Combined IL-15/IL-15Ra Immunotherapy Maximizes IL-15 Activity In Vivo", The Journal of Immunology, vol. 177(9), Nov. 1, 2006, pp. 6072-6080.

Tan et al., "Interleukin (IL)-15 and IL-7 jointly regulate homeostatic proliferation of memory phenotype CD8+ cells but are not required for memory phenotype CD4+ cells", J Exp Med, vol. 195(12), Jun. 17, 2002, pp. 1523-1532.

Tokuriki et al., "Stability effects of mutations and protein evolvability", Current Opinion in Structural Biology vol. 19, 2009, pp. 596-604.

Tsunobuchi et al., "A Protective Role of Interleukin-15 in a Mouse Model for Systemic Infection with Herpes Simplex Virus", Virology, vol. 275, Issue 1, Sep. 15, 2000, pp. 57-66.

Umemura et al., "Overexpression of IL-15 in vivo enhances protection against *Mycobacterium bovis* bacillus Calmette-Guerin infection via augmentation of NK and T cytotoxic 1 responses", J Immunol, vol. 167(2), Jul. 15, 2001, pp. 946-956.

Van Belle, "IL-15 and IL-15Ralpha in CD4+T cell immunity", Arch Immunol Ther Exp, vol. 53(2), 2005, pp. 115-126.

Villinger et al., "IL-15 is superior to IL-2 in the generation of long-lived antigen specific memory CD4 and CD8 T cells in rhesus macaques", Vaccine, vol. 22, 2004, pp. 3510-3521.

Waldmann et al., "Contrasting roles of IL-2 and IL-15 in the life and death of lymphocytes: implications for immunotherapy", Immunity,vol. 14(2), 2001, pp. 105-110.

Waldmann, "The biology of interleukin-2 and interleukin-15: implications for cancer therapy and vaccine design", Nat Rev Immunol., vol. 6(8), 2006, pp. 595-601.

Waldmann et al., "The multifaceted regulation of interleukin-15 expression and the role of this cytokine in NK cell differentiation and host response to intracellular pathogens", Annu Rev Immunol., vol. 17, 1999, pp. 19-49.

Wang et al., "The interleukin 2 receptor", Journal of Experimental Medicine, vol. 166, 1987, pp. 1055-1069.

Warren et al., "Analysis of the costimulatory role of IL-2 and IL-15 in initiating proliferation of resting (CD56dim) human NK cells", J Immunol, vol. 156(9), 1996, pp. 3254-3259.

Wei et al., "The Sushi domain of soluble IL-15 receptor alpha is essential for binding IL-15 and inhibiting inflammatory and allogenic responses in vitro and in vivo", J Immunol., vol. 167(1), Jul. 1, 2001, pp. 277-282.

Wells, "Additivity of Mutational.Effectsin Proteins", Biochemistry vol. 29,No. 37, Sep. 18, 1990, 8509-8517.

Williams et al., "T cell immune reconstitution following lymphodepletion", Seminars in Immunology, vol. 19(5), 2007, pp. 318-330.

Willlams et al., "T cell immune reconstitution following lymphodepletion", Seminars in Immunology,W.B: Saunders Company, PA, US ~NKD-001:10.1 Ot6/J.SMIM.2007.1 0.004, vol. 19 No. 5,19, Nov. 19, 2007, pp. 318-330.

Wrzesinski et al., "Less is more: lymphodepletion followed by hematopoietic stem cell transplant augments adoptive T-cell-based anti-tumor immunotherapy", Curr Opin Immunol, vol. 17(2), 2005, pp. 195-201.

Wysocka et al., "Enhancement of the host immune responses in cutaneous T-cell lymphoma by CpG oligodeoxynucleotides and IL-15", Blood, vol. 104(13), Dec. 15, 2004, pp. 4142-4149.

Zammit, "Dendritic cells maximize the memory CD8 T cell response to infection", Immunity, vol. 22(5), 2005, pp. 561-70.

Zeng et al., "Synergy of IL-21 and IL-15 in regulating CD8+ T cell expansion and function", J Ex(2 Med, vol. 201(1), Jan. 3, 2005, pp. 139-148.

Zhang et al., "Potent and Selective Stimulation of Memory-Phenotype CD8+ T Cells In Vivo by IL-15", Immunity, vol. 8, No. 5, May 1998, pp. 591-599.

Bergamaschi et al., "Intracellular Interaction of Interleukin-15 with Its Receptor α during Production Leads to Mutual Stabilization and Increased Bioactivity" The Journal of Biological Chemistry 283(7):4189-4199, Feb. 2008.

Kotsakis, Cancer, 89:1380-1386 (2000).

* cited by examiner

HETERODIMERS OF IL-15 AND IL-15R ALPHA TO INCREASE THYMIC OUTPUT AND TO TREAT LYMPHOPENIA

CROSS REFERENCE TO RELATED APPLICATIONS

This application is a division of U.S. patent application Ser. No. 15/485,093, filed Apr. 11, 2017, now U.S. Pat. No. 10,093,710, which is a continuation of U.S. patent application Ser. No. 14/512,913, filed Oct. 13, 2014, now U.S. Pat. No. 9,975,937, which is a continuation of U.S. patent application Ser. No. 13/390,504, filed Feb. 14, 2012, now U.S. Pat. No. 8,871,191, which is a U.S. National Stage Appl. of International Appl. No. PCT/US2010/045511, filed Aug. 13, 2010, which claims the benefit of U.S. Prov. Appl. No. 61/234,152, filed on Aug. 14, 2009; and U.S. Prov. Appl. No. 61/234,155, filed Aug. 14, 2009. Each application is herein incorporated by reference.

REFERENCE TO A SEQUENCE LISTING SUBMITTED AS A TXT FILE

This application includes a Sequence Listing as a text file named "077867-1044133-581300US-SEQLIST.txt" created Apr. 10, 2017 and containing 66,032 bytes. The material contained in this text file is incorporated by reference.

FIELD OF THE INVENTION

The present invention provides compositions and methods for promoting the maturation and export of T cells from the thymus, e.g., to peripheral lymphoid and non-lymphoid tissues by contacting the thymus tissue, in vitro or in vivo, with interleukin (IL)-15.

The invention additionally provides methods for preventing, alleviating, reducing, and/or inhibiting lymphopenia or depletion of lymphocytes in peripheral tissues in a patient in need thereof by administering IL-15 to the patient.

BACKGROUND OF THE INVENTION

Two common gamma-chain cytokines, IL-2 and IL-7 are currently approved or considered for both AIDS and cancer immunotherapy. See, Sportes, et al., (2008) *J Exp Med* 205:1701-1714; Levy, Y. (2009) *J Clin Invest.* 119(4):997-100785; and Rosenberg, et al., (2006) *J Immunother* 29:313-319. No clinical experience exists with the gamma-chain cytokine IL-15. See, Cheever, (2008) *Immunological Reviews* 222:357-368.

IL-15 is a non-redundant cytokine important for the development, survival, and proliferation of natural killer (NK) and CD8+ T-cells. It shares with IL-2 the same IL-2 beta gamma receptor and has many similar effects on lymphocytes, but unlike IL-2 is not produced by lymphocytes but by a plethora of other cells including, importantly, antigen presenting cells and macrophages, and stroma cells in several tissues. The biological effects of IL-2 and IL-15 at the level of the organism are dramatically different, as shown by work in knockout mice: lack of IL-15 causes immune system defects, whereas lack of IL-2 causes immune activation and severe autoimmunity. See, Waldmann, (2006) *Nat Rev Immunol* 6:595-601; and Ma, et al., (2006) *Annu Rev Immunol* 24:657-679. Both cytokines are under tight and complex regulation at all steps of expression and secretion. The biological differences of IL-2 and IL-15 are determined by their different production sites, their strength of association with membrane receptor proteins termed IL-2 Receptor alpha and IL-15 Receptor alpha (IL-15Rα), respectively, and the regulation of these extra receptor molecules. IL-15 has been also reported to have a unique mechanism of action in vivo among the common gamma chain cytokines: IL-15 functions in a complex with IL-15Rα and depends on the co-expression by the same cells of IL-15Rα. See, Burkett, et al., (2004) *J Exp Med* 200: 825-834; Burkett, et al., (2003) *Proc Natl Acad Sci USA* 100:4724-4729; Dubois, et al., (2002) *Immunity* 17:537-547; Sandau, et al, (2004) *J Immunol* 173:6537-6541; Schluns, et al., (2004) *Blood* 103:988-994; Rubinstein, et al., (2006) *Proc Natl Acad Sci USA* 103:9166-9171; Bergamaschi, et al., (2008) *J Biol Chem* 283:4189-4199. IL-15 has non-redundant roles in the development and function of NK and intestinal intraepithelial lymphocytes (IELs). See, Cooper, et al., (2001) *Blood* 97:3146-3151. It stimulates cytolytic activity, cytokine secretion, proliferation and survival of NK cells. See, Fehniger, et al., (1999) *J Immunol* 162:4511-4520; Ross, et al., (1997) *Blood* 89:910-918; and Carson, et al., (1994) *J Exp Med* 180:1395-1403. IL-15 has a proliferative and survival effect on CD8+ memory T-cells and naive CD8+ T-cells. See, Tan, et al., (2002)*J Exp Med* 195:1523-1532; Zhang, et al., (1998) *Immunity* 8:591-599; Berard, et al., (2003) *J Immunol* 170:5018-5026; and Alves, et al., (2003) *Blood* 102:2541-2546.

Several studies have evaluated the effects of IL-15 administration in vivo. CD8+ memory T-cell proliferation increased after a single dose of IL-15 in normal mice. See, Zhang, et al., (1998) *Immunity* 8:591-599. Administration of IL-15 to mice enhanced the antitumor activity after syngeneic bone marrow transplantation (BMT) and antigen-specific primary CD8+ T-cell responses following vaccination with peptide-pulsed dendritic cells. See, Rubinstein, et al., (2002). *J Immunol* 169:4928-4935; Katsanis, et al., (1996) *Transplantation* 62:872-875. IL-15 also enhanced immune reconstitution after allogeneic bone marrow transplantation. See, Alpdogan, et al., (2005) *Blood* 105:865-873; and Evans, et al., (1997) *Cell Immunol* 179:66-73. The ability of IL-15 to promote growth, survival and activation of key lymphocyte populations make it also an attractive candidate for supporting growth in vitro and in vivo of cells for adoptive cell therapy. See, Rosenberg, et al., (2008) *Nat Rev Cancer* 8:299-308; and Berger, et al., (2008) *J Clin Invest* 118:294-305.

We have demonstrated that efficient production of IL-15 requires the expression of IL-15 and IL-15 Receptor alpha (IL-15Rα) in the same cell. See, Bergamaschi, et al., (2008) *J Biol Chem* 283:4189-4199. Co-production leads to intracellular association of IL-15 and IL-15Rα in the endoplasmic reticulum, stabilization of both molecules and efficient transport to the cell surface (FIG. 1). We showed that an additional critical step is the rapid cleavage and release of the IL-15/IL-15Rα complex from the cell surface, both in vitro and in vivo, resulting in a soluble, systemically active form of IL-15/IL-15Rα, in addition to the bioactive complex on the cell surface. See, Dubois, et al., (2002) *Immunity* 17:537-547; Bergamaschi, et al., (2008) *J Biol Chem* 283: 4189-4199; and Budagian, et al., (2004) *J Biol Chem* 279: 40368-40375. Our experiments using IL-15 complexed to a deletion mutant of IL-15Rα containing only the soluble Receptor alpha extracellular fragment demonstrated that this complex is bioactive in vivo in the absence of any membrane-bound form.

Therefore, we proposed that IL-15Rα is part of a heterodimeric IL-15 cytokine, rather than functioning as a cytokine receptor. These results have been supported by other investigators, and provide the basis for a better understanding of IL-15 biology. See, Duitman, et al., (2008) *Mol Cell Biol* 28:4851-4861; Mortier, et al., (2008) *J Exp Med* 205:1213-1225. The results also provide the molecular basis to explain some intriguing observations, including the requirement of production of IL-15 and IL-15Rα from the same cells for appropriate function in vivo. See, Sandau, et al., (2004) *J Immunol* 173:6537-6541; and Koka, et al., (2003) *J Exp Med* 197:977-984. Such results are fully explained by our finding that stabilization during co-expression in the same cell is required for physiological levels of IL-15 production. It has also been reported that the cells that physiologically express IL-15 also express IL-15Rα, consistent with IL-15 production as a heterodimer in the body. See, Dubois, et al., (2002) *Immunity* 17:537-547; Giri, et al., (1995) *J Leukoc Biol* 57:763-766; and Ruckert, et al., (2003) *Eur J Immunol* 33:3493-3503. Interpretation of all data available to date suggests that the main bioactive form of IL-15 is in a complex with the Receptor alpha either on the surface of the cells or in a soluble circulating form. It remains to be determined whether single-chain IL-15 is produced in the body in physiologically relevant levels and what is its exact function.

It has been previously reported that IL-15 secretion is inefficient. See, Bamford, et al., (1998) *J Immunol* 160: 4418-4426; Gaggero, et al., (1999) *Eur J Immunol* 29:1265-1274; Kurys, et al., (2000) *J Biol Chem* 275:30653-30659; Onu, et al., (1997) *J Immunol* 158:255-262; and Tagaya, et al., (1997) *Proc Natl Acad Sci USA* 94:14444-14449. We took a systematic approach to develop IL-15 expression vectors producing high levels of bioactive cytokine based on the observation that multiple regulatory steps during gene expression create bottlenecks of IL-15 production. See, Jalah, et al., (2007) *DNA Cell Biol* 26:827-840; and Kutzler, et al., (2005) *J Immunol* 175:112-123. We showed that combination of two approaches, namely mRNA optimization (RNA/codon optimization) of the IL-15 coding sequences and substitution of the signal peptide with other efficient secretory signals resulted in synergistically improved expression and secretion of bioactive IL-15. See, Jalah, et al., (2007) *DNA Cell Biol* 26:827-840. Taking advantage of the stabilization of IL-15 by co-expression with IL-15Rα described above, we produced equally optimized vectors for IL-15Rα and combination vectors expressing both molecules, as well as combinations producing only the soluble heterodimeric cytokine. The final improvement in expression of secreted IL-15 was more than 1,000 fold compared to wt IL-15 cDNA, as determined by in vitro and in vivo experiments. We have produced similar vectors for mouse, macaque and human IL-15/IL-15Rα.

Two forms of interleukin-15 (IL-15) are known, containing a long signal peptide (LSP) or a short signal peptide (SSP), respectively. The two forms are produced by alternatively spliced mRNAs and differ only in the length of their signal peptides, the 48 aa long signal peptide or the 21 aa short signal peptide (120, 121, 125-127). See, Onu, et al., (1997) *J Immunol* 158:255-262; Tagaya, et al., (1997) *Proc Natl Acad Sci USA* 94:14444-14449; Meazza, et al., (1997) *Eur J Immunol* 27:1049-1054; Meazza, et al., (1996) *Oncogene* 12:2187-2192; and Nishimura, et al., (1998) *J Immunol* 160:936-942. Whereas LSP IL-15 is secreted, SSP IL-15 remains exclusively intracellular and its function is not known. It has been proposed that SSP IL-15 may have a regulatory function since it was detected both in the cytoplasm and the nucleus of DNA-transfected cells. The SSP signal affects both stability and localization of IL-15, since lower levels of the SSP isoform were detected when the two isoforms were expressed from similar vectors. See, See, Onu, et al., (1997) *J Immunol* 158:255-262; Tagaya, et al., (1997) *Proc Natl Acad Sci USA* 94:14444-14449; and Bergamaschi, et al., (2009) *J Immunol*, 5:3064-72.

In Bergamaschi, we showed that, similar to LSP IL-15, SSP IL-15 is stabilized and secreted efficiently upon coexpression of IL-15Rα in the same cell. See, Bergamaschi, et al., (2009) *J Immunol*, supra. Co-expression of SSP IL-15 and IL-15Rα in mice showed increased plasma levels of bioactive SSP IL-15 and mobilization and expansion of NK and T cells. Therefore, SSP IL-15 is secreted and bioactive when produced as a heterodimer with IL-15Rα in the same cell. The apparent stability of this complex both in vitro and in vivo is lower compared to LSP IL-15/IL-15Rα complex, as revealed by direct comparisons. This results in lower production of secreted bioactive IL-15/IL-15Rα. Thus, alternative splicing may provide the cell with the ability to produce different levels of bioactive IL-15. Since both forms of IL-15 may be produced in the same cell by alternative splicing, an additional level of regulation is possible. We showed that when both LSP IL-15 and SSP IL-15 are produced in the same cell they compete for the binding to IL-15Rα, resulting in lower levels of bioactive IL-15. Therefore, co-expressed SSP IL-15 acts as competitive inhibitor of LSP IL-15. This suggests that usage of alternative splicing is an additional level of control of IL-15 activity. Expression of both SSP and LSP forms of IL-15 appears to be conserved in many mammals, suggesting that SSP may be important for expressing a form of IL-15 with lower magnitude and duration of biological effects. The present invention is based, in part, on the discovery that SSP IL-15, which is produced in the thymus, is important for intrathymic effects on lymphocyte differentiation and maturation.

BRIEF SUMMARY OF THE INVENTION

The present invention provides compositions and methods that promote the maturation of T cells in the thymus and the output or migration of mature and/or activated lymphocytes from a central lymphoid organ to peripheral tissues by administration of IL-15. The invention is based, in part, on the discovery that IL-15 promotes the migration of T cells out of the thymus and subsequently to peripheral lymphoid (e.g., spleen and lymph node) and non-lymphoid tissues (e.g., lung and liver). In some embodiments, the methods concurrently promote the maturation of lymphocytes in the bone marrow, e.g., B cells and natural killer (NK) cells, and their migration to peripheral lymphoid and non-lymphoid tissues.

Accordingly, in one aspect, the invention provides methods of promoting T-cell maturation in thymic tissue comprising contacting the thymic tissue with IL-15.

The thymic tissue can be in vivo or in vitro.

In a related aspect, the invention provides methods of promoting the migration of lymphocytes from a central lymphoid tissue to one or more peripheral tissues in a subject in need thereof comprising administering to the subject IL-15.

With respect to the embodiments, in some embodiments, the lymphocytes are T cells and the central lymphoid tissue is thymus. In some embodiments, the lymphocytes are B cells and/or NK cells and the central lymphoid tissue is bone marrow.

In some embodiments, the lymphocytes migrating from the central lymphoid tissues are mature but not activated. In some embodiments, the lymphocytes migrating from the central lymphoid tissues are mature and activated. In some embodiments, the T cells migrating from the thymus are mature single positive (CD4+ or CD8+) T cells. The T cells induced to leave the thymus may be activated or not activated.

The invention additionally provides methods for preventing, treating, alleviating, reducing and/or inhibiting lymphopenia or depletion of lymphocytes in peripheral tissues by administration of IL-15. The present invention further provides methods for promoting the repopulation of peripheral tissues that have been depleted of lymphocytes and accelerating the recovery from lymphocyte depletion of peripheral tissues by the administration of IL-15.

Accordingly, in one aspect, the invention provides methods of preventing, reducing or inhibiting lymphopenia or depletion of lymphocytes in peripheral tissues in an individual in need thereof comprising systemically administering IL-15 to the individual.

In some embodiments, the lymphopenia or lymphocyte depletion of peripheral tissues is drug-induced. For example, the individual may be receiving anticancer drugs or antiviral drugs, or radiation therapy that induces lymphopenia or lymphocyte depletion of peripheral tissues.

In some embodiments, the IL-15 is co-administered with an agent that causes depletion of lymphocytes in peripheral tissues, e.g., an anticancer or an antiviral agent. In some embodiments, the IL-15 is co-administered with radiation therapy.

In a related aspect, the invention provides methods of promoting or accelerating the repopulation of lymphocytes in peripheral tissues in an individual in need thereof comprising systemically administering IL-15 to the individual.

In some embodiments, the systemic administration of IL-15 prevents or reduces the depletion of or promotes or accelerates the repopulation of one or more of T cells, B cells or NK cells. In some embodiments, the systemic administration of IL-15 prevents or reduces the depletion of or promotes or accelerates the repopulation of one or more of CD4+ T cells or CD8+ T cells.

In some embodiments of the methods of the invention, the subject or patient is a mammal. In some embodiments, the subject or patient is a human.

When administered in vivo the IL-15 can be administered systemically, including without limitation, enterally (i.e., orally) or parenterally, e.g., intravenously, intramuscularly, subcutaneously, intradermally, intranasally, or inhalationally. In some embodiments, the IL-15 is administered locally, for example, intrathymically.

Systemic administration is at a dose that is sufficient to maintain IL-15 at supraphysiologic levels. For example, IL-15 DNA or protein can be administered at a dose sufficient to achieve plasma levels of IL-15 of about 1 to 1000 ng/ml, for example, plasma levels of IL-15 of about 10 to 1000 ng/ml. The IL-15 and IL-15Rα can be delivered in equimolar amounts. Such a range of IL-15 plasma concentrations can be achieved, e.g., after intramuscular electroporation of about 0.1 mg IL-15/IL-15Rα expressing DNA plasmid per kg body weight. Alternatively, an IL-15/IL-15Rα protein complex can be administered at a dose of about 0.01 to 0.5 mg/kg. IL-15/IL-15Rα polypeptides can be administered, e.g., subcutaneously, intramuscularly, intraperitoneally or intravenously. See, e.g., Rosati, et al., *Vaccine* (2008) 26:5223-5229.

The IL-15 can be administered as a polypeptide or as a polynucleotide encoding IL-15. In some embodiments, the IL-15 is co-administered with IL-15Rα, e.g., as a heterodimer. The co-administered IL-15Rα can be a polypeptide or a polynucleotide encoding IL-15Rα. The co-administered IL-15Rα can be in the same or different form as the IL-15. For example, both the IL-15 and the IL-15Rα can be administered as polypeptides or as one or more polynucleotides encoding IL-15 and/or IL15Rα. Alternatively, one of the IL-15 and the IL15Rα can be administered as a polypeptide and the other as a polynucleotide encoding either IL-15 or IL-15Rα. In some embodiments, the IL-15Rα is a soluble IL-15Rα. In some embodiments, the IL-15Rα may be administered in the form of an Fc fusion protein or a polynucleotide that encodes an Fc fusion protein.

In some embodiments, the IL-15 and the IL-15Rα are concurrently administered as one or more polynucleotides encoding IL-15 and/or IL-15Rα. The polynucleotide encoding IL-15 and the polynucleotide encoding IL-15Rα can be on the same or separate vectors, for example, single or multiple plasmid vectors. In some embodiments, the IL-15 and the IL-15Rα polynucleotides are concurrently expressed from a plasmid vector of SEQ ID NO: 13, SEQ ID NO:14, SEQ ID NO:15, SEQ ID NO:16, or SEQ ID NO: 19.

In some embodiments, the polynucleotides encoding one or both of IL-15 and the IL-15Rα are wild-type coding sequences. In some embodiments, the polynucleotide encoding IL-15 shares at least 90%, 91%, 92%, 93%, 94%, 95%, 96%, 97%, 98%, 99% or 100% sequence identity to SEQ ID NO: 1. In some embodiments, the polynucleotide encoding IL-15Rα shares at least 90%, 91%, 92%, 93%, 94%, 95%, 96%, 97%, 98%, 99% or 100% sequence identity to SEQ ID NO:5 or SEQ ID NO:7.

In some embodiments, the polynucleotides encoding one or both of IL-15 and the IL-15Rα are codon optimized for improved expression over the wild-type coding sequences. In some embodiments, the polynucleotide encoding IL-15 shares at least 90%, 91%, 92%, 93%, 94%, 95%, 96%, 97%, 98%, 99% or 100% sequence identity to SEQ ID NO:3 or SEQ ID NO:4. In some embodiments, the polynucleotide encoding IL-15Rα shares at least 90%, 91%, 92%, 93%, 94%, 95%, 96%, 97%, 98%, 99% or 100% sequence identity to SEQ ID NO:9 or SEQ ID NO: 11.

When expressed from a polynucleotide encoding IL-15, the coding sequence can have a native or a heterologous signal peptide. In some embodiments, the signal peptide is a native IL-15 signal peptide, for example, the native IL-15 long signal peptide or the native IL-15 short signal peptide. In some embodiments, the signal peptide is a heterologous signal peptide, for example, a signal peptide from granulocyte-macrophage colony stimulating factor (GM-CSF), tissue plasminogen activator (tPA), growth hormone, or an immunoglobulin.

In some embodiments, the peripheral tissue is a peripheral lymphoid tissue, including without limitation, spleen, lymph node, mucosal-associated lymphoid tissues (MALT), e.g., tonsils and/or gut-associated lymphoid tissues (GALT), including Peyer's patches.

In some embodiments, the peripheral tissue is a peripheral non-lymphoid tissue, e.g., lung, liver, kidney, heart, skin, etc.

Preferably, the IL-15 is administered without an antigen, i.e., is not co-administered with an antigen.

In a related aspect, the invention provides a DNA vector encoding IL-15 and IL-15Rα for use in promoting lymphocyte mobilization from central lymphoid tissue and migration to peripheral tissues.

In another aspect, the invention provides IL-15/IL-15Rα for use in promoting lymphocyte mobilization from central lymphoid tissue and migration to peripheral tissues.

In a related aspect, the invention provides a DNA vector encoding IL-15 and IL-15Rα for use in promoting the maturation and export of T cells from the thymus to peripheral tissues, including peripheral lymphoid and non-lymphoid tissues.

In another aspect, the invention provides IL-15/IL-15Rα polypeptide complexes for use in promoting the maturation and export of T cells from the thymus to peripheral tissues, including peripheral lymphoid and non-lymphoid tissues.

In a related aspect, the invention provides a DNA vector encoding IL-15 and IL-15Rα for use in promoting repopulation of depleted lymphocytes in peripheral tissues and/or preventing, reducing and/or inhibiting lymphopenia.

In another aspect, the invention provides IL-15/IL-15Rα polypeptide complexes for use in promoting repopulation of depleted lymphocytes in peripheral tissues and/or preventing, reducing and/or inhibiting lymphopenia.

In another aspect, the invention provides stable cell lines that express IL-15/IL-15Rα polypeptides. In some embodiments, the stable cell line expresses IL-15/IL-15Rα in the form of a fusion protein. In some embodiments, the stable cell lines produce IL-15 and IL-15Rα as different molecules. In some embodiments, the stable cell lines produce IL-15 and secreted IL-15Rα deletions that lack the transmembrane anchor portion of the receptor. In some embodiments the stable cell lines produce IL-15 and fusions of IL15Rα to the an immunoglobulin Fc region. In some embodiments the stable cell lines produce IL-15 and IL-15Rα fusions to polypeptides able to direct binding of the fusion to the cell surface of specific cell types. In some embodiments the stable cell lines produce IL-15 and IL-15Rα fusions to polypeptides able to direct multimerization of the fusion.

Further embodiments are as described herein.

Definitions

The term "central lymphoid tissue" or "central lymphoid organ" refers to specialized lymphoid tissues where the production of new lymphocytes, or lymphopoiesis, takes place. For example, T cells develop and mature in the thymus or thymic tissue. B cells and natural killer (NK) cells develop in bone marrow tissue. See, e.g., Chapter 7 of Janeway, et al., *Immunobiology,* 2001, Garland Publishing, New York.

The term "peripheral lymphoid tissue" or "peripheral lymphoid organ" refers to peripheral tissues of highly organized architecture, with distinct areas of B cells and T cells. Newly produced lymphocytes leave the central lymphoid tissues, and are carried in the blood to the peripheral lymphoid tissues. Exemplary peripheral lymphoid tissues or organs include the spleen, lymph nodes, mucosal-associated lymphoid tissues (MALT), e.g., tonsils and gut-associated lymphoid tissues (GALT), including Peyer's patches.

The term "mature lymphocyte" refers to a lymphocyte that is undergone selection and development to maturity in the central lymphoid tissue sufficient to circulate to peripheral lymphoid tissues. With respect to T cells, a mature T cell is characterized by the expression of either CD4 or CD8, but not both (i.e., they are single positive), and expression of CD3. With respect to B cells, a mature B cell is characterized by VDJ rearranged immunoglobulin heavy chain gene, VJ rearranged immunoglobulin light chain gene, and the surface expression of IgD and/or IgM. The mature B cell may also express CD19 and the IL-7 receptor on the cell surface.

The term "activated lymphocyte" refers to lymphocytes that have recognized an antigen bound to a MHC molecule and the simultaneous delivery of a co-stimulatory signal by a specialized antigen-presenting cell. Activation of lymphocytes changes the expression of several cell-surface molecules.

With respect to T cells, resting naive T cells express L-selectin, and low levels of other adhesion molecules such as CD2 and LFA-1. Upon activation of the T cell, expression of L-selectin is lost and, instead, increased amounts of the integrin VLA-4 are expressed. Activated T cells also express higher densities of the adhesion molecules CD2 and LFA-1, increasing the avidity of the interaction of the activated T cell with potential target cells, and higher densities of the adhesion molecule CD44. Finally, the isoform of the CD45 molecule expressed by activated cells changes, by alternative splicing of the RNA transcript of the CD45 gene, so that activated T cells express the CD45RO isoform that associates with the T-cell receptor and CD4. Also, with respect to cytokine production, resting T cells produce little or no IL-2 and the β and γ subunits of the IL-2 receptor. In contrast, activated T cells produce significant amounts IL-2 along with the α chain of the IL-2 receptor.

With respect to B cells, activated B cells have undergone isotype switching and secrete immunoglobulin. Naive B cells express cell-surface IgM and IgD immunoglobulin isotypes. In contrast, activated or memory B cells express and secrete IgG, IgA or IgE immunoglobulin isotypes.

The terms "output" or "migration" from a central lymphoid tissue refers to migration or export of mature lymphocytes from a central lymphocyte tissue to a peripheral tissue, including lymphoid and non-lymphoid peripheral tissues. Output includes the migration of mature T cells from the thymus and the migration of mature B cells and NK cells from the bone marrow.

The terms "treating" and "treatment" refer to delaying the onset of, retarding or reversing the progress of, or alleviating or preventing either the disease or condition to which the term applies, or one or more symptoms of such disease or condition.

The terms "lymphopenia" or "lymphocytopenia" or "lymphocytic leucopenia" interchangeably refer to an abnormally small number of lymphocytes in the circulating blood or in peripheral circulation. Quantitatively, lymphopenia can be described by various cutoffs. In some embodiments, a patient is suffering from lymphopenia when their circulating blood total lymphocyte count falls below about 600/mm$^3$. In some embodiments, a patient suffering from lymphopenia has less than about 2000/μL total circulating lymphocytes at birth, less than about 4500/μL total circulating lymphocytes at about age 9 months, or less than about 1000/μL total circulating lymphocytes patients older than about 9 months (children and adults). Lymphocytopenia has a wide range of possible causes, including viral (e.g., HIV infection), bacterial (e.g., active tuberculosis infection), and fungal infections; chronic failure of the right ventricle of the heart, Hodgkin's disease and cancers of the lymphatic system, leukemia, a leak or rupture in the thoracic duct, side effects of prescription medications including anticancer agents, antiviral agents, and glucocorticoids, malnutrition resulting from diets that are low in protein, radiation therapy, uremia, autoimmune disorders, immune deficiency syndromes, high stress levels, and trauma. Lymphopenia may also be of unknown etiology (i.e., idiopathic lymphopenia). Peripheral circulation of all types of lymphocytes or subpopulations of lymphocytes (e.g., CD4+ T cells) may be depleted or abnormally low in a patient suffering from lymphopenia. See, e.g., The Merck Manual, 18$^{th}$ Edition, 2006, Merck & Co.

The term "native mammalian interleukin-15 (IL-15)" refers to any naturally occurring interleukin-15 nucleic acid and amino acid sequences of the IL-15 from a mammalian species. Those of skill in the art will appreciate that interleukin-15 nucleic acid and amino acid sequences are publicly available in gene databases, for example, GenBank through the National Center for Biotechnological Information on the worldwide web at ncbi.nlm.nih.gov. Exemplified native mammalian IL-15 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-15 nucleic acid sequences include NM_172174.2 (human preproprotein); NM_172175 (human); NM_000585.3 (human preproprotein); U19843 (macaque); DQ021912 (macaque); AB000555 (macaque); NM_214390 (porcine); DQ152967 (ovine); NM_174090 (bovine); NM_008357 (murine); NM_013129 (rattus); DQ083522 (water buffalo); XM_844053 (canine); DQ157452 (lagomorpha); and NM_001009207 (feline). Accession numbers for exemplified native mammalian IL-15 amino acid sequences include NP_000576.1 (human preproprotein); NP_751914 (human preproprotein); CAG46804 (human); CAG46777 (human); AAB60398 (macaque); AAY45895 (macaque); NP_999555 (porcine); NP_776515 (bovine); AAY83832 (water buffalo); ABB02300 (ovine); XP_849146 (canine); NP_001009207 (feline); NP_037261 (rattus); and NP_032383 (murine).

The term "interleukin-15" or "IL-15" refers to a polypeptide that has at least 90%, 91%, 92%, 93%, 94%, 95%, 96%, 97%, 98% or 99% sequence identity to a native mammalian IL-15 amino acid sequence, or a nucleotide encoding such a polypeptide, is biologically active, meaning the mutated protein ("mutein") has functionality similar (75% or greater) to that of a native IL-15 protein in at least one functional assay. Functionally, IL-15 is a cytokine that regulates T cell and natural killer cell activation and proliferation. IL-15 and IL-2 share many biological activities, including binding to CD122, the IL-20/IL-1513 receptor subunit. The number of CD8+ memory cells is controlled by a balance between this IL-15 and IL-2. IL-15 induces the activation of JAK kinases, as well as the phosphorylation and activation of transcription activators STAT3, STAT5, and STAT6. IL-15 also increases the expression of apoptosis inhibitor BCL2L1/BCL-x(L), possibly through the transcription activation activity of STAT6, and thus prevents apoptosis. Two alternatively spliced transcript variants of the IL-15 gene encoding the same mature protein have been reported. Exemplified functional assays of an IL-15 polypeptide include proliferation of T-cells (see, for example, Montes, et al., *Clin Exp Immunol* (2005) 142:292), and activation of NK cells, macrophages and neutrophils. Methods for isolation of particular immune cell subpopulations and detection of proliferation (i.e., $^3$H-thymidine incorporation) are well known in the art. Cell-mediated cellular cytotoxicity assays can be used to measure NK cell, macrophage and neutrophil activation. Cell-mediated cellular cytotoxicity assays, including release of isotopes ($^{51}$Cr), dyes (e.g., tetrazolium, neutral red) or enzymes, are also well known in the art, with commercially available kits (Oxford Biomedical Research, Oxford, M; Cambrex, Walkersville, Md.; Invitrogen, Carlsbad, Calif.). IL-15 has also been shown to inhibit Fas mediated apoptosis (see, Demirci and Li, *Cell Mol Immunol* (2004) 1:123). Apoptosis assays, including for example, TUNEL assays and annexin V assays, are well known in the art with commercially available kits (R&D Systems, Minneapolis, Minn.). See also, Coligan, et al., Current Methods in Immunology, 1991-2006, John Wiley & Sons.

The term "native mammalian interleukin-15 Receptor alpha (IL15Rα)" refers to any naturally occurring interleukin-15 receptor alpha nucleic acid and amino acid sequences of the IL-15 receptor alpha from a mammalian species. Those of skill in the art will appreciate that interleukin-15 receptor alpha nucleic acid and amino acid sequences are publicly available in gene databases, for example, GenBank through the National Center for Biotechnological Information on the worldwide web at ncbi.nlm.nih.gov. Exemplified native mammalian IL-15 receptor alpha nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-15 nucleic acid sequences include NM_172200.1 (human isoform 2); and NM_002189.2 (human isoform 1 precursor). Accession numbers for exemplified native mammalian IL-15 amino acid sequences include NP_751950.1 (human isoform 2); and NP_002180.1 (human isoform 1 precursor).

The term "interleukin-15 receptor alpha" or "IL15Rα" refers to a polypeptide that has at least 90%, 91%, 92%, 93%, 94%, 95%, 96%, 97%, 98% or 99% sequence identity to a native mammalian IL15Rα amino acid sequence, or a nucleotide encoding such a polypeptide, is biologically active, meaning the mutated protein ("mutein") has functionality similar (75% or greater) to that of a native IL15Rα protein in at least one functional assay. IL15Rα is a cytokine receptor that specifically binds IL15 with high affinity. One functional assay is specific binding to a native IL-15 protein.

The term "soluble IL-15 Receptor alpha" or "sIL-15α" refers to forms of IL-15 Receptor alpha lacking the transmembrane anchor portion of the receptor and thus able to be secreted out of the cell without being anchored to the plasma membrane. Exemplary sIL-15α include aa 31-205 and aa31-185 of the native IL-15 Receptor alpha.

An "IL-15Rα Fc fusion" or an "IL-15Rα fused to an Fc region" as used herein refers to forms of IL-15Rα in which the protein is fused to one or more domains of an Fc region of an immunoglobulin, typically of an IgG immunoglobulin. The Fc region comprises the CH2 and CH3 domains of the IgG heavy chain and the hinge region. The hinge serves as a flexible spacer between the two parts of the Fc-Fusion protein, allowing each part of the molecule to function independently. The use of Fc fusions is known in the art (see, e.g., U.S. Pat. Nos. 7,754,855; 5,480,981; 5,808,029; Wo7/23614; Wo98/28427 and references cited therein. Fc fusion proteins can include variant Fc molecules (e.g., as described in U.S. Pat. No. 7,732,570). Fc fusion proteins can be soluble in the plasma or can associate to the cell surface of cells having specific Fc receptors.

The term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Degenerate codon substitutions for naturally occurring amino acids are in Table 1.

TABLE 1

| 1st position | 2nd position | | | | 3rd position |
|---|---|---|---|---|---|
| (5' end) | U(T) | C | A | G | (3' end) |
| U(T) | Phe | Ser | Tyr | Cys | U(T) |
|  | Phe | Ser | Tyr | Cys | C |
|  | Leu | Ser | STOP | STOP | A |
|  | Leu | Ser | STOP | Trp | G |
| C | Leu | Pro | His | Arg | U(T) |
|  | Leu | Pro | His | Arg | C |
|  | Leu | Pro | Gln | Arg | A |
|  | Leu | Pro | Gln | Arg | G |
| A | Ile | Thr | Asn | Ser | U(T) |
|  | Ile | Thr | Asn | Ser | C |
|  | Ile | Thr | Lys | Arg | A |
|  | Met | Thr | Lys | Arg | G |
| G | Val | Ala | Asp | Gly | U(T) |
|  | Val | Ala | Asp | Gly | C |
|  | Val | Ala | Glu | Gly | A |
|  | Val | Ala | Glu | Gly | G |

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., of a IL-15 or IL-15Rα sequence), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of am amino acid or nucleic acid sequences.

For sequence comparison, typically one sequence acts as a reference sequence, to which test sequences are compared (here, an entire "native mammalian" IL-15 amino acid or nucleic acid sequence). When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithm that is suitable for determining percent sequence identity and sequence similarity are the BLAST algorithms, which are described in Altschul et al., *Nuc. Acids Res.* 25:3389-3402 (1977) and Altschul et al., *J. Mol. Biol.* 215:403-410 (1990), respectively. BLAST software is publicly available through the National Center for Biotechnology Information on the worldwide web at ncbi.nlm.nih.gov/. Both default parameters or other non-default parameters can be used. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The term "GC content" refers to the percentage of a nucleic acid sequence comprised of deoxyguanosine (G) and/or deoxycytidine (C) deoxyribonucleosides, or guanosine (G) and/or cytidine (C) ribonucleoside residues.

The term "operably linked" refers to a functional linkage between a first nucleic acid sequence and a second nucleic acid sequence, such that the first and second nucleic acid sequences are transcribed into a single nucleic acid sequence. Operably linked nucleic acid sequences need not be physically adjacent to each other. The term "operably linked" also refers to a functional linkage between a nucleic acid expression control sequence (such as a promoter, or array of transcription factor binding sites) and a transcribable nucleic acid sequence, wherein the expression control sequence directs transcription of the nucleic acid corresponding to the transcribable sequence.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The terms "mammal" or "mammalian" refer to any animal within the taxonomic classification mammalia. A mammal can refer to a human or a non-human primate. A mammal can refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

The term "therapeutically effective amount" refers to the dose of a therapeutic agent or agents sufficient to achieve the intended therapeutic effect with minimal or no undesirable side effects. A therapeutically effective amount can be readily determined by a skilled physician, e.g., by first administering a low dose of the pharmacological agent(s) and then incrementally increasing the dose until the desired therapeutic effect is achieved with minimal or no undesirable side effects.

The term "suprahysiologic levels" refers to levels of IL-15 in a particular tissue, e.g., blood, plasma, serum, thymus, that are above naturally occurring physiologic levels. Suprahysiologic levels of IL-15 in a tissue can also be achieved when the concentration of IL-15 in that tissue is sustained above naturally occurring levels for an extended period of time, e.g., for consecutive days or weeks or for the duration of therapeutic treatment. For example, IL-15 DNA or protein can be administered at a dose sufficient to achieve plasma levels of IL-15 of about 1 to 1000 ng/ml, for example, plasma levels of IL-15 of about 10 to 1000 ng/ml. The IL-15 and IL-15Rα can be delivered in equimolar amounts. Alternatively, an IL-15/IL-15Rα protein complex can be administered at a dose of about 0.01 to 0.5 mg/kg.

The term "co-administer" refers to the presence of two pharmacological agents, e.g., IL-15 and IL-15Rα, in the blood at the same time. The two pharmacological agents can be administered concurrently or sequentially.

The term "consisting essentially of" refers to administration of the pharmacologically active agents expressly recited, e.g., IL-15 and IL-15R, and excludes pharmacologically active agents not expressly recited, e.g., an antigen. The term consisting essentially of does not exclude pharmacologically inactive or inert agents, e.g., physiologically acceptable carriers or excipients.

DETAILED DESCRIPTION

1. Introduction

Figure 1:
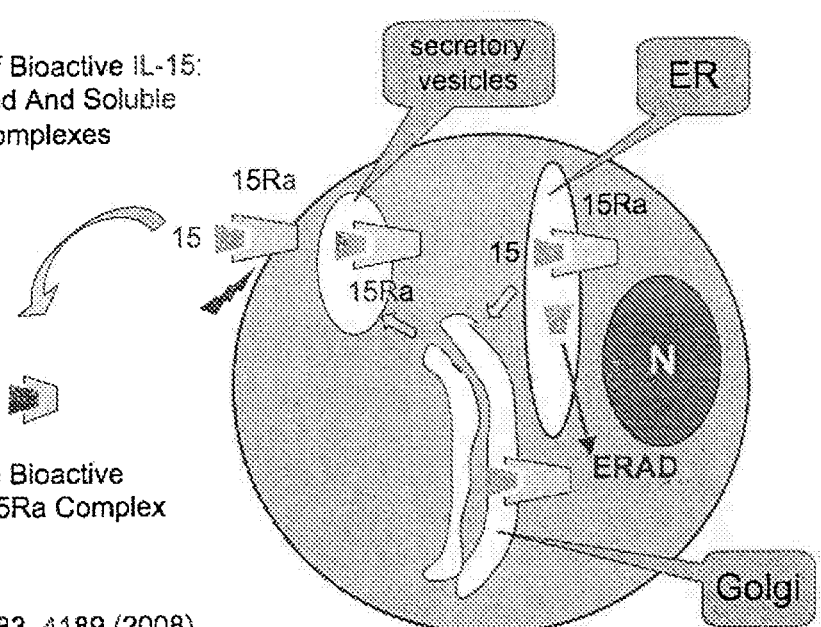
FIG. 1 illustrates a schematic of the mutual stabilization of IL-15 and IL-15.

The present invention is based, in part, on the surprising discovery that subjecting thymic tissue to suprahysiological levels of IL-15 promotes the maturation of T cells in the thymus from double positive CD4+CD8+ T cells to single positive (i.e., CD4+ or CD8+) CD3high T cells, decreases the frequency of apoptotic thymocytes, and increases the migration of mature T cells from the thymus to peripheral tissues, including lymphoid and non-lymphoid peripheral tissues.

The present invention is further based, in part, on the surprising discovery that systemic administration of suprahysiological levels of IL-15 promotes the maturation and export of lymphocytes from central lymphoid tissues (e.g., in the thymus and bone marrow) to peripheral tissues, including lymphoid and non-lymphoid peripheral tissues.

2. Methods of Promoting Maturation of Lymphocytes in a Central Lymphoid Organ and the Migration of the Lymphocytes to Peripheral Tissues The present invention provides methods of promoting T cell maturation in the thymus, decreasing apoptosis of T cells in the thymus and promoting migration or output of mature T cells from the thymus, by contacting the thymus tissue with supraphysiological levels of IL-15. The thymic tissue can be in vivo or in vitro.

When the IL-15 is administered in vivo, it is provided to a subject or patient or individual in need thereof. The subject can be any mammal. In some embodiments, the mammal is a human or a non-human primate. Subjects who will benefit from the present methods have a deficiency of mature thymocytes and/or other lymphocytes in peripheral tissues, including lymphoid and non-lymphoid peripheral tissues. In some embodiments, the subject is immunodeficient or has lymphopenia. In some embodiments, the subject has a drug-induced immunodeficiency, e.g., due to anticancer drugs. In some embodiments, the subject has an immunodeficiency secondary to a disease, e.g., HIV infection. In some embodiments, the subject may have a genetic mutation that results in a non-functional IL-15 or non-functional IL-15 receptor subunit (e.g., IL-15Rα, IL-15Rβ, or IL-15Rγ).

Sustained exposure of thymic tissue to supraphysiological levels of IL-15 promotes the maturation of double positive T cells. IL-15 promotes the terminal differentiation of the thymocytes to single positive T cells expressing either CD4 or CD8. The mature T cells also may express CD122 (also known as the beta subunit of IL-2/IL-15 receptor). The mature T cells may also express high levels of the CD3 surface protein. IL-15-induced maturation of T cells also corresponds to a reduction in the frequency of immature T cells that undergo apoptosis. By contacting the thymic tissue with supraphysiologic levels of IL-15, the CD4+CD8+ double positive and CD3low T cells can be substantially eliminated as the cells mature into single positive CD3high T cells. After exposure to supraphysiologic levels of IL-15, at least 60%, 70%, 80%, 90%, 95% or more of the T cells are CD4+ or CD8+ single positive CD3high T cells.

IL-15-induced maturation of T cells in thymus tissue also promotes the migration of the mature T cells to the peripheral tissues, including lymphoid and non-lymphoid peripheral tissues. The mature T cells leaving the thymus may or may not be activated. For example, after about 2, 3, 4, 5, 6, 7, 8, 9, 10 or more days exposure to supraphysiologic levels of IL-15, the thymus organ may have decreased in size, e.g., by at least about 30%, 40%, 50%, or more, due to IL-15-induced thymic output.

Systemic administration of supraphysiologic levels of IL-15, e.g., sustained over the course of e.g., about 2, 3, 4, 5, 6, 7, 8, 9, 10 or more days, also promotes the maturation and migration of lymphocytes, including NK cells, from bone marrow. For example, after about 2, 3, 4, 5, 6, 7, 8, 9, 10 or more days exposure to supraphysiologic levels of IL-15, the percentage of lymphocytes in the bone marrow may have decreased, e.g., by at least about 50%, 60%, 70%, 80%, or more, due to IL-15-induced lymphocyte output from bone marrow.

At the same time that the number of lymphocytes decrease in the central lymphoid tissues, i.e., in the thymus and bone marrow, the number of lymphocytes in peripheral lymphoid tissues, e.g., spleen, lymph node, mucosal-associated lymphoid tissues (MALT), e.g., tonsils and/or gut-associated lymphoid tissues (GALT), including Peyer's patches, increases. Furthermore, the number of lymphocytes in peripheral non-lymphoid tissues, including the lung, liver, kidney, skin, and other tissues, also increases. In some embodiments, the administration of supraphysiologic levels of IL-15 increases the number of lymphocytes, including T cells, B cells and NK cells, in the blood.

3. Methods of Treating Lymphopenia

As explained above, in one aspect, the invention is based on the discovery that systemic administration of supraphysiological levels of IL-15 promotes the maturation and export of lymphocytes from central lymphoid tissues (e.g., in the thymus and bone marrow) to peripheral tissues, including lymphoid and non-lymphoid peripheral tissues.

Accordingly, the invention provides methods for preventing, reducing and inhibiting the depletion of lymphocytes, including T cells, B cells and natural killer (NK) cells, in peripheral circulation or tissues by systemic administration of IL-15 to a subject in need thereof. The present invention also provides methods for accelerating the recovery from and shortening the time period of depletion of lymphocytes, including T cells, B cells and natural killer (NK) cells, in peripheral circulation or tissues by systemic administration of IL-15 to a subject in need thereof.

The subject, patient or individual can be any mammal. In some embodiments, the mammal is a human or a non-human primate. In some embodiments, the individual is a domestic mammal (e.g., a canine or feline), a laboratory mammal (e.g., a mouse, a rat, a rabbit, a hamster), or an agricultural mammal (e.g., a bovine, a porcine, a ovine, an equine). Subjects who will benefit from the present methods either already have or will have (e.g., as a result of a course of drug treatment) a deficiency of mature lymphocytes in peripheral circulation or tissues, including lymphoid and non-lymphoid peripheral tissues. In some embodiments, the subject is immunodeficient or has lymphopenia. For the purposes of treatment, the patient is already suffering abnormally low levels of circulating lymphocytes. For the purposes of prevention, the patient may have normal levels of peripheral lymphocytes and is likely to experience lymphodepletion, e.g., as a result of a chemotherapeutic treatment.

Standards for diagnosing lymphopenia are known in the art, and can be made by any trained physician. In some embodiments, the patient has a circulating blood total lymphocyte count that is below about 600/mm$^3$. In some embodiments, the patient has a circulating blood total lymphocyte count that is less than about 2000/μL total circulating lymphocytes at birth, less than about 4500/μL total circulating lymphocytes at about age 9 months, or less than about 1000/μL total circulating lymphocytes patients older than about 9 months (children and adults). See, e.g., The Merck Manual, 18th Edition, 2006, Merck & Co.

The origins or etiology of the depletion or abnormally low can be for any reason. Lymphocytopenia has a wide range of possible causes, including viral (e.g., HIV infection), bacterial (e.g., active tuberculosis infection), and fungal infections; chronic failure of the right ventricle of the heart, Hodgkin's disease and cancers of the lymphatic system, leukemia, a leak or rupture in the thoracic duct, side effects of prescription medications including anticancer agents, antiviral agents, and glucocorticoids, malnutrition resulting from diets that are low in protein, radiation therapy, uremia, autoimmune disorders, immune deficiency syndromes, high stress levels, and trauma. The lymphopenia may also be of unknown etiology (i.e., idiopathic lymphopenia).

The lymphocyte depletion may involve total lymphocytes (e.g., T cells, B cells, and NK cells, etc.), or may only involve a subpopulation of total lymphocytes (one or more of T cells, CD4+ T cells, CD8+ T cells, B cells, NK cells).

In some embodiments, the patient has a disease that causes depletion of peripheral circulating lymphocytes. For example, the patient may suffer from a cancer, including Hodgkin's disease and cancers of the lymphatic system, leukemia; a viral infection, including HIV or hepatitis virus. In some embodiments, the patient is receiving chemotherapy, e.g., an anticancer agent, an antiviral or antiretroviral agent, or a glucocorticoid, that causes depletion of peripheral circulating lymphocytes. Exemplary pharmacological agents that can cause lymphodepletion include without limitation vinblastine, fludarabine, aclarubicin, doxorubicin, exemestane, alefacept, alemtuzumab, chloramphenicol, pamidronate, idarubicin and cyclophosphamide.

In some embodiments, the subject may have a genetic mutation that results in a non-functional IL-15 or non-functional IL-15 receptor subunit (e.g., IL 15Rα, IL 15Rβ, or IL 15Rγ).

4. IL-15

The IL-15 for use in the invention can be any physiologically active (i.e., functional) IL-15. The IL-15 can be delivered as a polypeptide or a polynucleotide encoding IL-15. The IL-15 can be full-length or a physiologically active fragment thereof, for example, an IL-15 fragment that retains binding to IL-15Rα and/or IL-15Rβ, or an IL-15 fragment that promotes proliferation and/or maturation of T cells. In some embodiments, the delivered or expressed IL-15 polypeptide has one or more amino acids that are substituted, added or deleted, while still retaining the physiological activity of IL-15. In some embodiments, the delivered or expressed IL-15 shares at least 90%, 93%, 95%, 97%, 98%, 99% or 100% amino acid sequence identity with a wild-type IL-15, e.g., SEQ ID NO:2. In some embodiments, the polynucleotide encoding IL-15 shares at least 90%, 93%, 95%, 97%, 98%, 99% or 100% nucleic acid sequence identity with a wild-type IL-15 coding sequence, e.g., SEQ ID NO: 1.

The polynucleotide encoding IL-15 may have one or more codons altered for improved expression. In some embodiments, the polynucleotide encoding IL-15 shares at least 90%, 93%, 95%, 97%, 98%, 99% or 100% nucleic acid sequence identity with a wild-type IL-15 coding sequence, e.g., SEQ ID NO:3. In some embodiments, the polynucleotide encoding IL-15 shares at least 96%, 97%, 98%, 99% or 100% nucleic acid sequence identity with a wild-type IL-15 coding sequence, e.g., SEQ ID NO:4. Polynucleotides encoding IL-15 which have altered codons for improved expression are described, e.g., in WO 2007/084342 and in WO 2004/059556, the entire disclosures of each of which are hereby incorporated herein by reference for all purposes.

The polynucleotide encoding IL-15 can be operably linked to polynucleotide encoding a native signal peptide sequence, e.g., the long IL-15 signal peptide sequence (LSP) or the short IL-15 signal peptide sequence (SSP). In some embodiments, the nucleic acid sequence encoding a native IL-15 signal peptide is replaced with a nucleic acid sequence encoding a signal peptide from a heterologous protein. The heterologous protein can be, for example, from tissue plasminogen activator (tPA), growth hormone, granulocyte-macrophage colony stimulating factor (GM-CSF) or an immunoglobulin (e.g., IgE). An example of a human GMCSF-IL-15 fusion is provided in SEQ ID NO: 18. In some embodiments, the nucleic acid encoding the IL-15 is operably linked to a nucleic acid encoding an RNA export element, for example a CTE or RTEm26CTE.

Preferably, the IL-15 is administered as a heterodimer with IL-15Rα. One or both of the IL-15 and the IL-15Rα can be delivered as a polypeptide. One or both of the IL-15 and the IL-15Rα can be delivered as a polynucleotide. In one embodiment, the IL-15 and the IL-15Rα are co-administered as polypeptides. In one embodiment, an IL-15 polypeptide is co-administered with a polynucleotide encoding IL-15Rα. In one embodiment, an IL-15Rα polypeptide is co-administered with a polynucleotide encoding IL-15.

The administered IL-15Rα can be any physiologically active (i.e., functional) IL-15Rα. The IL-15Rα can be delivered as a polypeptide or a polynucleotide encoding IL-15Rα. The IL-15Rα can be full-length or a physiologically active fragment thereof, for example, an IL-15Rα fragment that retains specific binding to IL-15. Further, the IL-15Rα, e.g., a fragment that retains specific binding to IL-15 and lacks the transmembrane anchor region, can be fused to an Fc region. In some embodiments, the delivered or expressed IL-15Rα polypeptide has one or more amino acids that are substituted, added or deleted, while still retaining the physiological activity of IL-15Rα. In some embodiments, the delivered or expressed IL-15 shares at least 90%, 93%, 95%, 97%, 98%, 99% or 100% amino acid sequence identity with a wild-type IL-15Rα, e.g., SEQ ID NO:5 or SEQ ID NO:7. In some embodiments, the polynucleotide encoding IL-15 shares at least 90%, 93%, 95%, 97%, 98%, 99% or 100% nucleic acid sequence identity with a wild-type IL-15 coding sequence, e.g., SEQ ID NO:6 or SEQ ID NO:8.

The polynucleotide encoding IL-15Rα may have one or more codons altered for improved expression. In some embodiments, the polynucleotide encoding IL-15Rα shares at least 90%, 93%, 95%, 97%, 98%, 99% or 100% nucleic acid sequence identity with a wild-type IL-15Rα coding sequence, e.g., SEQ ID NO:9 or SEQ ID NO: 11. Polynucleotides encoding IL-15Rα which have altered codons for improved expression are described, e.g., in WO 2007/084342.

The polynucleotide encoding IL-15Rα can be operably linked to polynucleotide encoding a native signal peptide sequence. In some embodiments, the nucleic acid sequence encoding a native IL-15Rα signal peptide is replaced with a nucleic acid sequence encoding a signal peptide from a heterologous protein. The heterologous protein can be, for example, from tissue plasminogen activator (tPA), growth hormone, granulocyte-macrophage colony stimulating factor (GM-CSF) or an immunoglobulin (e.g., IgE). In some embodiments, the nucleic acid encoding the IL-15Rα is operably linked to a nucleic acid encoding an RNA export element, for example a CTE or RTEm26CTE.

In some embodiments, the IL-15Rα can be in the form of an Fc fusion protein. Examples of sIL-15Rα polypeptide sequences are shown in SEQ ID NO: 17 and SEQ ID NO:20. Typically, such proteins are secreted and can be found soluble in the plasma, or they can be associated with the surface of cells expressing the Fc receptor for the Fc region of the fusion protein. Different fragments of IL-15Rα can be fused to the Fc region. Two examples of functional fusions are provided as SEQ ID NO: 17 and SEQ ID NO:20, containing 205 or 200 amino acids within the IL-15Rα region. In some embodiments, the IL-15Rα region of the fusion protein can be released by proteolytic cleavage. In some embodiments, I-L15Rα functional region of the protein is linked to a polypeptide that is able to bind specific cell types via surface receptors. In some embodiments, the IL15-Rα Fc fusion protein shares at least 95%, 96%, 97%, 98%, 99% or 100% amino acid sequence identity with a polypeptide selected from the group consisting of SEQ ID NO:17 and SEQ ID NO:20.

In some embodiments, a polynucleotide encoding IL-15 is co-administered with a polynucleotide encoding IL-15Rα. The polynucleotide encoding IL-15 and the polynucleotide encoding IL-15Rα can be administered on the same vector or on separate vectors. Preferably the polynucleotide encoding IL-15 is co-administered with a polynucleotide encoding IL-15Rα are on the same vector. An example of a plasmid that encodes an IL-15Rα-Fc fusion having a polypeptide sequence of SEQ ID NO:17 and a human GM-CSF signal peptide-IL-15 of SEQ ID NO:18 is provided in SEQ ID NO:16. A second example of a plasmid that encodes an IL-15Rα-Fc fusion having a polypeptide sequence of SEQ ID NO:20 and a human GM-CSF signal peptide-IL-15 of SEQ ID NO: 18 is provided in SEQ ID NO: 19. In some embodiments, the administered vector shares at least 95%, 97%, 98%, 99% or 100% nucleic acid sequence identity with a plasmid vector selected from the group consisting of SEQ ID NO: 13, SEQ ID NO: 14, SEQ ID NO: 15, SEQ ID NO:16, and SEQ ID NO: 19.

It is understood by one skilled in the art that expression vectors, promoters, polyadenylation signals, and secretory peptides alternatives to those in the example sequences provided herein can be used for the expression of the optimized IL-15 and IL-15 Receptor alpha.

For the purposes of the present methods, the IL-15 is not being used as an adjuvant to enhance the immune response against a particular antigen. Therefore, in the present methods, the IL-15 is administered without an antigen. Stated another way, the IL-15 is not co-administered with an antigen.

The IL-15 (and the IL-15Rα) are administered at a dose sufficient to achieve supraphysiological levels of IL-15 systemically or in the target tissue, e.g., thymus, for the desired time period. The desired time period can be hours, days, weeks, or longer if necessary. In some embodiments, supraphysiological levels of IL-15 are sustained throughout the duration of treatment or until a desired therapeutic endpoint is achieved, e.g., the repopulation of peripheral tissues with lymphocytes. In some embodiments, the IL-15 is administered one time, as a bolus. In some embodiments, the IL-15 is administered two or more times. When administered multiple times, the IL-15 can be administered daily, weekly, bi-weekly, monthly, or as needed to sustain supraphysiological levels of IL-15 systemically or in the target tissue.

In embodiments where the IL-15 (and the IL-15Rα) are administered as a polypeptide, typical dosages can range from about 0.1 mg/kg body weight up to and including about 0.5 mg/kg body weight. In some embodiments, the dose of polypeptide is about 0.01, 0.02, 0.05, 0.08, 0.1, 0.2, 0.3, 0.4, 0.5 mg/kg body weight.

In embodiments where the IL-15 (and the IL-15Rα) are administered as a polynucleotide, dosages are sufficient to achieve plasma levels of IL-15 of about 1 to 1000 ng/ml, for example, plasma levels of IL-15 of about 10 to 1000 ng/ml. Such a range of plasma concentrations can be achieved, e.g., after intramuscular electroporation of about 0.1 mg IL-15/IL-15sRα expressing DNA plasmid per kg body weight. In some embodiments, the dose of nucleic acid is about 0.02, 0.05, 0.1, 0.2, 0.5 mg/kg body weight.

The IL-15 can be administered by a route appropriate to effect systemic supraphysiological levels of IL-15 or supraphysiological levels of IL-15 in the target tissue, e.g., thymus. When co-administered with IL-15Rα, the IL-15 and the IL-15Rα can be administered via the same or different routes. In some embodiments, the IL-15 (and the IL-15Rα) are administered systemically, including without limitation, enterally (i.e., orally) or parenterally, e.g., intravenously, intramuscularly, subcutaneously, intradermally, intranasally, or inhalationally. In some embodiments, the IL-15 (and the IL-15Rα) are administered locally, for example, intrathymically or directly into the bone marrow.

For treatment of lymphopenia, systemic administration of IL-15 promotes and accelerates the repopulation of peripheral lymphocyte populations. After administration of IL-15, the peripherally circulating lymphocytes or lymphocyte subpopulations can be at least 80%, 85%, 90% or 95% of levels considered to be normal in a healthy individual. In some embodiments, the lymphocytes or lymphocyte subpopulations are completely repopulated to normal levels. In some embodiments, the repopulation of lymphocytes is days or weeks faster in an individual who received administration of IL-15 in comparison to an individual who did not receive administration of IL-15.

Systemic administration of IL-15 also prevents, reduces or inhibits lymphocyte depletion in peripheral circulation, e.g., caused by chemotherapy or radiation therapy. After administration of IL-15, the peripherally circulating lymphocytes or lymphocyte subpopulations can be maintained at levels of at least 70%, 75%, 80%, 85%, 90% or 95% of normal levels. In some embodiments, the lymphocytes or lymphocyte subpopulations are maintained at normal levels.

In some embodiments, the IL-15 is co-administered with a chemotherapeutic agent that causes or may cause lymphopenia or lymphocyte depletion in peripheral tissues. The chemotherapeutic agent may be an anticancer agent or an antiviral agent. In some embodiments, the IL-15 is administered after a course of treatment with a chemotherapeutic agent that causes or may cause lymphopenia or lymphocyte depletion in peripheral tissues. In some embodiments, the IL-15 is administered prior to, during or after a course of radiation therapy.

EXAMPLES

The following examples are offered to illustrate, but not to limit the claimed invention.

Figure 2:
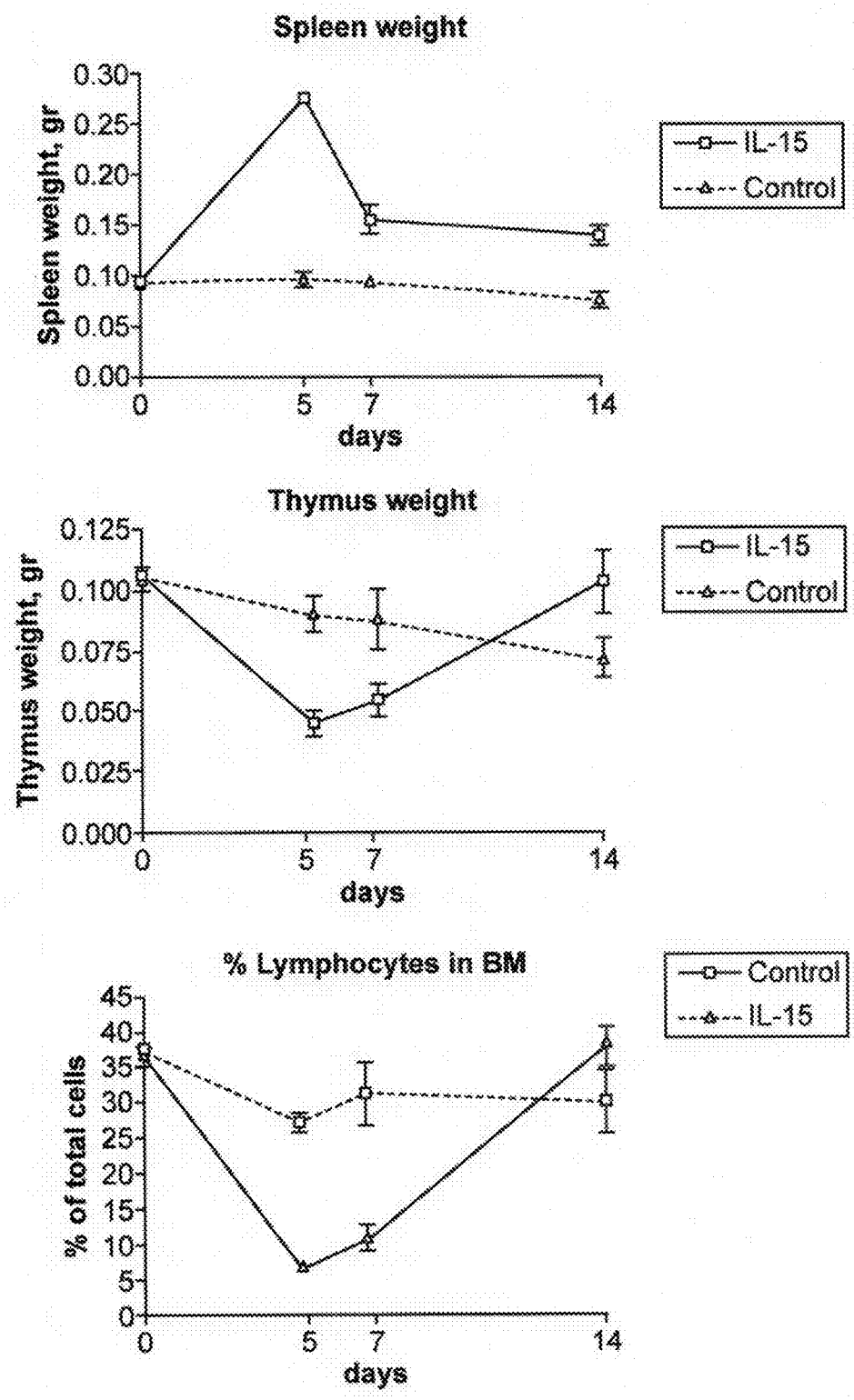
FIG. 2 illustrates the effects of systemic co-administration of polynucleotides expressing IL-15 and IL-15Rα on spleen weight (top panel), thymus weight (middle panel) and percentage of lymphocytes in the bone marrow (bottom panel).
Figure 3:
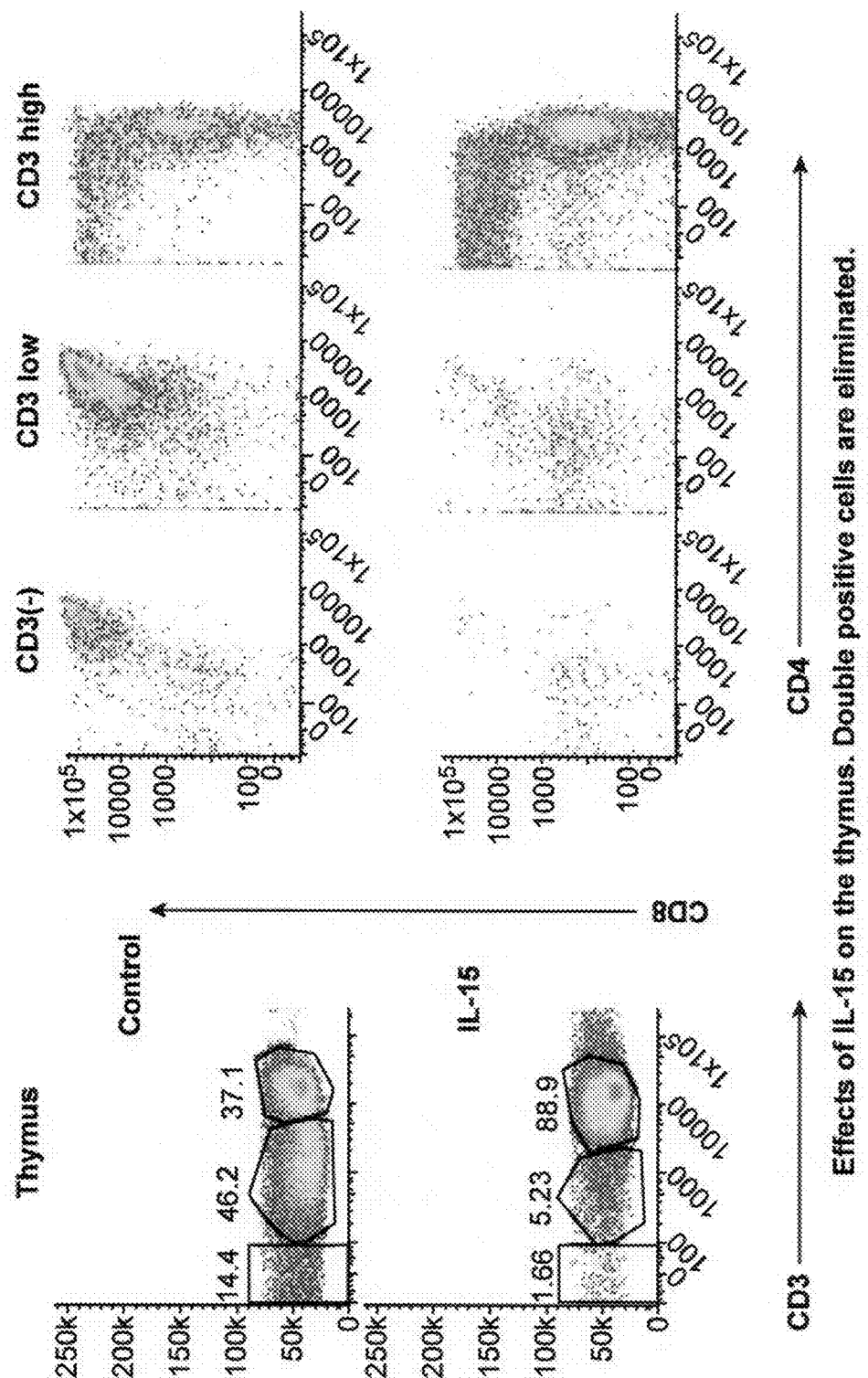
FIG. 3 illustrates the effects of systemic co-administration of polynucleotides expressing IL-15 and IL-15Rα on T cell maturation in the thymus. Double positive CD4+CD8+ T cells are decreased with a concomitant increase in CD3high single positive T cells (i.e., CD4+ or CD8+ T cells).
Figure 4:
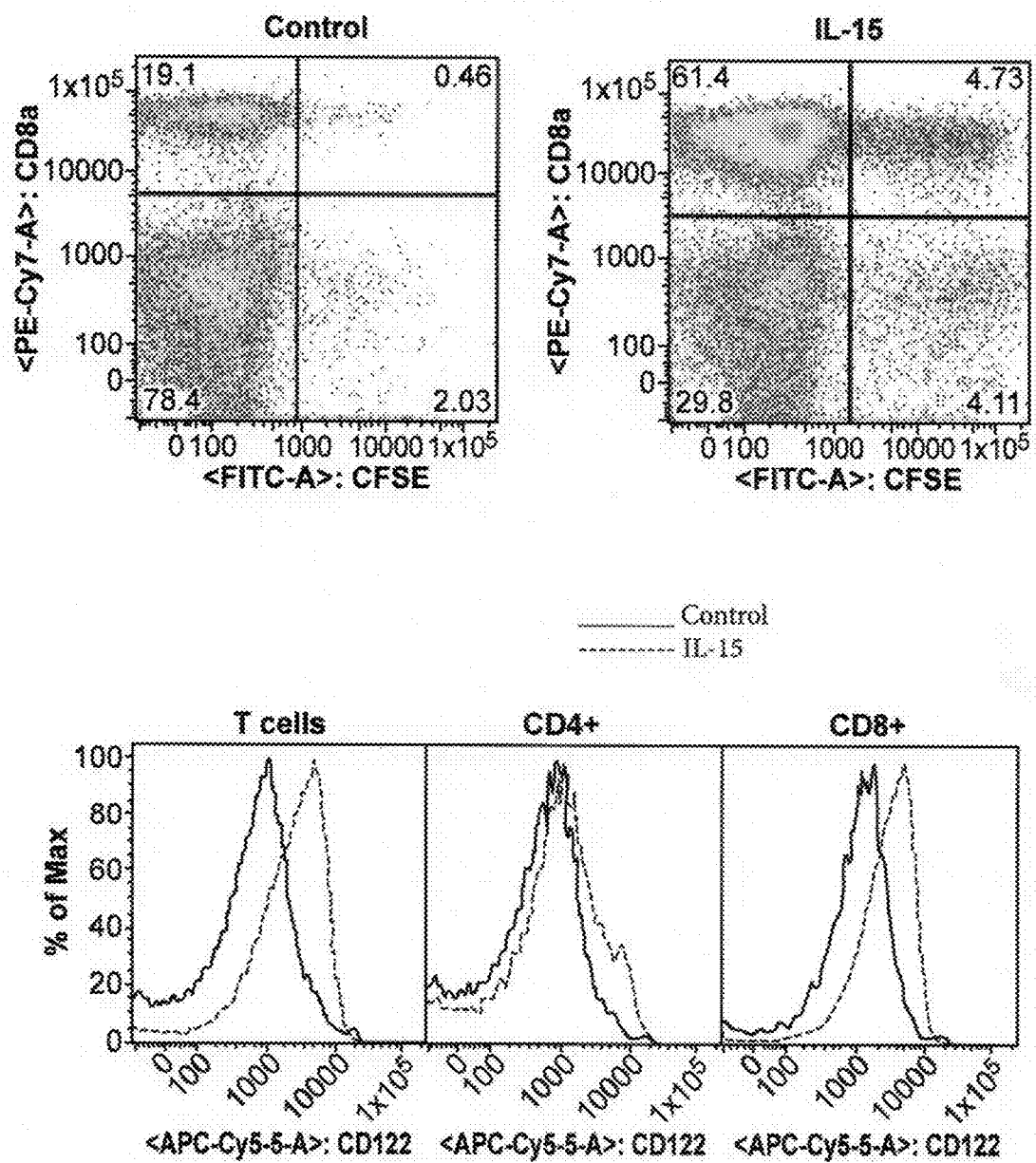
FIG. 4 illustrates the migration of dividing carboxyfluorescein succinimidyl ester ("CFSE")-loaded thymocytes to the lung in IL-15-treated and untreated control mice (upper panels). The lower panels show increased expression of CD122 (IL-2Rβ/IL-15Rβ) on lymphocytes, e.g., total T cells and CD+ T cells, in the lung.

Example 1: Systemic Administration of IL-15 Promotes Maturation of T Cells in the Thymus and the Migration of T Cells to Peripheral Tissues IL-15/IL-15Rα DNA was expressed systemically and locally at various levels in either normal or IL-15 knockout (KO) mice to further understand IL-15 biology. See, Bergamaschi, et al., (2008) *J Biol Chem* 283:4189-4199. Supraphysiologic levels of IL-15/IL-15Rα in normal mice have rapid and profound effects in many tissues. There is a rapid and reversible increase in the size of spleen, whereas the thymus becomes smaller and bone marrow lymphocyte numbers decrease (FIG. 2). We have previously shown that spleen and lymph node size increase is proportional to the amount of IL-15 in the plasma. See, Bergamaschi, et al., (2008) *J Biol Chem* 283:4189-4199. The kinetics and composition of lymphocytes in many tissues were studied using 10 parameter flow cytometry, as well as adoptive transfer of cells and in vivo labeling. Our results underscore the strong effects of IL-15 at all steps of lymphocyte development, as also suggested by many investigators. Reviewed in, e.g., Boyman, et al., (2007) *Curr Opin Immunol* 19:320-326: Sprent, et al., (2008) *Immunol Cell Biol* 86:312-319; Sprent and Surh, (2003) *Immunol Lett* 85:145-149; Surh, et al., (2006) *Immunol Rev* 211:154-163; Surh and Sprent, (2005) *Semin Immunol* 17:183-191; and Surh and Sprent, (2008) *Immunity* 29:848-862. However, prior to the present invention, the effects of IL-15 in the thymus have not been elucidated. Our results indicate that IL-15 stimulates the maturation of CD4+CD8+ double positive thymocytes into CD3high single positive T cells (FIG. 3) and accelerates their rapid migration to the periphery (FIG. 4). Seven days after in situ labeling of thymocytes, IL-15/IL-15Rα promoted their migration to the lung. In the presence of IL-15/IL-15Rα the lymphocytes in the lung have higher levels of IL-2/IL-15Rα (CD122, see, FIG. 4, bottom) indicating that they are activated. These results are consistent with the notion that IL-15 promotes not only accelerated exit from the thymus, but also the migration to peripheral tissues and the activation of these lymphocytes.

Our results also show that, in addition to NK and memory CD8+ T cells that are profoundly affected, as expected, all lymphocytes including naïve and memory CD4 and CD8 cells, and B lymphocytes are also affected to either divide, migrate or be activated. This is in agreement with the widespread (but not universal) expression of the IL-2/IL-15 betagamma receptor. The hierarchy of responsiveness of the lymphocyte subsets to IL-15 reflects the levels of CD122 (IL-2Rbeta) on their surface. See, Bergamaschi, et al., (2008) *J Biol Chem* 283:4189-4199.

Figure 5:
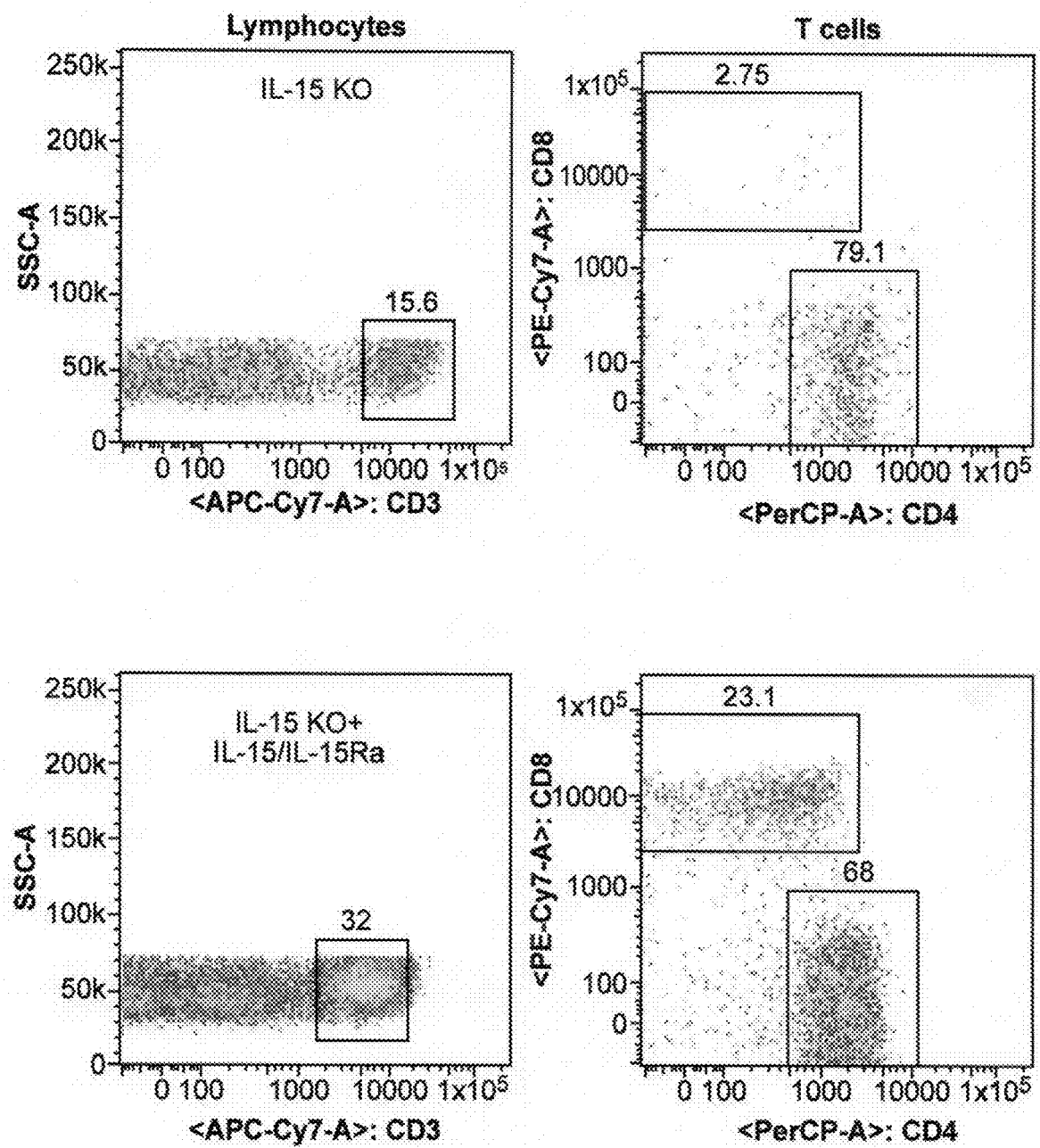
FIG. 5 illustrates lymphocyte reconstitution in lung tissue of IL-15 knock-out (KO) mice treated with plasmid DNA encoding IL-15/IL-15Rα compared to untreated control KO mice.
Figure 6:
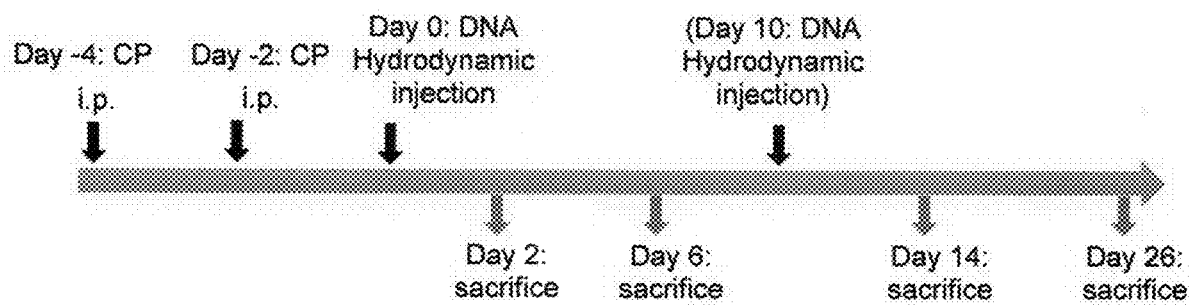
FIG. 6 provides a schematic of the time course of a lymphodepletion experiment.

Our observations are further supported by experiments performed in an IL-15 KO model, to correct the lymphocyte defects by administering plasmid DNA encoding IL-15/IL-15Rα heterodimer. IL-15 KO mice are characterized by a decrease in total T cell count that preferentially affects CD8+ T cells, which are almost completely absent in peripheral tissues. We show that IL-15/IL-15Rα is able to repopulate non-lymphoid organs, such as lungs, with both mature CD4 and CD8 T lymphocytes. The increase in CD4 T cells upon IL-15/IL-15Rα treatment is 10-fold, while the increase in the CD8+ population is significantly greater, reaching 100-fold (FIG. 5). These results underscore the feasibility of using IL-15/IL-15Rα DNA to correct defects associated with lymphopenia (e.g., caused by total absence of IL-15 or of another etiology). Analysis of lymphocytes migrating in different organs in the presence of IL-15 suggests that many acquire rapidly a memory phenotype in the absence of antigen recognition and that IL-15 promotes re-entry of some lymphocytes into the thymus. The issue of lymphocyte re-entry in the thymus is controversial, and the study of IL-15 effects may contribute to the understanding of this phenomenon. See, Sprent and Surh (2009) *Immunol Cell Biol* 87:46-49; Bosco, et al., (2009) *Immunol Cell Biol* 87:50-57; Agus, et al., (1991) *J Exp Med* 173:1039-1046. Our preliminary data indicate that transfer of CFSE loaded thymocytes into normal mice results in homing into the thymus only in animals receiving IL-15.

We have found that IL-15 decreases the frequency of apoptotic thymocytes, mainly by promoting their terminal differentiation into mature single positive T cells. Our results after intrathymic injection of CFSE indicate that IL-15 increases thymic output, as reflected by the higher frequency of fully mature CFSE labeled T cells in the spleen and lung of IL-15 treated mice.

We have further observed that the enlarged spleen size upon IL-15 treatment is partially due to increased frequency of B lymphocytes, either by local proliferation, B cell migration from other compartments, or both. In addition, during in vivo experiments with adoptive transferred CFSE-labeled splenocytes we observed IL-15-induced proliferation of both CD4 naïve and memory T cells. In contrast to CD8+ T cells, which almost universally proliferate in the presence of IL-15, the CD4+ T cell responses appear to be restricted to a subset of cells.

Example 2: Correction of Cyclophosphamide-Induced Lymphopenia by IL-15/IL-15Rα DNA Administration Summary The present example shows the reversal of cyclophosphamide-induced lymphopenia in normal young mice by systemic administration of IL-15. One or two high doses of IL-15 were administered two (2) days (or two (2) and twelve (12) days) after cyclophosphamide by hydrodynamic DNA injection. The results show that mice recover faster from lymphopenia after IL-15 administration in comparison to control mice with cyclophosphamide-induced lymphopenia that did not receive IL-15. Lymphocytes recovered faster in peripheral tissues after IL-15 administration. NK cells were the first to recover, whereas T cells recovered in approximately one month. In the course of these studies, we discovered that two administrations of IL-15 improved T cell recovery over a single administration of IL-15. In addition, low and sustained levels of IL-15 provides for a more efficient repopulation of lymphocytes to the peripheral tissues in comparison to a single high dose. These results demonstrate that IL-15 is useful in treating and/or preventing lymphopenia.

Methods

Cyclophosphamide Administration

Six-to-eight week old female Balb/c mice were obtained from Charles River Laboratory (Frederick, Md.). Cyclophosphamide (Sigma) was dissolved in pyrogen-free saline and injected intra-peritoneally (i.p.) at a dose of 200 mg/kg of body weight. Two treatments with cyclophosphamide were performed at day −4 and −2.

DNA Injection

On day 0, hydrodynamic injection of either a control vector or IL-15 and IL-15Rα expression plasmid into cyclophopshamide treated mice was performed. Empty vector DNA was also administered to the cyclophopshamide-untreated mice, as control. Briefly, 0.2 µg to 2 µg of DNA in 1.6 ml of sterile 0.9% NaCl were injected into mice through the tail vein within 7 seconds using a 27.5 gauge needle. Highly purified, endotoxin-free DNA plasmids were produced using Qiagen EndoFree Giga kit (Qiagen, Hilden).

Lymphocyte Analysis

Mice were sacrificed at different time points (days 2-26) after DNA injection and serum, bone marrow, thymus, spleen, liver and lungs were collected for analysis.

For bone marrow lymphocyte isolation, left and right femurs were collected and centrifuged at 13,000 for 5 min, re-suspended, and centrifuged again (total of 3 times). Collected cells were re-suspended in RPMI containing 10% fetal calf serum and viable cells were counted using Acridine Orange (Molecular Probes)/Ethidium Bromide (Fisher) dye.

For splenocyte or thymocyte isolation, spleens or thymi were gently squeezed through a 100 µm Cell Strainer (Thomas) and washed in RPMI (Gibco) to remove any remaining lymphocytes from the organ stroma. After centrifugation, the cells were re-suspended in RPMI containing 10% fetal calf serum and counted.

To isolate lymphocytes from livers or lungs, the tissues were minced and incubated with 200 U/ml of collagenase (Sigma) and 30 U/ml of DNase (Roche) for 1 h at 37° C., then single cells were collected, centrifuged and re-suspended in complete RPMI with 10% fetal calf serum.

For phenotyping, the cells were incubated with the following mix of directly conjugated anti-mouse antibodies (BD Pharmingen): CD3-APC, CD4-PerCP, CD8-PECy7, CD44-APC, CD49b-FITC, CD19-PE, CD62L-PE. Labeled cell samples were analyzed by flow cytometry using an LSR II Flow Cytometer (BD) and were analyzed using FlowJo software (Tree Star, San Carlos, Calif.).

Lymphocytes of the different group of mice were counted and compared. Statistical analyses were performed using the Prism Software Program. Comparisons of two groups were performed by non-parametric Mann-Whitney t test. Confidence intervals were 0.05, and all p values were two-tailed.

Results

Two injections of cyclophosphamide at days −4 and −2 were used to generate lymphodepleted mice. At day 0 (and also, for some mice at day 10) IL-15/15Rα DNA expression vector was injected in the tail vein, which generated high systemic levels of bioactive IL-15/15Rα, as published (Bergamaschi, et al., *J Biol Chem.* (2008) 283(7):4189-99). The biological effects after injection of IL-15/15Rα DNA were compared to the injection of a non-producing DNA (vector BV) as negative control in cyclophosphamide-treated animals.

Different tissues, including lung, liver, spleen, thymus and bone marrow, were extracted from mice sacrificed at days 2-26 from DNA injection and the lymphocyte populations were studied.

Figure 7:
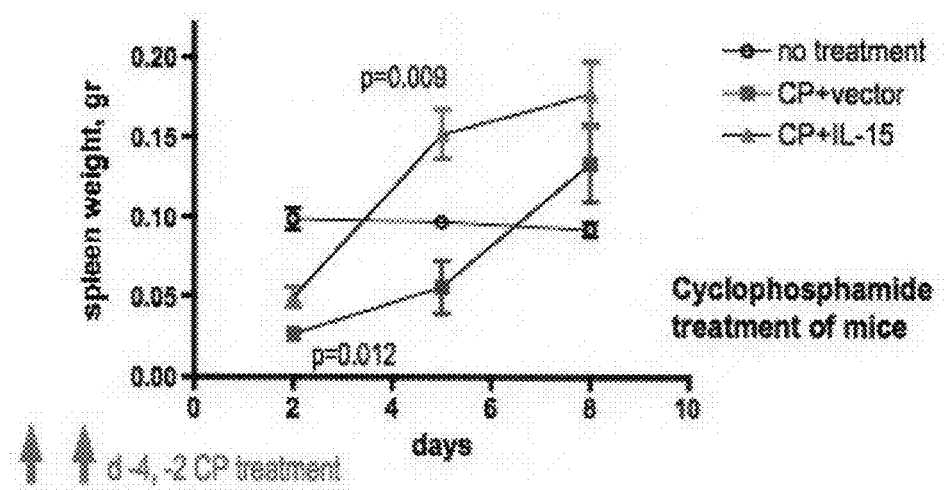
FIG. 7 illustrates spleen weight over time after cyclophosphamide (Cyp) and Cyp+IL-15/IL-15Rα administration.

Cyclophosphamide treatment had strong effects on lymphocytes, as reflected in the increased spleen weight of treated animals (FIG. 7). Four animals per time point were sacrificed and the spleen weight was monitored. The two groups treated with cyclophosphamide (CP+vector, treated with a non-producing DNA vector; CP+IL-15) had a smaller spleen at day 2 after DNA treatment (4 days after cyclophosphamide). At this early point and also at day 5 the IL-15 treated animals showed a statistically significant difference in spleen size, indicating accelerated recovery by IL-15.

Lung

We also analyzed lymphocyte numbers and subsets in different tissues to evaluate the effects of IL-15/15Rα administration. These experiments were performed after one or two IL-15/15Rα DNA administrations (at days 0 and 10).

Lung lymphocytes were evaluated in order to determine the effects of IL-15/15Rα on a peripheral site, where lymphocytes need to function. IL-15 is known to affect strongly CD8+ T cells and NK cells. High levels of IL-15 (achieved with two injections of 2 µg DNA at days 0 and 10), favors lymphocyte recovery in the lung after Cyp treatment.

Effects on Natural Killer (NK) Cells:

Mice were treated at days −4 and −2 and injected with DNA at day 0. Two groups of mice were injected with either BV negative control DNA or with IL-15/IL-15Rα DNA. The IL-15/IL-15Rα-treated animals had a trend for higher NK numbers for all time points. At day 14, comparison of the group receiving empty vector with the group of 2×IL-15/IL-15Rα administration (DNA injections at days 0 and 10) showed that IL-15/15Rα significantly increased lung NK cell recovery (p=0.03).

Figure 8:
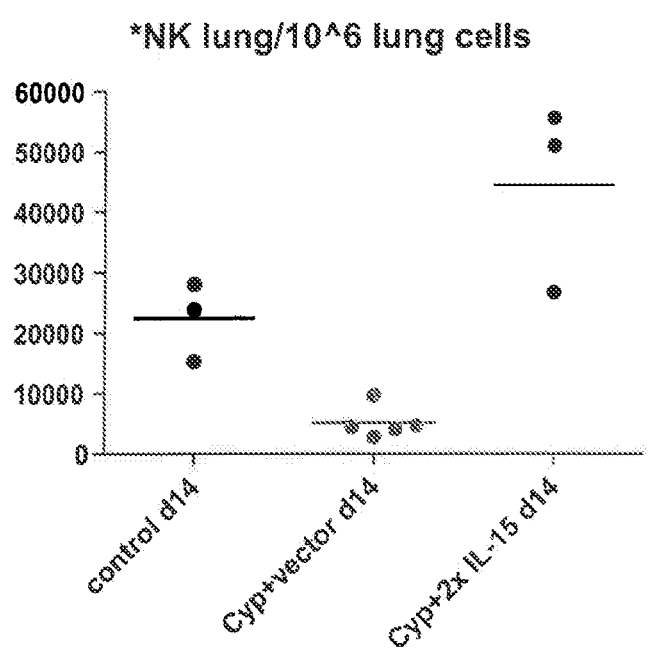
FIG. 8 illustrates the increase in lung NK cells after Cyp administration.

The lymphocyte population that recovers first is the NK cells. In our experiments after cyclophosphamide treatment the NK cells recovered partially in the absence of any other intervention. IL-15/15Rα administration accelerated this recovery. The best recovery was observed after two IL-15 injections at days 0 and 10. Examination at day 14 showed a significant increase in NK by IL-15 compared to Cyp (p=0.03). See, FIG. 8.

Effects on Lung T Cells

Figure 9:
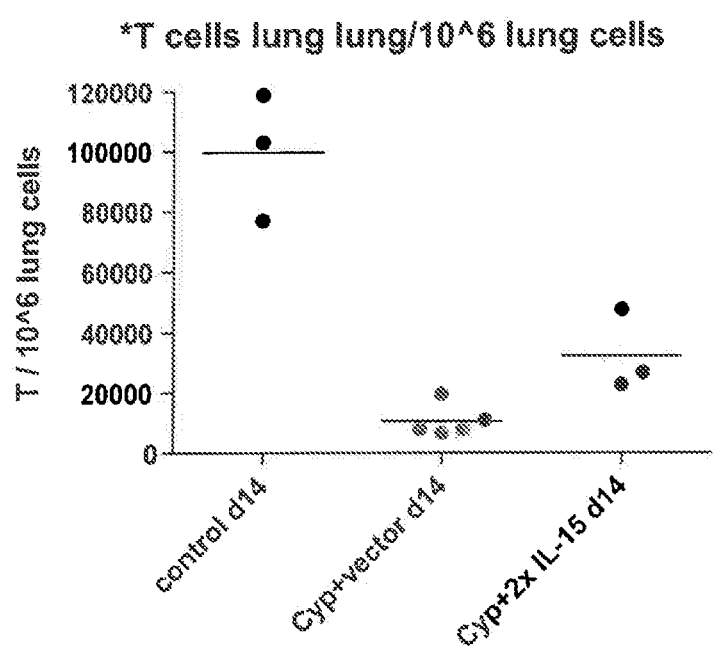
FIG. 9 illustrates the increase in lung T cells in the presence of IL-15/IL-15Rα.

In contrast to NK cells, lung T cells do not recover as fast. The mice were treated and analyzed as above. Lung T cells were enumerated at day 14 after the first DNA injection. It was found that total T cells increased at day 14 after two IL-15/Ra administrations at days 0 and 10, compared to the Cyp treated animals. See, FIG. 9.

Figure 10:
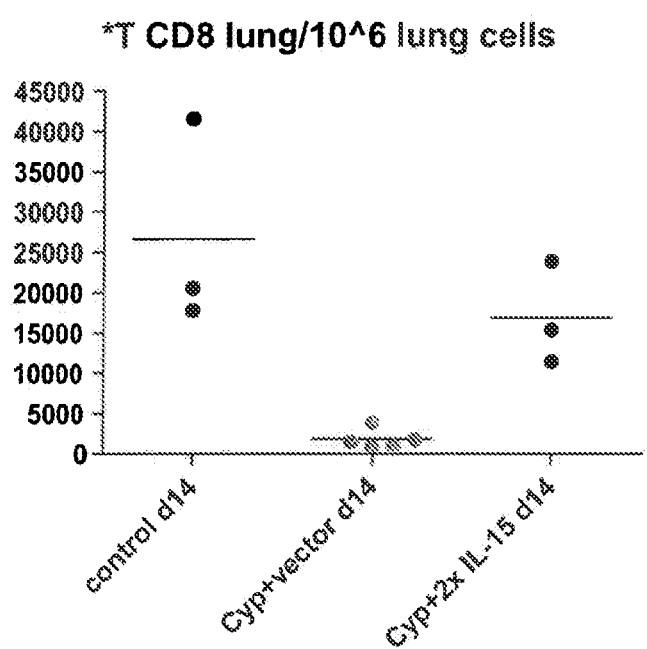
FIG. 10 illustrates that CD8+ T cells partially recover after IL-15/IL-15Rα administration.
Figure 11:
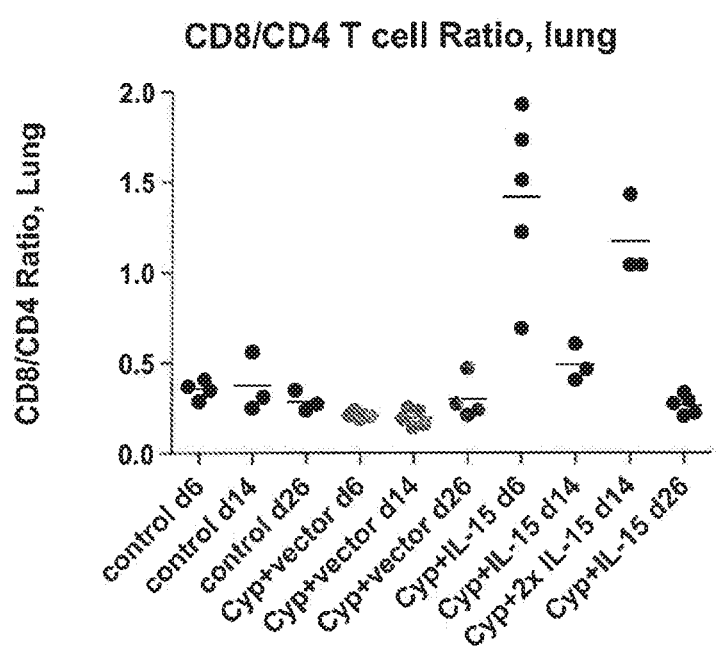
FIG. 11 illustrates the increase in lung CD8+ T cells in the presence of IL-15/IL-15Rα as reflected in the change of the ratio of CD8+ to CD4+ T cells after IL-15 administration.

The lung T cells were also distinguished according to expression of CD4 or CD8 and compared among different groups of mice. It was found that the CD8+ T cells increased preferentially after IL-15/15Rα administration at day 14 (p=0.0357). Moreover, at days 6 and 14 the CD8/CD4 ratio was increased, demonstrating the preferential stimulation of CD8+ T cells by IL-15. The ratio returns to normal by day 26, in the group that received IL-15/15Rα. See, FIGS. 10 and 11.

Spleen

Figure 12:
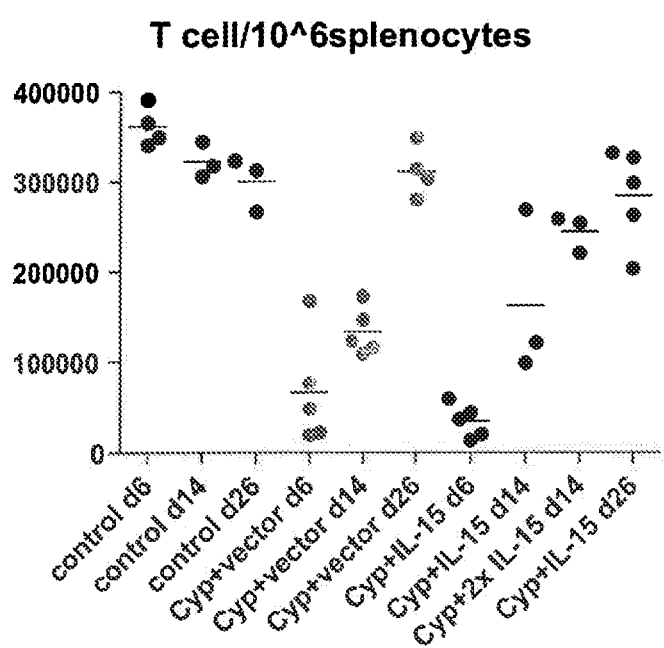
FIG. 12 illustrates a T cell analysis in the spleen after Cyp and IL-15/IL-15Rα administration.

In the spleen, we also found that T cells recover faster after two injections of IL-15/15Rα (p=0.0357). Similar to the results in the lung, two doses of IL-15/15Rα (days 0 and 10) were able to increase spleen lymphocytes after Cyp (p=0.03). See, FIG. 12.

Bone Marrow

Figure 13:
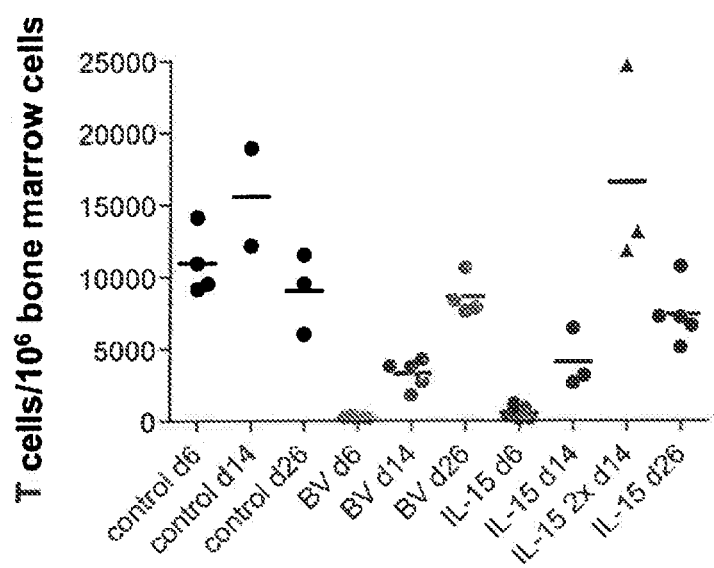
FIG. 13 illustrates the full recovery of bone marrow T cells after IL-15/IL-15Rα administration.

Sustained high level of IL-15 (achieved with two injections of 2 µg DNA at days 0 and 10) resulted in T cell recovery in bone marrow by day 14 after the first DNA injection (FIG. 13). IL-15 affected both CD4 and CD8 compartments. Treatment with two administrations of IL-15/15Rα resulted in high levels of bone marrow T cells at day 14 compared to Cyp treated animals.

Example 3: Therapeutic Effects of IL-15 on Lymphopenia in Two Different Mouse Strains This example also employed Black6 mice to analyze therapeutic effects of various forms of IL-15 on lymphopenia. Two different mouse strains, BALB/c and Black6, were used in these experiments. Both strains showed accelerated lymphocyte reconstitution upon treatment with IL-15/IL-15Rα.

Treatment of lymphoablated mice with IL-15 DNA

Figure 14:
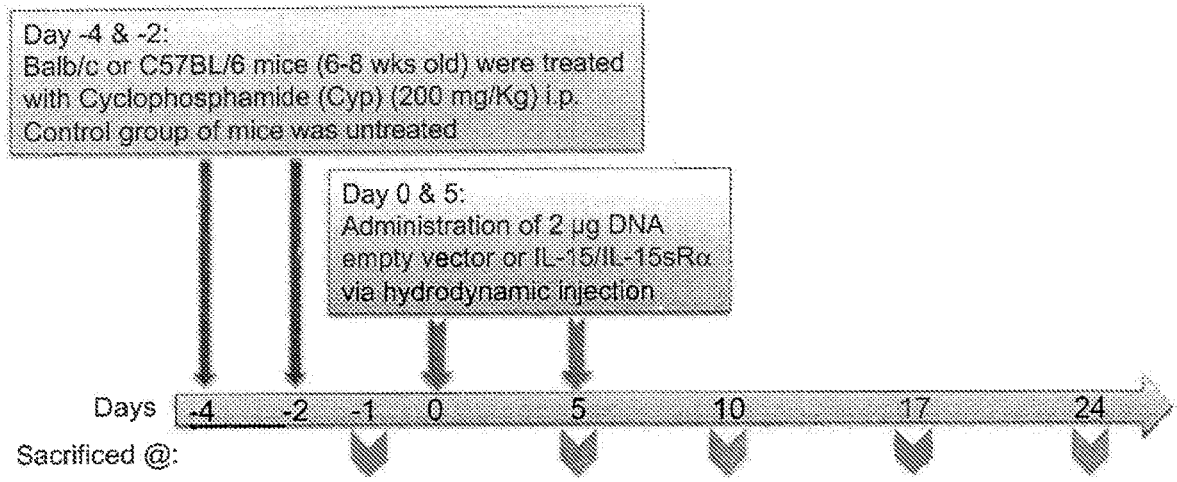
FIG. 14 illustrates the IL-15/IL-15Rα treatment protocol for lymphopenic mice used in Example 3.

Female Balb/c or Black6 mice 6-8 weeks in age were treated intra-peritoneally with a dose of 200 mg/kg of body weight of cyclophosphamide (CYP, FIG. 14). Two injections of CYP were performed at day −4 and day −2. At day 0 and day 5, hydrodynamic injection of either a control DNA or DNA expressing IL-15/IL-15sRα soluble molecule was performed. Control vector was also delivered in CYP-untreated mice as control. Mice were sacrificed at different time points: day −1 to assess the CYP-induced lymphoablation and day 5, 10, 17 and 24 to follow immune reconstitution in presence or absence of exogenous IL-15. Different tissues (spleen, thymus, bone marrow, lung and liver) were harvested and analyzed for the presence of different lymphocyte subsets. Analysis was performed by flow cytometry after staining the cells with fluorescent-labeled antibodies.

For flow analysis, isolated cells were incubated with the following directly conjugated anti-mouse antibodies (BD Pharmingen) in appropriate combinations according to the objectives of the experiment:

CD3-APC or CD3-APC-Cy7, CD4-PerCp, CD8-Pacific Blue, CD44-APC, CD62L-PE, CD19-APC-Cy7 or CD19-PeCy7, CD49b-FITC, CD25-APC-Cy7, CD122-PE. T cells were defined as CD3+ cells in the lymphocyte gate; NK cells were defined as CD3−CD49b+ cells.

For identification of Treg population (T CD4+CD25+ FoxP3+ cells), the cells were fixed and permeabilized (eBioscience), and incubated with anti-mouse FoxP3-PeCy7 antibody (eBioscience). T effector cells were defined as CD3+ FoxP3− lymphocytes. Therefore, the term "Teffector" as used in here refers to all T cells except Treg.

Figure 15:
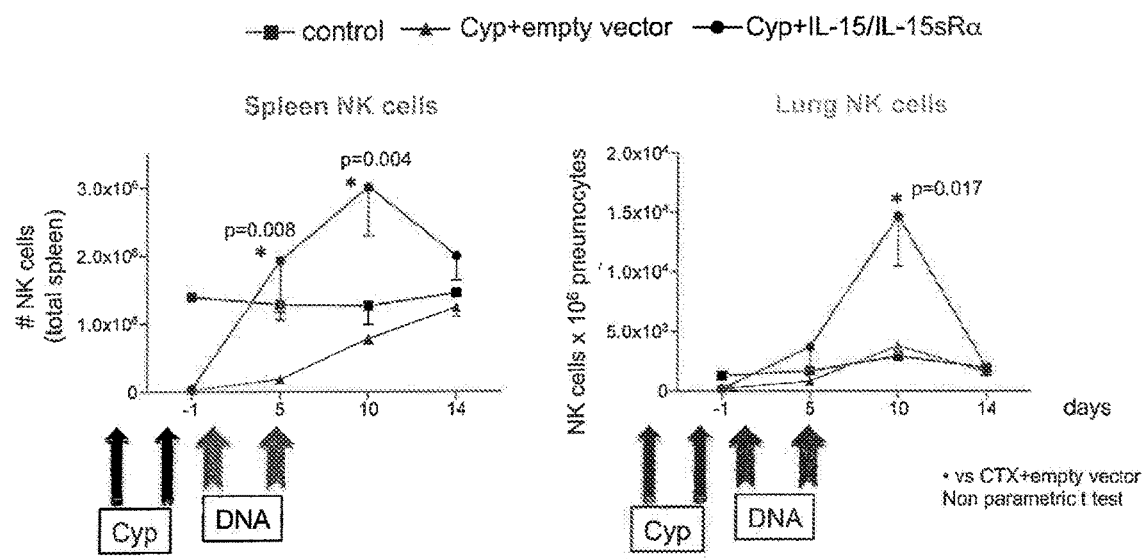
FIG. 15 illustrates that a single administration of IL-15/IL-15sRα-encoding DNA is sufficient for the complete recovery of NK cells in spleen and lung 5 days after DNA injection.

FIG. 15 shows the reconstitution of NK cell compartment in spleen and lung after CYP treatment. CYP-untreated mice were used as baseline control (squares). Two injections of CYP resulted in a drastic reduction of the absolute number of NK cells in both spleen and lung (day −1). NK cells spontaneously recover between day 10 and day 14 days after control DNA injection (triangles). One single administration of IL-15/IL-15sRα DNA was able to promote a full recovery of NK within 5 days after DNA injection. The second IL-15/IL-15sRα expressing DNA injection resulted in an even further expansion of NK cells in both spleen and lung (circles).

Figure 16:
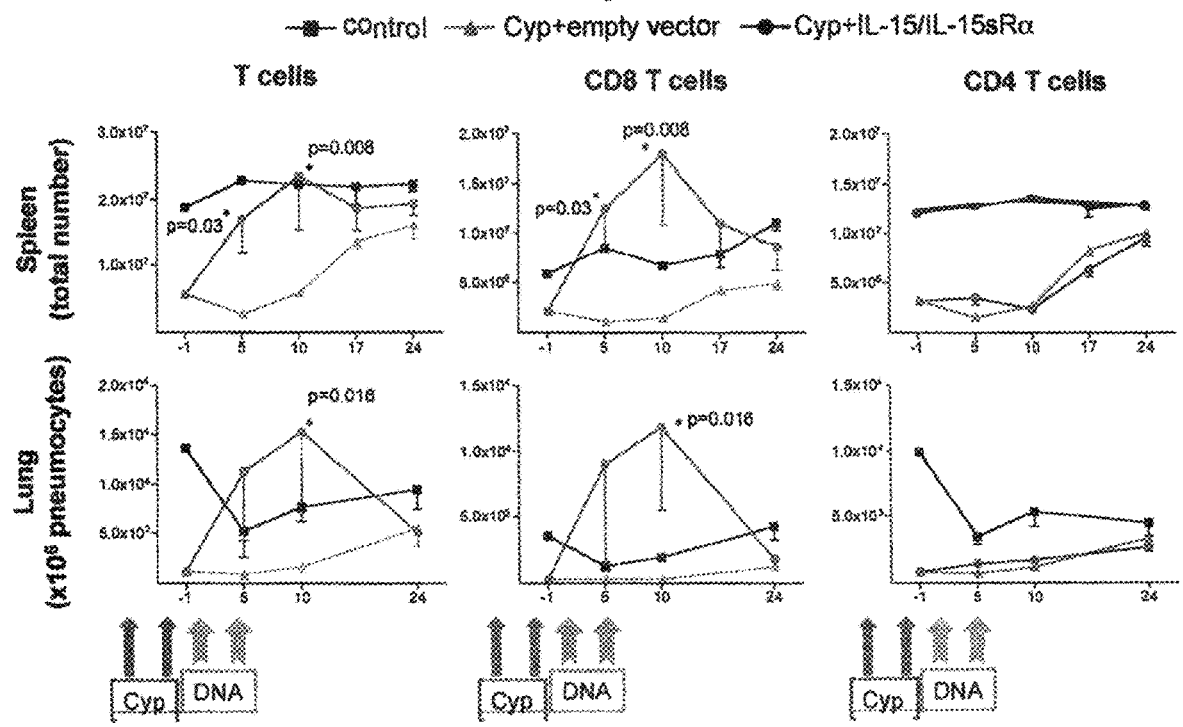
FIG. 16 illustrates that IL-15/IL-15sRα administration promotes the recovery of CD8 T cells within 10 days after treatment, without significantly affecting the recovery of CD4 T cells.

FIG. 16 shows the reconstitution of T cell compartment in spleen and lung after CYP treatment. CYP-untreated mice were used as baseline control (squares). Two injections of CYP resulted in a 4 fold reduction in the level of splenic T cells and in 10 fold reduction in the level of T cells residing in the lung (day −1). The spontaneous recovery of T cells appeared to be slower in comparison with the recovery of NK cells and was still incomplete at day 24 after control DNA injection. The kinetics of spontaneous recovery of T CD8 and T CD4 was similar in both spleen and lung (triangles). Two injections of DNA expressing IL-15/IL-15sRα were able to fully reconstitute the T cell numbers within 10 days after DNA administration in both spleen and lung. IL-15 promoted mainly the expansion of T CD8 cells that reached normal level at day 5 after DNA injection and were boosted over normal level at day 10 after DNA injection. IL-15 did not significantly affect the recovery of T CD4 and B cells.

Figure 17:
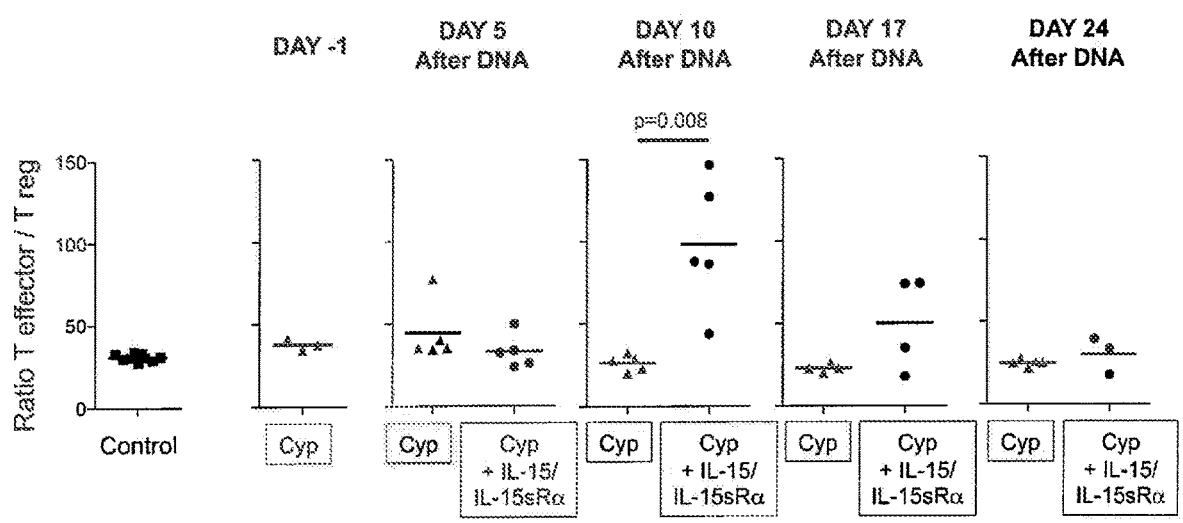
FIG. 17 illustrates that high levels of circulating IL-15/IL-15sRα promote a transient increase in the Teffector/Treg ratio after lymphoablation.

In addition, T cells recovering in the presence of high level of IL-15/IL-15sRα show increased T effector (Teff)/T regulatory (Treg) ratio and increased ability to secrete IFN-gamma and greater degranulation after in vitro stimulation. FIG. 17 is an analysis of the Teff/Treg ratio after CYP treatment for lymphodepletion and during the recovery phase. The Teff/Treg ratio increased significantly at day 10 after IL-15/15sRα DNA injection.

Example 4. DNA Delivery for IL-15 to Treat Lymphopenia

In these examples, three preferred DNA vector combinations are evaluated for the therapeutic delivery of IL-15 to treat lymphopenia:
1 Co-delivery in the same cells, using preferably optimized expression plasmids expressing IL-15 and essentially full-length IL-15Rα, such as SEQ ID NO:13 and SEQ ID NO: 14.
2 Co-delivery in the same cells, using preferably optimized expression plasmids expressing IL-15 and soluble (s) IL-15Rα, such as SEQ ID NO:15.
3 Co-delivery in the same cells, using preferably optimized expression plasmids expressing IL-15 and IL-15Rα fusions to the constant region of an immunoglobulin molecule (Fc) such as SEQ ID NO:16 and SEQ ID NO:19. The construction of Fc fusion proteins is known in the art. Such constructs have been used in in vivo experiments in mice to show that IL-15 and IL 15Rα-Fc fusion heterodimers are active in vivo.

Delivery of IL-15/IL-15Rα heterodimer by approach (1) above leads to expression of both plasma membrane-bound and secreted IL-15/IL-15Rα. Delivery by approach (2) leads to exclusively secreted IL-15/IL-15Rα heterodimer. Delivery by approach (3) leads to a secreted bioactive heterodimer, which is then bound to cells expressing the Fc Ab receptor on their surface. These cells can present the IL-15/IL-15RαFc heterodimer to neighboring cells, resulting in activation.

Figure 18:
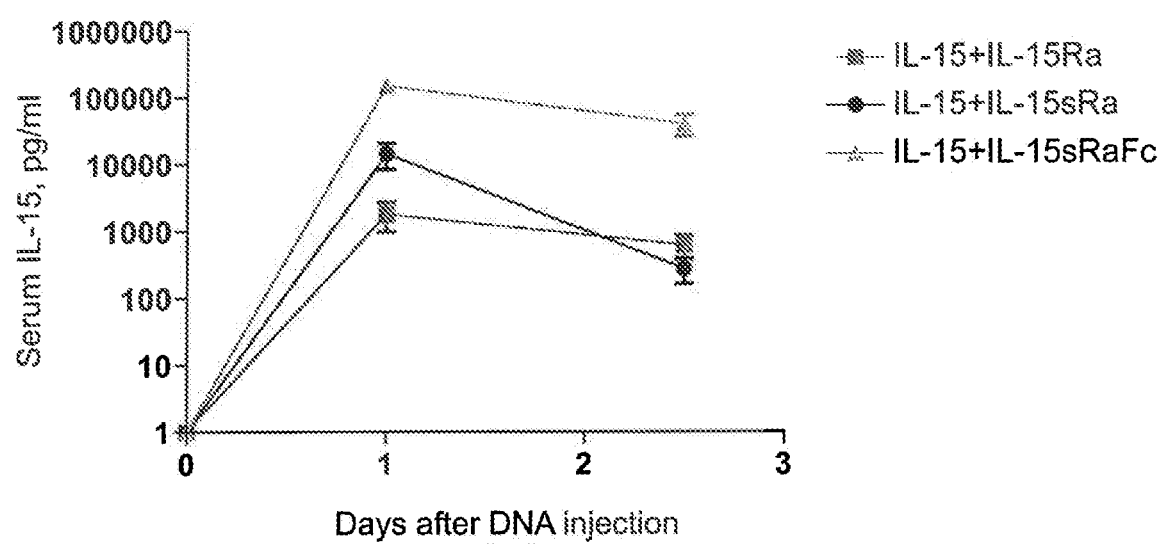
FIG. 18 illustrates IL-15 levels in serum following hydrodynamic delivery of DNA vectors expressing different forms of IL-15.

The three types of vectors have been tested in mice and have been shown to produce systemically bioactive levels of IL-15/IL-15Rα (see FIG. 18, showing expression of the three types of complexes). Because the localization, trafficking and stability of the different types of complexes vary, the biological effects on lymphocytes is also variable. FIG. 18 shows expression of different IL-15/IL-15Rα heterodimeric forms in mice by hydrodynamic injection of DNA vectors. Mice were injected at the tail vein (hydrodynamic delivery) with 0.1 μg of DNA expressing the different forms of IL-15/IL-15Rα. Plasma levels of IL-15 were measured at days 1 and 2.5 by R&D Quantiglo ELISA. Measurement of plasma levels of IL-15 produced by the different vectors showed that the highest plasma levels were achieved by the DNA vector producing IL-15/IL-15RαFc fusion. The stability of the produced proteins was also different, with the IL-15/IL-15RαFc and the IL-15/IL-15Rα full length showing the greatest stability. The IL-15/sIL-15Rα that is not cell associated was less stable.

Table 2 shows the CD4/CD8 ratios measured in the spleen and lung of mice treated with different IL-15/IL-15Rα heterodimeric forms, 2½ days after hydrodynamic injection of 0.1 μg of DNA vector (see FIG. 17).

| VECTOR | Spleen | Lung |
|---|---|---|
| IL-15/IL-15Rα (full length) | 1.36 | 0.8 |
| IL-15/sIL-15Rα (soluble) | 0.81 | 0.24 |
| IL-15/IL-15RαFc fusion to Fc | 0.63 | 0.52 |
| DNA vector control | 2 | 1.61 |

In these experiments, it was discovered that the different molecules have differential effects on lymphocytes. Therefore, the different IL-15 complexes can be used alone or in combinations for the most beneficial treatment under specific conditions. For example, delivery of combinations of IL-15/sRα soluble complex and IL-15/15RαFc fusion complex provides the opportunity to deliver both soluble and cell-bound IL-15 (through the Fc receptor) at different levels and proportions.

Figure 19:
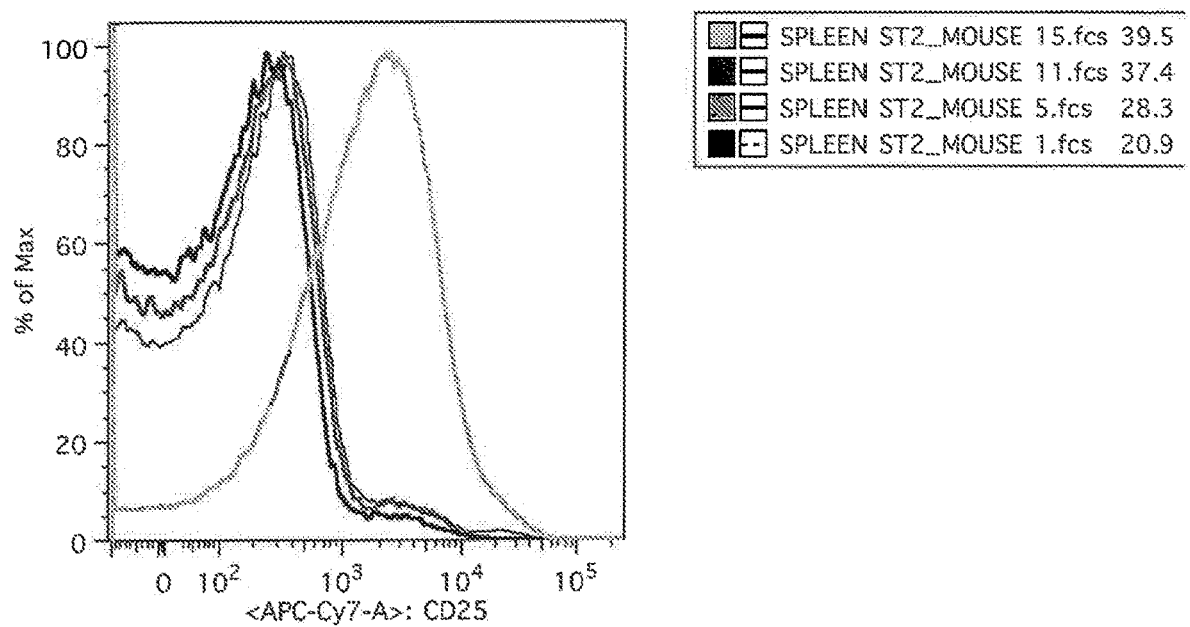
FIG. 19 illustrates CD25 expression on the surface of spleen T cells after IL-15/IL-15Rα DNA delivery.

In addition to the different ratios of CD4/CD8 cells (as shown in Table 1), the different IL-15 heterodimers also showed differences in the effects on other surface markers of lymphocytes. FIG. 19 shows that IL-15/15RαFc expression induced high levels of CD25 (IL-2 Receptor alpha) on both T CD4 and T CD8 cells, whereas the other forms of IL-15/IL-15Rα heterodimers did not affect CD25 expression strongly.

Figure 20:
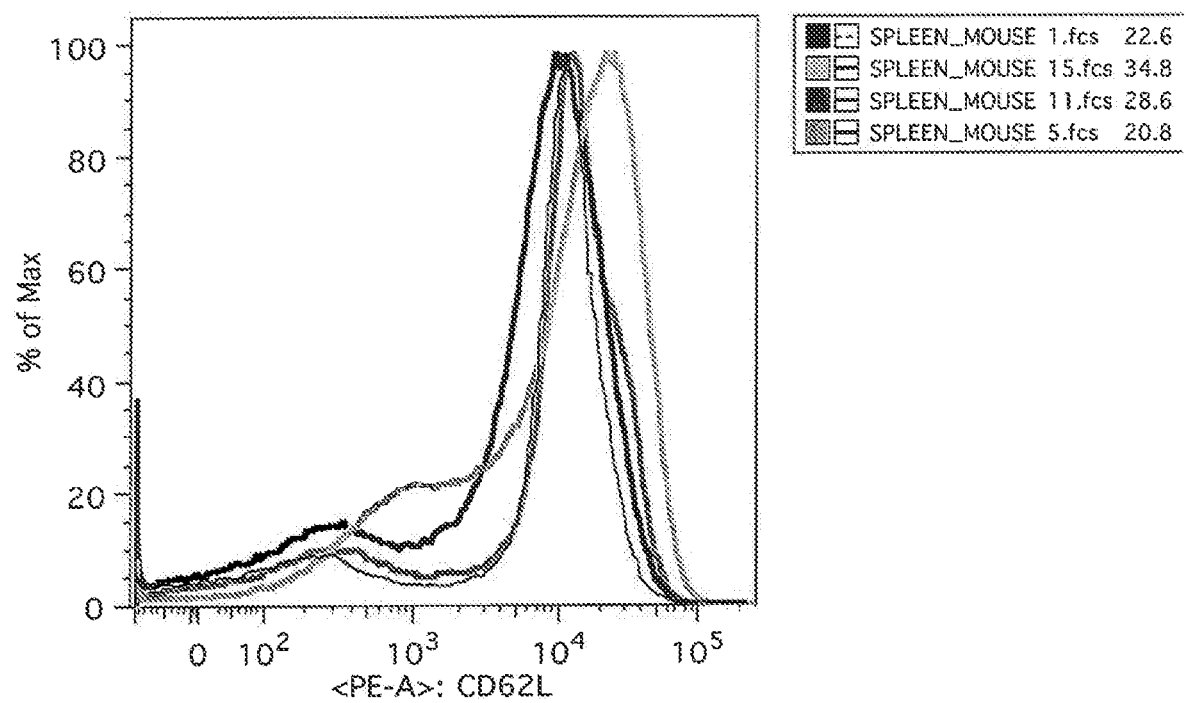
FIG. 20 illustrates expression of CD62L on the surface of spleen T cells after IL-15/IL-15Rα DNA delivery.
Figure 21:
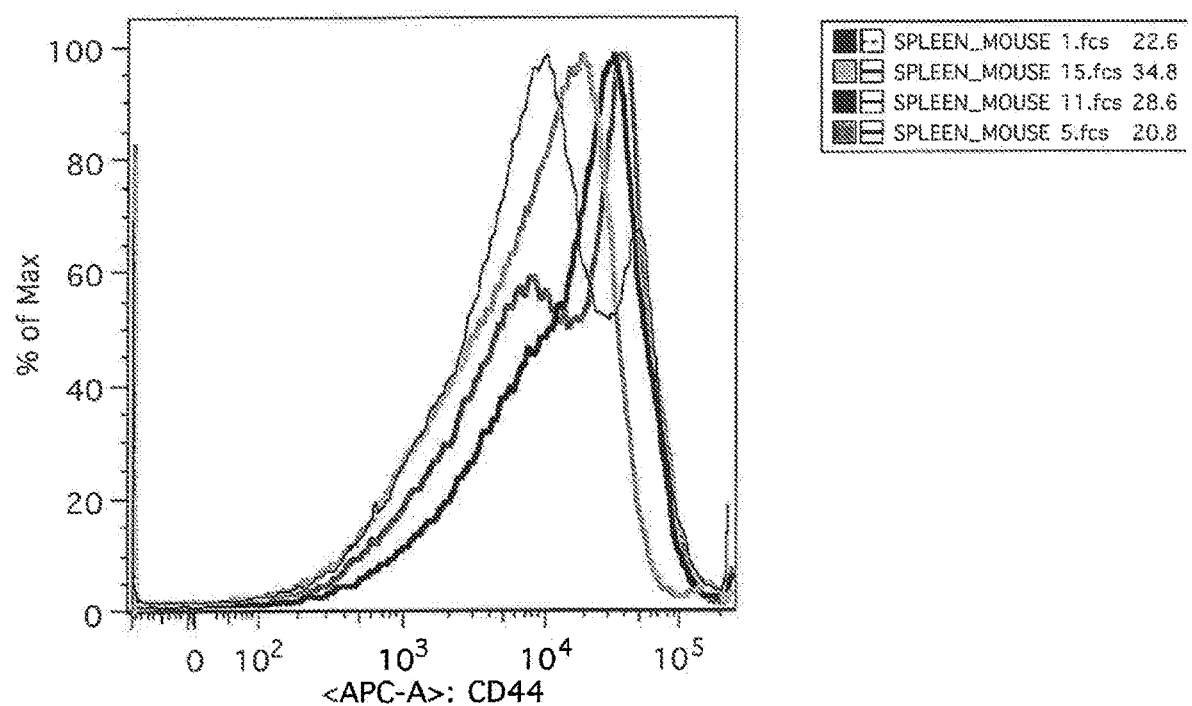
FIG. 21 illustrates express of CD44 on the surface of spleen T cells after IL-15/IL-5Rα DNA delivery.

FIG. 20 shows that IL-15/IL-15RαFc increased the levels of CD62L on the surface of spleen T cells, whereas the other forms of IL-15/IL-15Rα either did not affect or decreased average levels of CD62L on spleen T cells. In contrast, IL-15/IL-15RαFc was less effective in increasing CD44 on spleen T cells compared to either IL-15/IL-15Rα full-length or IL-15/IL-15sRα (FIG. 21).

Example 5. Protein Delivery

As an alternative method to provide IL-15, delivery of purified protein can be used. Protein purification from cell lines over-producing IL-15/IL-15Rα complexes has been achieved. Similar to DNA, different forms of the heterodimer can be used alone or in combinations for obtaining the appropriate effects:
1 Delivery of purified IL-15/soluble (s) IL-15Rα, such as SEQ ID NO: 10 and SEQ ID NO: 12.
2 Delivery of purified IL-15/IL-15RαFc fusion protein (fusion to the constant region of an immunoglobulin molecule, such as SEQ ID NO:17 and SEQ ID NO:20)

IL-15/sIL-15Rα was purified from overproducing human 293 cells and delivered into lympho-ablated mice. The results showed that this heterodimer is bioactive and that it promoted the proliferation of adoptively transferred lymphocytes (T cells, NK cells, but not B cells).

Figure 22:
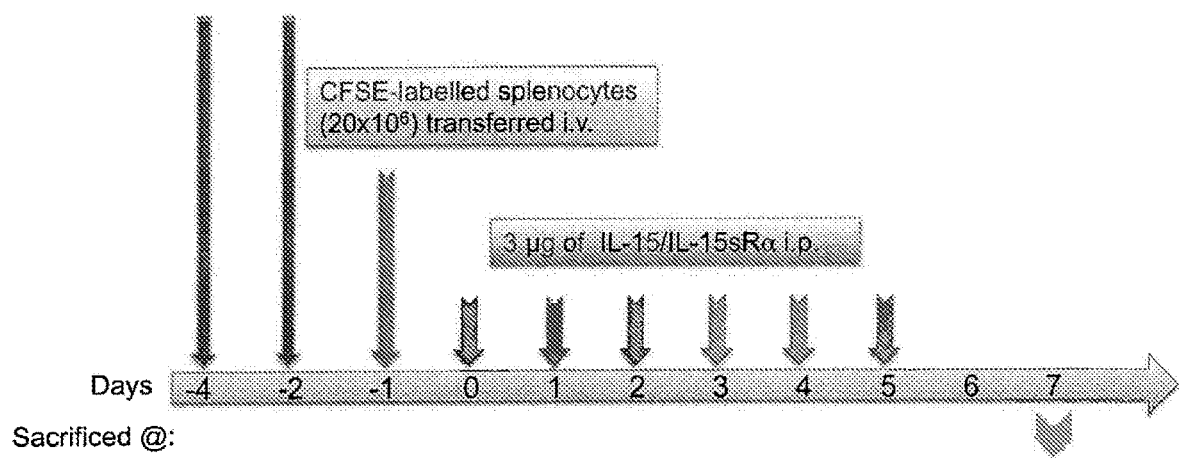
FIG. 22 illustrates a protocol (Example 5) for administration of purified IL-15/IL-15sRα in vivo.

Experimental procedure (FIG. 22): Mice were treated with Cyclophosphamide (Cyp) and two days later they were given 3 μg of HPLC-purified IL-15/s15Rα protein intraperitoneally for 6 days. Splenocytes were purified from young Bl/6 mice, labeled with CFSE, and $10^7$ cells were injected by the IV route to the lympho-ablated animals. Proliferation of the adoptively transferred cells was followed by CFSE dilution.

Thus, these results indicate that different forms of IL-15/IL-15Rα heterodimer have different stability, interactions in the body, processing and stability. This offers the opportunity to exploit such properties for using these cytokines to provide maximal benefit. Accordingly, the different forms can be combined in different ratios and administration schedules. Different forms can be administered either simultaneously or sequentially.

Figure 23:
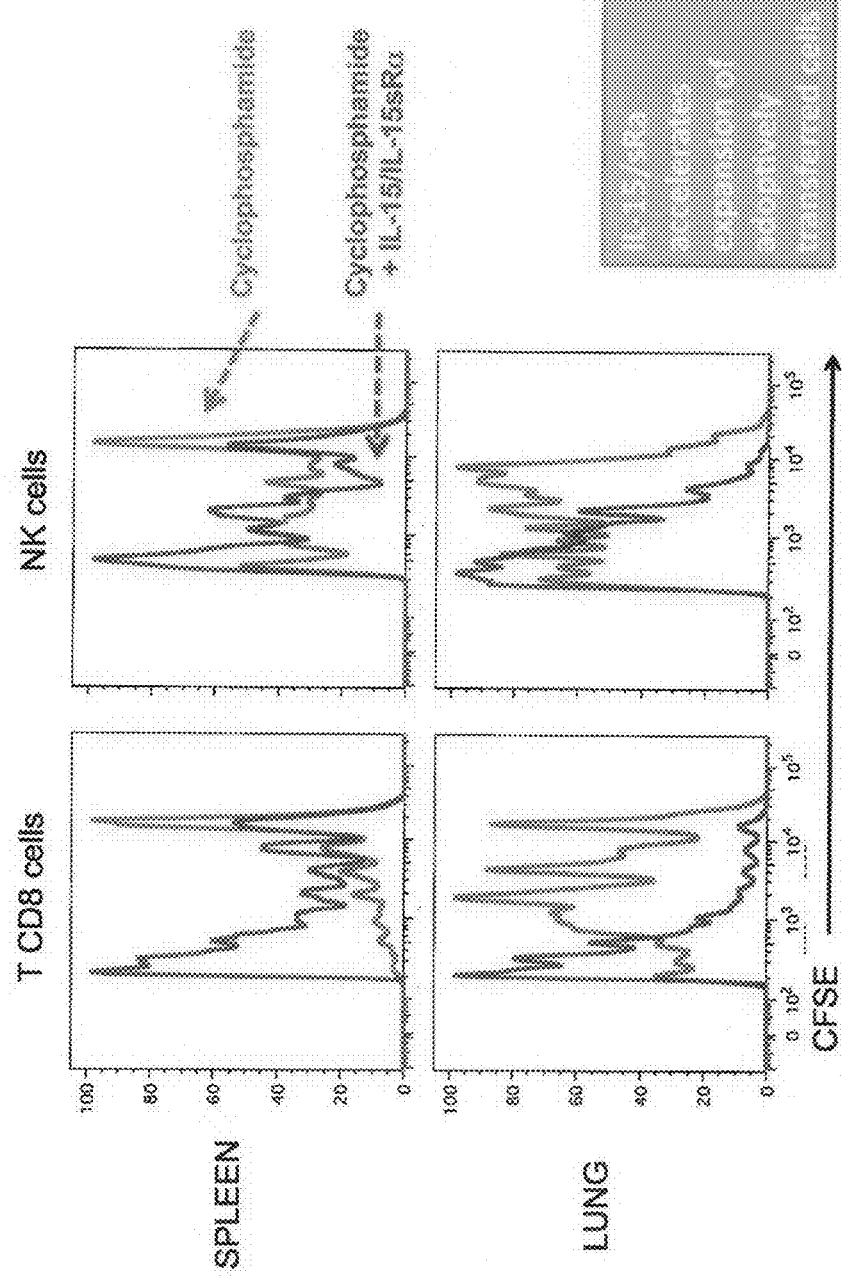
FIG. 23 illustrates that purified IL-15/IL-15Rα is bioactive in vivo.

IL-15Rα-Fc fusions previously employed have been used with various degrees of effectiveness. The studies exemplified in FIG. 23 show that the Fc fusion we used has greater plasma half-life compared to IL-15/s15Rα.

In the examples of sequences, described herein, the 205FC fusion (SEQ ID NO:17) contains the natural processing site generating the s15Rα from the membrane-bound form, whereas the 200FC fusion (SEQ ID NO:20) does not have an intact processing site. These are examples of Fc fusions that may be processed differently to generate non-cell associated forms after cleavage between the 15Rα region and the antibody constant region. Additional molecules can be generated having processing sites for cleavage and generating both cell associated and soluble forms of the cytokine. Additional methods for cell attachment, other than the Fc region are known in the art and can also be employed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES OF SEQUENCES

```
SEQ ID NO: 1
Human wild-type IL-15 nucleic acid sequence
ATGAGAATTTCGAAACCACATTTGAGAAGTATTTCCATCCAGTGCTACTTGTGTTTACTTCT
AAACAGTCATTTTCTAACTGAAGCTGGCATTCATGTCTTCATTTTGGGCTGTTTCAGTGCAG
GGCTTCCTAAAACAGAAGCCAACTGGGTGAATGTAATAAGTGATTTGAAAAAAATTGAAGAT
CTTATTCAATCTATGCATATTGATGCTACTTTATATACGGAAAGTGATGTTCACCCCAGTTG
CAAAGTAACAGCAATGAAGTGCTTTCTCTTGGAGTTACAAGTTATTTCACTTGAGTCTGGAG
ATGCAAGTATTCATGATACAGTAGAAAATCTGATCATCCTAGCAAACAACAGTTTGTCTTCT
AATGGGAATGTAACAGAATCTGGATGCAAAGAATGTGAGGAACTGGAGGAAAAAAATATTAA
AGAATTTTTGCAGAGTTTTGTACATATTGTCCAAATGTTCATCAACACTTCTTGA SEQ ID NO: 2
Human wild-type IL-15 amino acid sequence
M R I S K P H L R S I S I Q C Y L C L L L
N S H F L T E A G I H V F I L G C F S A G
L P K T E A N W V N V I S D L K K I E D L
I Q S M H I D A T L Y T E S D V H P S C K
V T A M K C F L L E L Q V I S L E S G D A
S I H D T V E N L I L A N N N S L S S N G
N V T E S G C K E C E E L E E K N I K E F
L Q S F V H I V Q M F I N T S *

SEQ ID NO: 3
Human improved 1L-15 nucleic acid sequence (opt1)
ATGCGGATCTCGAAGCCGCACCTGCGGTCGATATCGATCCAGTGCTACCTGTGCCTGCTCCT
GAACTCGCACTTCCTCACGGAGGCCGGTATACACGTCTTCATCCTGGGCTGCTTCTCGGCGG
GGCTGCCGAAGACGGAGGCGAACTGGGTGAACGTGATCTCGGACCTGAAGAAGATCGAGGAC
CTCATCCAGTCGATGCACATCGACGCGACGCTGTACACGGAGTCGGACGTCCACCCGTCGTG
CAAGGTCACGGCGATGAAGTGCTTCCTCCTGGAGCTCCAAGTCATCTCGCTCGAGTCGGGGG
ACGCGTCGATCCACGACACGGTGGAGAACCTGATCATCCTGGCGAACAACTCGCTGTCGTCG
AACGGGAACGTCACGGAGTCGGGCTGCAAGGAGTGCGAGGAGCTGGAGGAGAAGAACATCAA
GGAGTTCCTGCAGTCGTTCGTGCACATCGTCCAGATGTTCATCAACACGTCGTGA SEQ ID NO: 4
Human improved IL-15 nucleic acid sequence (Opt2)
ATGAGGATCAGCAAGCCCCACCTGAGGAGCATCAGCATCCAGTGCTACCTGTGCCTGCTGCT
GAACAGCCACTTCCTGACCGAGGCCGGTATACACGTGTTCATCCTGGGCTGCTTTAGCGCCG
GACTGCCCAAGACCGAGGCCAATTGGGTGAACGTGATCAGCGACCTGAAGAAGATCGAGGAC
CTCATCCAGAGCATGCACATCGACGCCACCCTGTACACCGAGAGCGATGTGCACCCCAGCTG
TAAGGTGACCGCCATGAAGTGCTTTCTGCTGGAGCTGCAAGTGATCAGCCTGGAGAGCGGCG
```

| EXAMPLES OF SEQUENCES |
|---|
| ACGCCAGCATCCACGACACCGTGGAGAACCTGATCATCCTGGCCAACAACAGCCTGAGCAGC<br>AACGGCAATGTGACCGAGAGCGGCTGTAAGGAGTGTGAGGAGCTGGAGGAGAAGAACATCAA<br>GGAGTTTCTGCAGAGCTTCGTGCACATCGTGCAGATGTTCATCAACACCAGCTGA |

SEQ ID NO: 5
Homo sapiens interleukin 15 receptor, alpha (IL15RA), transcript
variant 1, mRNA-GenBank Accession No. NM_002189

```
   1  cccagagcag cgctcgccac ctcccccgg cctgggcagc gctcgcccgg ggagtccagc 61  ggtgtcctgt ggagctgccg ccatggcccc gcggcgggcg cgcggctgcc ggaccctcgg 121  tctcccggcg ctgctactgc tgctgctgct ccggccgccg gcgacgcggg catcacgtg 181  ccctccccc atgtccgtgg aacacgcaga catctgggtc aagagctaca gcttgtactc 241  cagggagcgg tacatttgta actctggttt caagcgtaaa gccggcacgt ccagcctgac 301  ggagtgcgtg ttgaacaagg ccacgaatgt cgcccactgg acaaccccca gtctcaaatg 361  cattagagac cctgccctgg ttcaccaaag gccagcgcca ccctccacag taacgacggc 421  aggggtgacc ccacagccag agagcctctc cccttctgga aaagagcccg cagcttcatc 481  tcccagctca acaacacag cggccacaac agcagctatt gtcccgggct cccagctgat 541  gccttcaaaa tcaccttcca caggaaccac agagataagc agtcatgagt cctcccacgg 601  cacccctct cagacaacag ccaagaactg gaactcaca gcatccgcct cccaccagcc 661  gccaggtgtg tatccacagg gccacagcga caccactgtg gctatctcca cgtccactgt 721  cctgctgtgt gggctgagcg ctgtgtctct cctggcatgc tacctcaagt caaggcaaac 781  tcccccgctg gccagcgttg aaatggaagc catggaggct ctgccggtga cttgggggac 841  cagcagcaga gatgaagact ggaaaactg ctctcaccac ctatgaaact cggggaaacc 901  agcccagcta agtccggagt gaaggagcct ctctgcttta gctaaagacg actgagaaga 961  ggtgcaagga agcgggctcc aggagcaagc tcaccaggcc tctcagaagt cccagcagga 1021  tctcacggac tgccgggtcg gcgcctcctg cgcgagggag caggttctcc gcattcccat 1081  gggcaccacc tgcctgcctg tcgtgccttg gacccagggc ccagcttccc aggagagacc 1141  aaaggcttct gagcaggatt tttattttcat tacagtgtga gctgcctgga atacatgtgg 1201  taatgaaata aaaaccctgc cccgaatctt ccgtcctca tcctaacttt cagttcacag 1261  agaaaagtga cataccaaa gctctctgtc aattacaagg cttctcctgg cgtgggagac 1321  gtctacaggg aagacaccag cgtttgggct tctaaccacc ctgtctccag ctgctctgca 1381  cacatggaca gggacctggg aaaggtggga gagatgctga gcccagcgaa tcctctccat 1441  tgaaggattc aggaagaaga aaactcaact cagtgccatt ttacgaatat atgcgtttat 1501  atttatactt ccttgtctat tatatctata cattatatat tatttgtatt ttgacattgt 1561  accttgtata aacaaaataa aacatctatt ttcaatattt ttaaaatgca
```

SEQ ID NO: 6
interleukin 15 receptor, alpha isoform 1 precursor [Homo sapiens]-
GenBank Accession No. NP_002180

```
   1  maprrargcr tlglpallll lllrppatrg itcpppmsve hadiwvksys lysreryicn 61  sgfkrkagts sltecvlnka tnvahwttps lkcirdpalv hqrpappstv ttagvtpqpe 121  slspsgkepa asspssnnta attaaivpgs qlmpskspst gtteisshes shgtpsqtta 181  knweltasas hqppgvypqg hsdttvaist stvllcglsa vsllacylks rqtpplasve 241  meamealpvt wgtssrdedl encshhl
```

| EXAMPLES OF SEQUENCES |
|---|

SEQ ID NO: 7
*Homo sapiens* interleukin 15 receptor, alpha (IL15RA), transcript
variant 2, mRNA-GenBank Accession No. NM_172200

```
   1   caggaattcg gcgaagtggc ggagctgggg ccccagcggg cgccgggggc cgcgggagcc
  61   agcaggtggc gggggctgcg ctccgcccgg ccagagcgc accaggcagg tgcccgcgcc
 121   tccgcaccgc ggcgacacct ccgcgggcac tcacccaggc cggccgctca caaccgagcg
 181   cagggccgcg gagggagacc aggaaagccg aaggcggagc agctggaggc gaccagcgcc
 241   gggcgaggtc aagtggatcc gagccgcaga gagggctgga gagagtctgc tctccgatga
 301   ctttgcccac tctcttcgca gtggggacac cggaccgagt gcacactgga ggtcccagag
 361   cacgacgagc gcggaggacc gggaggctcc cgggcttgcg tgggcatcac gtgccctccc
 421   cccatgtccg tggaacacgc agacatctgg gtcaagagct acagcttgta ctccagggag
 481   cggtacattt gtaactctgg tttcaagcgt aaagccggca cgtccagcct gacggagtgc
 541   gtgttgaaca aggccacgaa tgtcgcccac tggacaaccc ccagtctcaa atgcattaga
 601   gaccctgccc tggttcacca aaggccagcg ccaccctcca gtaacgac ggcaggggtg
 661   accccacagc cagagagcct ctccccttct ggaaaagagc cgcagcttc atctcccagc
 721   tcaaacaaca cagcggccac aacagcagct attgtcccgg gctcccagct gatgccttca
 781   aaatcacctt ccacaggaac cacagagata agcagtcatg agtcctccca cggcaccccc
 841   tctcagacaa cagccaagaa ctgggaactc acagcatccg cctcccacca gccgccaggt
 901   gtgtatccac agggccacag cgacaccact gtggctatct ccacgtccac tgtcctgctg
 961   tgtgggctga gcgctgtgtc tctcctggca tgctacctca gtcaaggca aactcccccg
1021   ctggccagcg ttgaaatgga agccatggag gctctgccgg tgacttgggg gaccagcagc
1081   agagatgaag acttggaaaa ctgctctcac cacctatgaa actcggggaa accagcccag
1141   ctaagtccgg agtgaaggag cctctctgct ttagctaaag acgactgaga agaggtgcaa
1201   ggaagcgggc tccaggagca agctcaccag gcctctcaga agtcccagca ggatctcacg
1261   gactgccggg tcggcgcctc ctgcgcgagg gagcaggttc tccgcattcc catgggcacc
1321   acctgcctgc ctgtcgtgcc ttggacccag ggcccagctt cccaggagag accaaaggct
1381   tctgagcagg attttattt cattacagtg tgagctgcct ggaatacatg tggtaatgaa
1441   ataaaaaccc tgccccgaat cttccgtccc tcatcctaac tttcagttca cagagaaaag
1501   tgacataccc aaagctctct gtcaattaca aggcttctcc tggcgtggga gacgtctaca
1561   gggaagacac cagcgtttgg gcttctaacc accctgtctc cagctgctct gcacacatgg
1621   acagggacct gggaaaggtg ggagagatgc tgagcccagc gaatcctctc cattgaagga
1681   ttcaggaaga agaaaactca actcagtgcc attttacgaa tatatgcgtt tatatttata
1741   cttccttgtc tattatatct atacattata tattatttgt attttgacat tgtaccttgt
1801   ataaacaaaa taaacatct attttcaata tttttaaaat gca
```

SEQ ID NO: 8
interleukin 15 receptor, alpha isoform 2 [*Homo sapiens*]-GenBank
Accession No. NP_751950

```
   1   msvehadiwv ksyslysrer yicnsgfkrk agtssltecv lnkatnvahw ttpslkcird
  61   palvhqrpap pstvttagvt pqpeslspsg kepaasspss nntaattaai vpgsqlmpsk
 121   spstgtteis shesshgtps qttaknwelt asashqppgv ypqghsdttv aiststvllc
 181   glsavsllac ylksrqtppl asvemeamea lpvtwgtssr dedlencshh l
```

| EXAMPLES OF SEQUENCES |
|---|

SEQ ID NO: 9
Improved human interleukin 15 (IL-15) receptor alpha (IL15Ra), transcript variant 1 (OPT)

```
atggccccga ggcgggcgcg aggctgccgg accctcggtc tcccggcgct gctactgctc    60
ctgctgctcc ggccgccggc gacgcggggc atcacgtgcc cgccccccat gtccgtggag   120
cacgcagaca tctgggtcaa gagctacagc ttgtactccc gggagcggta catctgcaac   180
tcgggtttca gcggaaggc cggcacgtcc agcctgacgg agtgcgtgtt gaacaaggcc   240
acgaatgtcg cccactggac gacccctcg ctcaagtgca tccgcgaccc ggccctggtt   300
caccagcggc ccgcgccacc ctccaccgta acgacggcgg gggtgacccc gcagccggag   360
agcctctccc cgtcgggaaa ggagcccgcc gcgtcgtcgc ccagctcgaa caacacggcg   420
gccacaactg cagcgatcgt cccgggctcc agctgatgc cgtcgaagtc gccgtccacg   480
ggaaccacgg agatcagcag tcatgagtcc tcccacggca cccctcgca acgacggcc   540
aagaactggg aactcacggc gtccgcctcc accagccgc cggggtgta tccgcaaggc   600
cacagcgaca ccacggtggc gatctccacg tccacggtcc tgctgtgtgg gctgagcgcg   660
gtgtcgctcc tggcgtgcta cctcaagtcg aggcagactc ccccgctggc cagcgttgag   720
atggaggcca tggaggctct gccggtgacg tgggggacca gcagcaggga tgaggacttg   780
gagaactgct cgcaccacct ataatga                                        807
```

SEQ ID NO: 10-improved human interleukin 15 (IL-15) receptor alpha (IL15Ra), transcript variant 1 (OPT)

```
Met Ala Pro Arg Arg Ala Arg Gly Cys Arg Thr Leu Gly Leu Pro Ala
  1               5                  10                  15
Leu Leu Leu Leu Leu Leu Arg Pro Pro Ala Thr Arg Gly Ile Thr
             20                  25                  30
Cys Pro Pro Pro Met Ser Val Glu His Ala Asp Ile Trp Val Lys Ser
         35                  40                  45
Tyr Ser Leu Tyr Ser Arg Glu Arg Tyr Ile Cys Asn Ser Gly Phe Lys
     50                  55                  60
Arg Lys Ala Gly Thr Ser Ser Leu Thr Glu Cys Val Leu Asn Lys Ala
 65                  70                  75                  80
Thr Asn Val Ala His Trp Thr Thr Pro Ser Leu Lys Cys Ile Arg Asp
                 85                  90                  95
Pro Ala Leu Val His Gln Arg Pro Ala Pro Ser Thr Val Thr Thr
             100                 105                 110
Ala Gly Val Thr Pro Gln Pro Glu Ser Leu Ser Pro Ser Gly Lys Glu
         115                 120                 125
Pro Ala Ala Ser Ser Pro Ser Ser Asn Asn Thr Ala Ala Thr Thr Ala
130                 135                 140
Ala Ile Val Pro Gly Ser Gln Leu Met Pro Ser Lys Ser Pro Ser Thr
145                 150                 155                 160
Gly Thr Thr Glu Ile Ser Ser His Glu Ser Ser His Gly Thr Pro Ser
                 165                 170                 175
Gln Thr Thr Ala Lys Asn Trp Glu Leu Thr Ala Ser Ala Ser His Gln
             180                 185                 190
Pro Pro Gly Val Tyr Pro Gln Gly His Ser Asp Thr Thr Val Ala Ile
         195                 200                 205
Ser Thr Ser Thr Val Leu Leu Cys Gly Leu Ser Ala Val Ser Leu Leu
     210                 215                 220
Ala Cys Tyr Leu Lys Ser Arg Gln Thr Pro Pro Leu Ala Ser Val Glu
225                 230                 235                 240
```

| EXAMPLES OF SEQUENCES |
|---|

Met Glu Ala Met Glu Ala Leu Pro Val Thr Trp Gly Thr Ser Ser Arg
                      245                    250                    255

Asp Glu Asp Leu Glu Asn Cys Ser His His Leu
        260                    265

SEQ ID NO: 11-improved human soluble interleukin 15 (IL-15) receptor alpha (IL-15sRa) (OPT)

```
atggccccga ggcgggcgcg aggctgccgg accctcggtc tcccggcgct gctactgctc      60
ctgctgctcc ggccgccggc gacgcggggc atcacgtgcc cgcccccat gtccgtggag      120
cacgcagaca tctgggtcaa gagctacagc ttgtactccc gggagcggta catctgcaac    180
tcgggtttca agcggaaggc cggcacgtcc agcctgacgg agtgcgtgtt gaacaaggcc    240
acgaatgtcg cccactggac gacccccctcg ctcaagtgca tccgcgaccc ggccctggtt   300
caccagcggc ccgcgccacc ctccaccgta acgacggcgg gggtgacccc gcagccggag    360
agcctctccc cgtcgggaaa ggagcccgcc gcgtcgtcgc ccagctcgaa caacacggcg    420
gccacaactg cagcgatcgt cccgggctcc cagctgatgc cgtcgaagtc gccgtccacg    480
ggaaccacgg agatcagcag tcatgagtcc tcccacggca cccctcgca acgacggcc    540
aagaactggg aactcacggc gtccgcctcc caccagccgc cggggtgta tccgcaaggc    600
cacagcgaca ccacgtaatg a                                                621
```

SEQ ID NO: 12-improved human soluble interleukin 15 (IL-15) receptor alpha (IL-15sRa) (OPT)

Met Ala Pro Arg Arg Ala Arg Gly Cys Arg Thr Leu Gly Leu Pro Ala
  1                  5                    10                    15

Leu Leu Leu Leu Leu Leu Leu Arg Pro Pro Ala Thr Arg Gly Ile Thr
            20                    25                    30

Cys Pro Pro Pro Met Ser Val Glu His Ala Asp Ile Trp Val Lys Ser
        35                    40                    45

Tyr Ser Leu Tyr Ser Arg Glu Arg Tyr Ile Cys Asn Ser Gly Phe Lys
        50                    55                    60

Arg Lys Ala Gly Thr Ser Ser Leu Thr Glu Cys Val Leu Asn Lys Ala
65                    70                    75                    80

Thr Asn Val Ala His Trp Thr Thr Pro Ser Leu Lys Cys Ile Arg Asp
            85                    90                    95

Pro Ala Leu Val His Gln Arg Pro Ala Pro Pro Ser Thr Val Thr Thr
          100                  105                110

Ala Gly Val Thr Pro Gln Pro Glu Ser Leu Ser Pro Ser Gly Lys Glu
        115                  120                125

Pro Ala Ala Ser Ser Pro Ser Ser Asn Asn Thr Ala Ala Thr Thr Ala
        130                  135                140

Ala Ile Val Pro Gly Ser Gln Leu Met Pro Ser Lys Ser Pro Ser Thr
145                  150                  155                160

Gly Thr Thr Glu Ile Ser Ser His Glu Ser Ser His Gly Thr Pro Ser
          165                  170                175

Gln Thr Thr Ala Lys Asn Trp Glu Leu Thr Ala Ser Ala Ser His Gln
        180                  185                190

Pro Pro Gly Val Tyr Pro Gln Gly His Ser Asp Thr Thr
        195                  200                205

SEQ ID NO: 13
Dual expression plasmid human IL15Ra + IL15
```
CCTGGCCATTGCATACGTTGTATCCATATCATAATATGTACATTTATATTGGCTCATGTCCA
ACATTACCGCCATGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCATAGTAACG
```

EXAMPLES OF SEQUENCES

```
CCAATAGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGACGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGGAGGTCTATATAAGCAGAGCTCGTTTAGTGAACCGTCAGAT
CGCCTGGAGACGCCATCCACGCTGTTTTGACCTCCATAGAAGACACCGGGACCGATCCAGCC
TCCGCGGGCGCGCGTCGAGGAATTCGCTAGCAAGAAATGGCCCCGAGGCGGGCGCGAGGCTG
CCGGACCCTCGGTCTCCCGGCGCTGCTACTGCTCCTGCTGCTCCGGCCGCCGGCGACGCGGG
GCATCACGTGCCCGCCCCCATGTCCGTGGAGCACGCAGACATCTGGGTCAAGAGCTACAGC
TTGTACTCCCGGGAGCGGTACATCTGCAACTCGGGTTTCAAGCGGAAGGCCGGCACGTCCAG
CCTGACGGAGTGCGTGTTGAACAAGGCCACGAATGTCGCCCACTGGACGACCCCCTCGCTCA
AGTGCATCCGCGACCCGGCCCTGGTTCACCAGCGGCCCGCGCCACCCTCCACCGTAACGACG
GCGGGGGTGACCCCGCAGCCGGAGAGCCTCTCCCCGTCGGGAAAGGAGCCCGCCGCGTCGTC
GCCCAGCTCGAACAACACGGCGGCCACAACTGCAGCGATCGTCCCGGGCTCCCAGCTGATGC
CGTCGAAGTCGCCGTCCACGGGAACCACGGAGATCAGCAGTCATGAGTCCTCCCACGGCACC
CCCTCGCAAACGACGGCCAAGAACTGGGAACTCACGGCGTCCGCCTCCCACCAGCCGCCGGG
GGTGTATCCGCAAGGCCACAGCGACACCACGGTGGCGATCTCCACGTCCACGGTCCTGCTGT
GTGGGCTGAGCGCGGTGTCGCTCCTGGCGTGCTACCTCAAGTGCAGGCAGACTCCCCCGCTG
GCCAGCGTTGAGATGGAGGCCATGGAGGCTCTGCCGGTGACGTGGGGGACCAGCAGCAGGGA
TGAGGACTTGGAGAACTGCTCGCACCACCTATAATGAGAATTCACGCGTGGATCTGATATCG
GATCTGCTGTGCCTTCTAGTTGCCAGCCATCTGTTGTTTGCCCCTCCCCCGTGCCTTCCTTG
ACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGGAGGATT
GGGAAGACAATAGCAGGCATGCTGGGGATGCGGTGGGCTCTATGGGTACCCAGGTGCTGAAG
AATTGACCCGGTTCCTCCTGGGCCAGAAAGAAGCAGGCACATCCCCTTCTCTGTGACACACC
CTGTCCACGCCCCTGGTTCTTAGTTCCAGCCCCACTCATAGGACACTCATAGCTCAGGAGGG
CTCCGCCTTCAATCCCACCCGCTAAAGTACTTGGAGCGGTCTCTCCCTCCCTCATCAGCCCA
CCAAACCAAACCTAGCCTCCAAGAGTGGGAAGAAATTAAAGCAAGATAGGCTATTAAGTGCA
GAGGGAGAGAAAATGCCTCCAACATGTGAGGAAGTAATGAGAGAAATCATAGAATTTCTTCC
GCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCAA
TGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCT
GACAGTTACCAATGCTTAATCAGTGAGGCACCTATCTCAGCGATCTGTCTATTTCGTTCATC
CATAGTTGCCTGACTCGGGGGGGGGGGCGCTGAGGTCTGCCTCGTGAAGAAGGTGTTGCTG
ACTCATACCAGGCCTGAATCGCCCCATCATCCAGCCAGAAAGTGAGGGAGCCACGGTTGATG
AGAGCTTTGTTGTAGGTGGACCAGTTGGTGATTTTGAACTTTTGCTTTGCCACGGAACGGTC
TGCGTTGTCGGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACCAATT
CTGATTAGAAAAACTCATCGAGCATCAAATGAAACTGCAATTTATTCATATCAGGATTATCA
ATACCATATTTTTGAAAAAGCCGTTTCTGTAATGAAGGAGAAAACTCACCGAGGCAGTTCCA
TAGGATGGCAAGATCCTGGTATCGGTCTGCGATTCCGACTCGTCCAACATCAATACAACCTA
TTAATTTCCCCTCGTCAAAAATAAGGTTATCAAGTGAGAAATCACCATGAGTGACGACTGAA
TCCGGTGAGAATGGCAAAAGCTTATGCATTTCTTTCCAGACTTGTTCAACAGGCCAGCCATT
ACGCTCGTCATCAAAATCACTCGCATCAACCAAACCGTTATTCATTCGTGATTGCGCCTGAG
CGAGACGAAATACGCGATCGCTGTTAAAAGGACAATTACAAACAGGAATCGAATGCAACCGG
CGCAGGAACACTGCCAGCGCATCAACAATATTTTCACCTGAATCAGGATATTCTTCTAATAC
CTGGAATGCTGTTTTCCCGGGGATCGCAGTGGTGAGTAACCATGCATCATCAGGAGTACGGA
TAAAATGCTTGATGGTCGGAAGAGGCATAAATTCCGTCAGCCAGTTTAGTCTGACCATCTCA
TCTGTAACATCATTGGCAACGCTACCTTTGCCATGTTTCAGAAACAACTCTGGCGCATCGGG
CTTCCCATACAATCGATAGATTGTCGCACCTGATTGCCCGACATTATCGCGAGCCCATTTAT
ACCCATATAAATCAGCATCCATGTTGGAATTTAATCGCGGCCTCGAGCAAGACGTTTCCCGT
TGAATATGGCTCATAACACCCCTTGTATTACTGTTTATGTAAGCAGACAGTTTTATTGTTCA
TGATGATATATTTTTATCTTGTGCAATGTAACATCAGAGATTTTGAGACACAACGTGGATCA
TCCAGACATGATAAGATACATTGATGAGTTTGGACAAACCACAACTAGAATGCAGTGAAAAA
AATGCTTTATTTGTGAAATTTGTGATGCTATTGCTTTATTTGTAACCATTATAAGCTGCAAT
AAACAAGTTAACAACAACAATTGCATTCATTTTATGTTTCAGGTTCAGGGGGAGGTGTGGGA
GGTTTTTTAAAGCAAGTAAAACCTCTACAAATGTGGTATGGCTGATTATGATCGTCGAGGAT
CTGGATCCGTTAACCGATATCCGCGAATTCGGCGCGCCGGGCCCTCACGACGTGTTGATGAA
CATCTGGACGATGTGCACGAACGACTGCAGGAACTCCTTGATGTTCTTCTCCTCCAGCTCCT
CGCACTCCTTGCAGCCCGACTCCGTGACGTTCCCGTTCGACGACAGCGAGTTGTTCGCAGG
ATGATCAGGTTCTCCACCGTGTCGTGGATCGACGCGTCCCCGACTCGAGCGAGATGACTTG
GAGCTCCAGGAGGAAGCACTTCATCGCCGTGACCTTGCACGACGGGTGGACGTCCGACTCCG
TGTACAGCGTCGCGTCGATGTGCATCGACTGGATGAGGTCCTCGATCTTCTTCAGGTCCGAG
```

| EXAMPLES OF SEQUENCES |
|---|
| ATCACGTTCACCCAGTTCGCCTCCGTCTTCGGCAGCCCCGCCGAGAAGCAGCCCAGGATGAA
GACGTGTATACCGGCCTCCGTGAGGAAGTGCGAGTTCAGGAGCAGGCACAGGTAGCACTGGA
TCGATATCGACCGCAGGTGCGGCTTCGAGATCCGCATTTCTTGTCGACACTCGACAGATCCA
AACGCTCCTCCGACGTCCCCAGGCAGAATGGCGGTTCCCTAAACGAGCATTGCTTATATAGA
CCTCCCATTAGGCACGCCTACCGCCCATTTACGTCAATGGAACGCCCATTTGCGTCATTGCC
CCTCCCCATTGACGTCAATGGGATGTACTTGGCAGCCATCGCGGGCATTTACCGCCATTG
ACGTCAATGGGAGTACTGCCAATGTACCCTGGCGTACTTCCAATAGTAATGTACTTGCCAAG
TTACTATTAATAGATATTGATGTACTGCCAAGTGGGCCATTTACCGTCATTGACGTCAATAG
GGGGCGTGAGAACGGATATGAATGGGCAATGAGCCATCCCATTGACGTCAATGGTGGGTGGT
CCTATTGACGTCAATGGGCATTGAGCCAGGCGGGCCATTTACCGTAATTGACGTCAATGGG
GAGGCGCCATATACGTCAATAGGACCGCCCATATGACGTCAATAGGAAAGACCATGAGGCCC
TTTCGTCTCGCGCGTTTCGGTGATGACGGTGAAAACCTCTGACACATGCAGCTCCCGGAGAC
GGTCACAGCTTGTCTGTAAGCGGATGCCGGGAGCAGACAAGCCCGTCAGGGCGCGTCAGCGG
GTGTTGGCGGGTGTCGGGGCTGGCTTAACTATGCGGCATCAGAGCAGATTGTACTGAGAGTG
CACCATATGCGGTGTGAAATACCGCACAGATGCGTAAGGAGAAAATACCGCATCAGATTGGC
TATTGG |

SEQ ID NO: 14
Dual expression plasmid human IL15Ra + IL15tPA6

CCTGGCCATTGCATACGTTGTATCCATATCATAATATGTACATTTATATTGGCTCATGTCCA
ACATTACCGCCATGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCATAGTAACG
CCAATAGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGACGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGGAGGTCTATATAAGCAGAGCTCGTTTAGTGAACCGTCAGAT
CGCCTGGAGACGCCATCCACGCTGTTTTGACCTCCATAGAAGACACCGGGACCGATCCAGCC
TCCGCGGGCGCGTCGAGGAATTCGCTAGCAAGAAATGGCCCCGAGGCGGGCGCGAGGCTG
CCGGACCCTCGGTCTCCCGGCGCTGCTACTGCTCCTGCTGCTCCGGCCGCCGGCGACGCGGG
GCATCACGTGCCCGCCCCCATGTCCGTGGAGCACGCAGACATCTGGGTCAAGAGCTACAGC
TTGTACTCCCGGGAGCGGTACATCTGCAACTCGGGTTTCAAGCGGAAGGCCGGCACGTCCAG
CCTGACGGAGTGCGTGTTGAACAAGGCCACGAATGTCGCCCACTGGACGACCCCCTCGCTCA
AGTGCATCCGCGACCCGGCCCTGGTTCACCAGCGGCCCGCGCCACCCTCCACCGTAACGACG
GCGGGGGTGACCCCGCAGCCGGAGAGCCTCTCCCCGTCGGGAAAGGAGCCCGCCGCGTCGTC
GCCCAGCTCGAACAACACGGCGGCCACAACTGCAGCGATCGTCCCGGGCTCCCAGCTGATGC
CGTCGAAGTCGCCGTCCACGGGAACCACGGAGATCAGCAGTCATGAGTCCTCCCACGGCACC
CCCTCGCAAACGACGGCCAAGAACTGGGAACTCACGGCGTCCGCCTCCCACCAGCCGCCGGG
GGTGTATCCGCAAGGCCACAGCGACACCACGGTGGCGATCTCCACGTCCACGGTCCTGCTGT
GTGGGCTGAGCGCGGTGTCGCTCCTGGCGTGCTACCTCAAGTCGAGGCAGACTCCCCCGCTG
GCCAGCGTTGAGATGGAGGCCATGGAGGCTCTGCCGGTGACGTGGGGGACCAGCAGCAGGGA
TGAGGACTTGGAGAACTGCTCGCACCACCTATAATGAGAATTCACGCGTGGATCTGATATCG
GATCTGCTGTGCCTTCTAGTTGCCAGCCATCTGTTGTTTGCCCCTCCCCCGTGCCTTCCTTG
ACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGCAGGACAGCAAGGGGGAGGATT
GGGAAGACAATAGCAGGCATGCTGGGGATGCGGTGGGCTCTATGGGTACCCAGGTGCTGAAG
AATTGACCCGGTTCCTCCTGGGCCAGAAAGAAGCAGGCACATCCCCTTCTCTGTGACACACC
CTGTCCACGCCCCTGGTTCTTAGTTCCAGCCCCACTCATAGGACACTCATAGCTCAGGAGGG
CTCCGCCTTCAATCCCACCCGCTAAAGTACTTGGAGCGGTCTCTCCCTCCCTCATCAGCCCA
CCAAACCAAACCTAGCCTCCAAGAGTGGGAAGAAATTAAAGCAAGATAGGCTATTAAGTGCA
GAGGGAGAGAAAATGCCTCCAACATGTGAGGAAGTAATGAGAGAAATCATAGAATTTCTTCC
GCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCAA
TGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCT
GACAGTTACCAATGCTTAATCAGTGAGGCACCTATCTCAGCGATCTGTCTATTTCGTTCATC
CATAGTTGCCTGACTCGGGGGGGGGGGGCGCTGAGGTCTGCCTCGTGAAGAAGGTGTTGCTG
ACTCATACCAGGCCTGAATCGCCCCATCATCCAGCCAGAAAGTGAGGGAGCCACGGTTGATG
AGAGCTTTGTTGTAGGTGGACCAGTTGGTGATTTTGAACTTTTGCTTTGCCACGGAACGGTC
TGCGTTGTCGGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACCAATT
CTGATTAGAAAAACTCATCGAGCATCAAATGAAACTGCAATTTATTCATATCAGGATTATCA
ATACCATATTTTTGAAAAAGCCGTTTCTGTAATGAAGGAGAAAACTCACCGAGGCAGTTCCA

EXAMPLES OF SEQUENCES

```
TAGGATGGCAAGATCCTGGTATCGGTCTGCGATTCCGACTCGTCCAACATCAATACAACCTA
TTAATTTCCCCTCGTCAAAAATAAGGTTATCAAGTGAGAAATCACCATGAGTGACGACTGAA
TCCGGTGAGAATGGCAAAAGCTTATGCATTTCTTTCCAGACTTGTTCAACAGGCCAGCCATT
ACGCTCGTCATCAAAATCACTCGCATCAACCAAACCGTTATTCATTCGTGATTGCGCCTGAG
CGAGACGAAATACGCGATCGCTGTTAAAAGGACAATTACAAACAGGAATCGAATGCAACCGG
CGCAGGAACACTGCCAGCGCATCAACAATATTTTCACCTGAATCAGGATATTCTTCTAATAC
CTGGAATGCTGTTTTCCCGGGGATCGCAGTGGTGAGTAACCATGCATCATCAGGAGTACGGA
TAAAATGCTTGATGGTCGGAAGAGGCATAAATTCCGTCAGCCAGTTTAGTCTGACCATCTCA
TCTGTAACATCATTGGCAACGCTACCTTTGCCATGTTTCAGAAACAACTCTGGCGCATCGGG
CTTCCCATACAATCGATAGATTGTCGCACCTGATTGCCCGACATTATCGCGAGCCCATTTAT
ACCCATATAAATCAGCATCCATGTTGGAATTTAATCGCGGCCTCGAGCAAGACGTTTCCCGT
TGAATATGGCTCATAACACCCCTTGTATTACTGTTTATGTAAGCAGACAGTTTTATTGTTCA
TGATGATATATTTTTATCTTGTGCAATGTAACATCAGAGATTTTGAGACACAACGTGGATCA
TCCAGACATGATAAGATACATTGATGAGTTTGGACAAACCACAACTAGAATGCAGTGAAAAA
AATGCTTTATTTGTGAAATTTGTGATGCTATTGCTTTATTTGTAACCATTATAAGCTGCAAT
AAACAAGTTAACAACAACAATTGCATTCATTTTATGTTTCAGGTTCAGGGGGAGGTGTGGGA
GGTTTTTTAAAGCAAGTAAAACCTCTACAAATGTGGTATGGCTGATTATGATCGTCGAGGAT
CTGGATCTGGATCCGTTAACCGATATCCGCGAATTCGGCGCGCCGGGCCCTCACGACGTGTT
GATGAACATCTGGACGATGTGCACGAACGACTGCAGGAACTCCTTGATGTTCTTCTCCTCCA
GCTCCTCGCACTCCTTGCAGCCCGACTCCGTGACGTTCCCGTTCGACGACAGCGAGTTGTTC
GCCAGGATGATCAGGTTCTCCACCGTGTCGTGGATCGACGCGTCCCCCGACTCGAGCGAGAT
GACTTGGAGCTCCAGGAGGAAGCACTTCATCGCCGTGACCTTGCACGACGGGTGGACGTCCG
ACTCCGTGTACAGCGTCGCGTCGATGTGCATCGACTGGATGAGGTCCTCGATCTTCTTCAGG
TCCGAGATCACGTTCACCCAGTTTCTGGCTCCTCTTCTGAATCGGGCATGGATTTCCTGGCT
GGGCGAAACGAAGACTGCTCCACACAGCAGCAGCACACAGCAGAGCCCTCTCTTCATTGCAT
CCATTTCTTGTCGACAGATCCAAACGCTCCTCCGACGTCCCCAGGCAGAATGGCGGTTCCCT
AAACGAGCATTGCTTATATAGACCTCCCATTAGGCACGCCTACCGCCCATTTACGTCAATGG
AACGCCCATTTGCGTCATTGCCCCTCCCCATTGACGTCAATGGGGATGTACTTGGCAGCCAT
CGCGGGCCATTTACCGCCATTGACGTCAATGGGAGTACTGCCAATGTACCCTGGCGTACTTC
CAATAGTAATGTACTTGCCAAGTTACTATTAATAGATATTGATGTACTGCCAAGTGGGCCAT
TTACCGTCATTGACGTCAATAGGGGGCGTGAGAACGGATATGAATGGGCAATGAGCCATCCC
ATTGACGTCAATGGTGGGTGGTCCTATTGACGTCAATGGGCATTGAGCCAGGCGGGCCATTT
ACCGTAATTGACGTCAATGGGGAGGCGCCATATACGTCAATAGGACCGCCCATATGACGTC
AATAGGAAAGACCATGAGGCCCTTTCGTCTCGCGCGTTTCGGTGATGACGGTGAAAACCTCT
GACACATGCAGCTCCCGGAGACGGTCACAGCTTGTCTGTAAGCGGATGCCGGGAGCAGACAA
GCCCGTCAGGGCGCGTCAGCGGGTGTTGGCGGGTGTCGGGGCTGGCTTAACTATGCGGCATC
AGAGCAGATTGTACTGAGAGTGCACCATATGCGGTGTGAAATACCGCACAGATGCGTAAGGA
GAAAATACCGCATCAGATTGGCTATTGG
```

SEQ ID NO: 15
Dual expression plasmid human IL15sRa(soluble) + IL15tPA6

```
CCTGGCCATTGCATACGTTGTATCCATATCATAATATGTACATTTATATTGGCTCATGTCCA
ACATTACCGCCATGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCATAGTAACG
CCAATAGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGACGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGGAGGTCTATATAAGCAGAGCTCGTTTAGTGAACCGTCAGAT
CGCCTGGAGACGCCATCCACGCTGTTTTGACCTCCATAGAAGACACCGGGACCGATCCAGCC
TCCGCGGGCGCGCGTCGAGGAATTCGCTAGCAAGAAATGGCCCCGAGGCGGGCGCGAGGCTG
CCGGACCCTCGGTCTCCCGGCGCTGCTACTGCTCCTGCTGCTCCGGCCGCCGGCGACGCGGG
GCATCACGTGCCCGCCCCCATGTCCGTGGAGCACGCAGACATCTGGGTCAAGAGCTACAGC
TTGTACTCCCGGGAGCGGTACATCTGCAACTCGGGTTTCAAGCGGAAGGCCGGCACGTCCAG
CCTGACGGAGTGCGTGTTGAACAAGGCCACGAATGTCGCCCACTGGACGACCCCCTCGCTCA
AGTGCATCCGCGACCCGGCCCTGGTTCACCAGCGGCCCGCGCCACCCTCCACCGTAACGACG
GCGGGGGTGACCCCGCAGCGGAGAGCCTCTCCCCGTCGGGAAAGGAGCCCGCCGCGTCGTC
GCCCAGCTCGAACAACACGGCGGCCACAACTGCAGCGATCGTCCCGGGCTCCCAGCTGATGC
CGTCGAAGTCGCCGTCCACGGGAACCACGGAGATCAGCAGTCATGGTCCTCCCACGGCACC
CCCTCGCAAACGACGGCCAAGAACTGGGAACTCACGGCGTCCGCCTCCACCAGCCGCCGGG
GGTGTATCCGCAAGGCCACAGCGACACCACGTAATGAGAATTCGCGGATATCGGTTAACGGA
TCCAGATCTGCTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCGC
ATTGTCTGAGTAGGTGTCATTCTATTCTGGGGGGTGGGGTGGGGCAGGACAGCAAGGGGGAG
GATTGGGAAGACAATAGCAGGCATGCTGGGGATGCGGTGGGCTCTATGGGTACCCAGGTGCT
GAAGAATTGACCCGGTTCCTCCTGGGCCAGAAAGAAGCAGGCACATCCCCTTCTCTGTGACA
CACCCTGTCCACGCCCCTGGTTCTTAGTTCCAGCCCCACTCATAGGACACTCATAGCTCAGG
AGGGCTCCGCCTTCAATCCCACCCGCTAAAGTACTTGGAGGTCTCTCCCTCCCTCATCAG
CCCACCCAAACCAAACCTAGCCTCCAAGAGTGGGAAGAAATTAAAGCAAGATAGGCTATTAAG
TGCAGAGGGAGAGAAAATGCCTCCAACATGTGAGGAAGTAATGAGAGAAATCATAGAATTTC
TTCCGCTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGAGGTGGCGAAACC
```

EXAMPLES OF SEQUENCES

```
CGACAGGACTATAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGCGTGGCGCTTTC
TCAATGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCC
AACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAGAT
TACGCGCAGAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAAGGATCTTCACC
TAGATCCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATTTCGTT
CATCCATAGTTGCCTGACTCGGGGGGGGGGGGCGCTGAGGTCTGCCTCGTGAAGAAGGTGTT
GCTGACTCATACCAGGCCTGAATCGCCCCATCATCCAGCCAGAAAGTGAGGGAGCCACGGTT
GATGAGAGCTTTGTTGTAGGTGGACCAGTTGGTGATTTTGAACTTTTGCTTTGCCACGGAAC
GGTCTGCGTTGTCGGGAAGATGCGTGATCTGATCCTTCAACTCAGCAAAAGTTCGATTTATT
CAACAAAGCCGCCGTCCCGTCAAGTCAGCGTAATGCTCTGCCAGTGTTACAACCAATTAACC
AATTCTGATTAGAAAAACTCATCGAGCATCAAATGAAACTGCAATTTATTCATATCAGGATT
ATCAATACCATATTTTTGAAAAAGCCGTTTCTGTAATGAAGGAGAAAACTCACCGAGGCAGT
TCCATAGGATGGCAAGATCCTGGTATCGGTCTGCGATTCCGACTCGTCCAACATCAATACAA
CCTATTAATTTCCCCTCGTCAAAAATAAGGTTATCAAGTGAGAAATCACCCATGAGTGACGAC
TGAATCCGGTGAGAATGGCAAAAGCTTATGCATTTCTTTCCAGACTTGTTCAACAGGCCAGC
CATTACGCTCGTCATCAAAATCACTCGCATCAACCAAACCGTTATTCATTCGTGATTGCGCC
TGAGCGAGACGAAATACGCGATCGCTGTTAAAAGGACAATTACAAACAGGAATCGAATGCAA
CCGGCGCAGGAACACTGCCAGCGCATCAACAATATTTTCACCTGAATCAGGATATTCTTCTA
ATACCTGGAATGCTGTTTTCCCGGGGATCGCAGTGGTGAGTAACCATGCATCATCAGGAGTA
CGGATAAAATGCTTGATGGTCGGAAGAGGCATAAATTCCGTCAGCCAGTTTAGTCTGACCAT
CTCATCTGTAACATCATTGGCAACGCTACCTTTGCCATGTTTCAGAAACAACTCTGGCGCAT
CGGGCTTCCCATACAATCGATAGATTGTCGCACCTGATTGCCCGACATTATCGCGAGCCCAT
TTATACCCATATAAATCAGCATCCATGTTGGAATTTAATCGCGGCCTCGAGCAAGACGTTTC
CCGTTGAATATGGCTCATAACACCCCTTGTATTACTGTTTATGTAAGCAGACAGTTTTATTG
TTCATGATGATATATTTTTATCTTGTGCAATGTAACATCAGAGATTTTGAGACACAACGTGG
ATCATCCAGACATGATAAGATACATTGATGAGTTTGGACAAACCACAACTAGAATGCAGTGA
AAAAAATGCTTTATTTGTGAAATTTGTGATGCTATTGCTTTATTTGTAACCATTATAAGCTG
CAATAAACAAGTTAACAACAACAATTGCATTCATTTTATGTTTCAGGTTCAGGGGGAGGTGT
GGGAGGTTTTTTAAAGCAAGTAAAACCTCTACAAATGTGGTATGGCTGATTATGATCGTCGA
GGATCTGGATCTGGATCCGTTAACCGATATCCGCGAATTCGGCGCGCCGGGCCCTCACGACG
TGTTGATGAACATCTGGACGATGTGCACGAACGACTGCAGGAACTCCTTGATGTTCTTCTCC
TCCAGCTCCTCGCACTCCTTGCAGCCCGACTCCGTGACGTTCCCGTTCGACGACAGCGAGTT
GTTCGCCAGGATGATCAGGTTCTCCACCGTGTCGTGGATCGACGCGTCCCCCGACTCGAGCG
AGATGACTTGGAGCTCCAGGAGGAAGCACTTCATCGCCGTGACCTTGCACGACGGGTGGACG
TCCGACTCCGTGTACAGCGTCGCGTCGATGTGCATCGACTGGATGAGGTCCTCGATCTTCTT
CAGGTCCGAGATCACGTTCACCCAGTTTCTGGCTCCTCTTCTGAATCGGGCATGGATTTCCT
GGCTGGGCGAAACGAAGACTGCTCCACACAGCAGCAGCACACAGCAGAGCCCTCTCTTCATT
GCATCCATTTCTTGTCGACAGATCCAAACGCTCCTCCGACGTCCCCAGGCAGAATGGCGGTT
CCCTAAACGAGCATTGCTTATATAGACCTCCCATTAGGCACGCCTACCGCCCATTTACGTCA
ATGGAACGCCCATTTGCGTCATTGCCCCTCCCCATTGACGTCAATGGGGATGTACTTGGCAG
CCATCGCGGGCCATTTACCGCCATTGACGTCAATGGGAGTACTGCCAATGTACCCTGGCGTA
CTTCCAATAGTAATGTACTTGCCAAGTTACTATTAATAGATATTGATGTACTGCCAAGTGGG
CCATTTACCGTCATTGACGTCAATAGGGGCGTGAGAACGGATATGAATGGGCAATGAGCCA
TCCCATTGACGTCAATGGTGGGTGGTCCTATTGACGTCAATGGGCATTGAGCCAGGCGGGCC
ATTTACCGTAATTGACGTCAATGGGGAGGCGCCATATACGTCAATAGGACCGCCCATATGA
CGTCAATAGGAAAGACCATGAGGCCCTTTCGTCTCGCGCGTTTCGGTGATGACGGTGAAAAC
CTCTGACACATGCAGCTCCCGGAGACGGTCACAGCTTGTCTGTAAGCGGATGCCGGGAGCAG
ACAAGCCCGTCAGGGCGCGTCAGCGGGTGTTGGCGGGTGTCGGGCTGGCTTAACTATGCGG
CATCAGAGCAGATTGTACTGAGAGTGCACCATATGCGGTGTGAAATACCGCACAGATGCGTA
AGGAGAAAATACCGCATCAGATTGGCTATTGG
```

SEQ ID NO: 16-DPhuIL15sRa205FC + huGMIL15 The capitalized, bolded region is the coding region for the IL-15Receptor alpha 205FC fusion

```
cctggccattgcatacgttgtatccatatcataatatgtacatttatattggctcatgtcca
acattaccgccatgttgacattgattattgactagttattaatagtaatcaattacggggtc
attagttcatagcccatatatggagttccgcgttacataacttacggtaaatggcccgcctg
gctgaccgcccaacgacccccgcccattgacgtcaataatgacgtatgttcccatagtaacg
ccaatagggactttccattgacgtcaatgggtggagtatttacggtaaactgcccacttggc
agtacatcaagtgtatcatatgccaagtacgccccctattgacgtcaatgatggtaaatggc
ccgcctggcattatgcccagtacatgaccttatgggactttcctacttggcagtacatctac
gtattagtcatcgctattaccatggtgatgcggttttggcagtacatcaatgggcgtggata
gcggtttgactcacggggatttccaagtctccaccccattgacgtcaatgggagtttgtttt
ggcaccaaaatcaacgggactttccaaaatgtcgtaacaactccgccccattgacgcaaatg
ggcggtaggcgtgtacggtgggaggtctatataagcagagctcgtttagtgaaccgtcagat
cgcctggagacgccatccacgctgttttgacctccatagaagacaccgggaccgatccagcc
tccgcgggcgcgcgtcgacgctagcaagaaATGGCCCCGAGGCGGGCGCGAGGCTGCCGGAC
CCTCGGTCTCCCGGCGCTGCTACTGCTCCTGCTGCTCCGGCCGCCGGCGACGCGGGGCATCA
CGTGCCCGCCCCCATGTCCGTGGAGCACGCAGACATCTGGGTCAAGAGCTACAGCTTGTAC
TCCCGGGAGCGGTACATCTGCAACTCGGGTTTCAAGCGGAAGGCCGGCACGTCCAGCCTGAC
```

| EXAMPLES OF SEQUENCES |
|---|
| GGAGTGCGTGTTGAACAAGGCCACGAATGTCGCCCACTGGACGACCCCCTCGCTCAAGTGCA
TCCGCGACCCGGCCCTGGTTCACCAGCGGCCCGCGCCACCCTCCACCGTAACGACGGCGGGG
GTGACCCCGCAGCCGGAGAGCCTCTCCCCGTCGGGAAAGGAGCCCCGCCGCGTCGTCGCCCAG
CTCGAACAACACGGCGGCCACAACTGCAGCGATCGTCCCGGGCTCCCAGCTGATGCCGTCGA
AGTCGCCGTCCACGGGAACCACGGAGATCAGCAGTCATGAGTCCTCCCACGGCACCCCCTCG
CAAACGACGGCCAAGAACTGGGAACTCACGGCGTCCGCCTCCCACCAGCCGCCGGGGGTGTA
TCCGCAAGGCCACAGCGACACCACGCCGAAGTCCTGCGACAAGACGCACACGTGCCCTCCCT
GCCCGGCGCCCGAGCTGCTGGGAGGTCCGAGCGTGTTCCTCTTCCCGCCCAAGCCGAAGGAC
ACGCTCATGATCTCGCGGACTCCCGAGGTCACCTGCGTCGTGGTAGACGTCAGCCACGAGGA
CCCGGAGGTCAAGTTCAACTGGTACGTTGACGGCGTAGAGGTGCACAACGCGAAGACGAAGC
CGCGGGAGGAGCAGTACAACTCGACGTACCGAGTCGTGTCGGTCCTGACCGTCCTGCACCAG
GACTGGCTCAACGGGAAGGAGTACAAGTGCAAGGTGTCGAACAAGGCGCTCCCTGCCCCGAT
CGAGAAGACGATCTCGAAGGCGAAGGGCCAGCCCAGGGAGCCCCAGGTCTACACGCTCCCGC
CATCGCGGGACGAGCTGACGAAGAACCAGGTTTCCCTGACGTGCCTCGTCAAGGGCTTCTAC
CCATCGGACATCGCGGTGGAGTGGGAGAGCAACGGGCAGCCGGAGAACAACTACAAGACCAC
GCCTCCGGTGCTCGACTCGGACGGGTCGTTCTTCCTCTACTCGAAGCTGACCGTCGACAAGA
GCCGGTGGCAGCAGGGCAACGTGTTCTCCTGCTCGGTGATGCACGAGGCCCTCCACAACCAC
TACACCCAGAAGTCGCTCAGTCTGAGCCCGGGGAAGTAATGAggatccgaattcgcggatat
cggttaacggatccagatctgctgtgccttctagttgccagccatctgttgtttgccccctcc
cccgtgccttccttgaccctggaaggtgccactcccactgtcctttcctaataaaatgagga
aattgcatcgcattgtctgagtaggtgtcattctattctgggggtggggtggggcaggaca
gcaaggggggaggattgggaagacaatagcaggcatgctgggatgcggtgggctctatgggt
acccaggtgctgaagaattgacccggttcctcctgggccagaaagaagcaggcacatcccct
tctctgtgacacaccctgtccacgcccctggttcttagttccagcccactcataggacact
catagctcaggagggctccgccttcaatcccaccccgctaaagtacttggagcggtctctccc
tccctcatcagcccaccaaaccaaacctagcctccaagagtgggaagaaattaaagcaagat
aggctattaagtgcagagggagagaaaatgcctccaacatgtgaggaagtaatgagagaaat
catagaatttcttccgcttcctcgctcactgactcgctgcgctcggtcgttcggctgcggcg
agcggtatcagctcactcaaaggcggtaatacggttatccacagaatcagggggataacgcag
gaaagaacatgtgagcaaaaggccagcaaaaggccaggaaccgtaaaaaggccgcgttgctg
gcgtttttccataggctccgcccccctgacgagcatcacaaaaatcgacgctcaagtcagag
gtggcgaaacccgacaggactataaagataccaggcgtttccccctggaagctccctcgtgc
gctctcctgttccgaccctgccgcttaccggatacctgtccgcctttctcccttcgggaagc
gtggcgctttctcatagctcacgctgtaggtatctcagttcggtgtaggtcgttcgctccaa
gctgggctgtgtgcacgaacccccccgttcagcccgaccgctgcgccttatccggtaactatc
gtcttgagtccaacccggtaagacacgacttatcgccactggcagcagccactggtaacagg
attagcagagcgaggtatgtaggcggtgctacagagttcttgaagtggtggcctaactacgg
ctacactagaagaacagtatttggtatctgcgctctgctgaagccagttaccttcggaaaaa
gagttggtagctcttgatccggcaaacaaaccaccgctggtagcggtggtttttttgtttgc
aagcagcagattacgcgcagaaaaaaaggatctcaagaagatcctttgatcttttctacggg
gtctgacgctcagtggaacgaaaact
cacgttaagggattttggtcatgagattatcaaaaaggatcttcacctagatccttttaaat
taaaaatgaagttttaaatcaatctaaagtatatatgagtaaacttggtctgacagttacca
atgcttaatcagtgaggcacctatctcagcgatctgtctatttcgttcatccatagttgcct
gactcgggggggggggcgctgaggtctgcctcgtgaagaaggtgttgctgactcataccag
gcctgaatcgccccatcatccagccagaaagtgagggagccacggttgatgagagctttgtt
gtaggtggaccagttggtgattttgaacttttgctttgccacggaacggtctgcgttgtcgg
gaagatgcgtgatctgatccttcaactcagcaaaagttcgatttattcaacaaagccgccgt
cccgtcaagtcagcgtaatgctctgccagtgttacaaccaattaaccaattctgattagaaa
aactcatcgagcatcaaatgaaactgcaatttattcatatcaggattatcaataccatattt
ttgaaaaagccgtttctgtaatgaaggagaaaactcaccgaggcagttccataggatggcaa
gatcctggtatcggtctgcgattccgactcgtccaacatcaatacaacctattaatttcccc
tcgtcaaaaataaggttatcaagtgagaaatcaccatgagtgacgactgaatccggtgagaa
tggcaaaagcttatgcatttctttccagacttgttcaacaggccagccattacgctcgtcat
caaaatcactcgcatcaaccaaaccgttattcattcgtgattgcgcctgagcgagacgaaat
acgcgatcgctgttaaaaggacaattacaaacaggaatcgaatgcaaccggcgcaggaacac
tgccagcgcatcaacaatattttcacctgaatcaggatattcttctaatacctggaatgctg
ttttcccggggatcgcagtggtgagtaaccatgcatcatcaggagtacggataaaatgcttg
atggtcggaagaggcataaattccgtcagccagtttagtctgaccatctcatctgtaacatc
attggcaacgctacctttgccatgtttcagaaacaactctggcgcatcgggcttcccataca
atcgatagattgtcgcacctgattgcccgacattatcgcgagcccatttatacccatataaa
tcagcatccatgttggaatttaatcgcggcctcgagcaagacgtttcccgttgaatatggct
cataacacccccttgtattactgtttatgtaagcagacagttttattgttcatgatgatatat
ttttatcttgtgcaatgtaacatcagagattttgagacacaacgtggatcatccagacatga
taagatacattgatgagtttggacaaaccacaactagaatgcagtgaaaaaaatgctttatt
tgtgaaatttgtgatgctattgctttatttgtaaccattataagctgcaataaacaagttaa
caacaacaattgcattcatttttatgttttcaggttcagggggagggtgggaggtttttaaa
gcaagtaaaacctacaaatggtatggctgattatgatcgtcgaggatctggatccgtt
aaccgatatccgcgaattcggcgcgccgggccoTCACGACGTGTTGATGAACATCTGGACGA
TGTGCACGAACGACTGCAGGAACTCCTTGATGTTCTTCTCCTCCAGCTCCTCGCACTCCTTG
CAGCCCGACTCCGTGACGTTCCCGTTCGACGACAGCGAGTTGTTCGCCAGGATGATCAGGTT
CTCCACCGTGTCGTGGATCGACGCGTCCCCCGACTCGAGCGAGATGACTTGGAGCTCCAGGA
GGAAGCACTTCATCGCCGTGACCTTGCACGACGGGTGGACGTCCGACTCCGTGTACAGCGTC
GCGTCGATGTGCATCGACTGGATGAGGTCCTCGATCTTCTTCAGGTCCGAGATCACGTTCAC
CCAGTTCGAGATGCTGCAGGCCACCGTCCCCAGGAGTAGCAGGCTCTGGAGCCACATttctt
gtcgacagatccaaacgctcctccgacgtcccaggcagaatggcggttccctaaacgagca
ttgcttatatagacctcccattaggcacgcctaccgcccatttacgtcaatggaacgccat |

EXAMPLES OF SEQUENCES ttgcgtcattgcccctcccattgacgtcaatggggatgtacttggcagccatcgcgggcca
tttaccgccattgacgtcaatgggagtactgccaatgtaccctggcgtacttccaatagtaa
tgtacttgccaagttactattaatagatattgatgtactgccaagtgggccatttaccgtca
ttgacgtcaataggggcgtgagaacggatatgaatgggcaatgagccatcccattgacgtc
aatggtgggtggtcctattgacgtcaatgggcattgagccaggcgggccatttaccgtaatt
gacgtcaatggggaggcgccatatacgtcaataggaccgcccatatgacgtcaataggtaa
gaccatgaggccctttcgtctcgcgcgtttcggtgatgacggtgaaaacctctgacacatgc
agctcccggagacggtcacagcttgtctgtaagcggatgccgggagcagacaagcccgtcag
ggcgcgtcagcgggtgttggcgggtgtcggggctggcttaactatgcggcatcagagcagat
tgtactgagagtgcaccatatgcggtgtgaaataccgcacagatgcgtaaggagaaaatacc
gcatcagattggctattgg SEQ ID NO: 17-huIL15sRa205-Fc-underlined region is IL15sRa sequence <u>M A P R R A R G C R T L G L P A L L L L L
L L R P P A T R G I T C P P P M S V E H A
D I W V K S Y S L Y S R E R Y I C N S G F
K R K A G T S S L T E C V L N K A T N V A
H W T T P S L K C I R D P A L V H Q R P A
P P S T V T T A G V T P Q P E S L S P S G
K E P A A S S P S S N N T A A T T A A I V
P G S Q L M P S K S P S T G T T E I S S H
E S S H G T P S Q T T A K N W E L T A S A</u>
S H Q P P G V Y P Q G H S D T T P K S C D
K T H T C P P C P A P E L L G G P S V F L
F P P K P K D T L M I S R T P E V T C V V
V D V S H E D P E V K F N W Y V D G V E V
H N A K T K P R E E Q Y N S T Y R V V S V
L T V L H Q D W L N G K E Y K C K V S N K
A L P A P I E K T I S K A K G Q P R E P Q
V Y T L P P S R D E L T K N Q V S L T C L
V K G F Y P S D I A V E W E S N G Q P E N
N Y K T T P P V L D S D G S F F L Y S K L
T V D K S R W Q Q G N V F S C S V M H E A
L H N H Y T Q K S L S L S P G K SEQ ID NO: 18--huGMCSF-IL15
M W L Q S L L L L G T V A C S I S N W V N
V I S D L K K I E D L I Q S M H I D A T L
Y T E S D V H P S C K V T A M K C F L L E
L Q V I S L E S G D A S I H D T V E N L I
I L A N N S L S S N G N V T E S G C K E C
E E L E E K N I K E F L Q S F V H I V Q M
F I N T S SEQ ID NO: 19--AG256DPhuIL15sRa200FC-FhuGMIL15-The capitalized, bolded region is the coding region for the IL-15Receptor alpha 200FC fusion
cctggccattgcatacgttgtatccatatcataatatgtacatttatattggctcatgtcca
acattaccgccatgttgacattgattattgactagttattaatagtaatcaattacggggtc
attagttcatagcccatatatggagttccgcgttacataacttacggtaaatggcccgcctg
gctgaccgcccaacgaccccgcccattgacgtcaataatgacgtatgttcccatagtaacg
ccaatagggactttccattgacgtcaatgggtggagtatttacggtaaactgcccacttggc
agtacatcaagtgtatcatatgccaagtacgccccctattgacgtcaatgatggtaaatggc
ccgcctggcattatgcccagtacatgaccttatgggactttcctacttggcagtacatctac
gtattagtcatcgctattaccatggtgatgcggttttggcagtacatcaatgggcgtggata
gcggtttgactcacggggatttccaagtctccaccccattgacgtcaatgggagtttgtttt
ggcaccaaaatcaacgggactttccaaaatgtcgtaacaactccgccccattgacgcaaatg
ggcggtaggcgtgtacggtgggaggtctatataagcagagctcgtttagtgaaccgtcagat
cgcctggagacgccatccacgctgttttgacctccatagaagacaccgggaccgatccagcc
tccgcgggcgcgtcgacgctagcaagaaATGGCCCCGAGGCGGGCGCGAGGCTGCCGGAC
CCTCGGTCTCCCGGCGCTGCTACTGCTCCTGCTGCTCCGGCCGCCGGCGACGCGGGGCATCA
CGTGCCCGCCCCCCATGTCCGTGGAGCACGCAGACATCTGGGTCAAGAGCTACAGCTTGTAC
TCCCGGGAGCGGTACATCTGCAACTCGGGTTTCAAGCGGAAGGCCGGCACGTCCAGCCTGAC
GGAGTGCGTGTTGAACAAGGCCACGAATGTCGCCCACTGGACGACCCCCTCGCTCAAGTGCA
TCCGCGACCCGGCCCTGGTTCACCAGCGGCCCGCGCCACCCTCCACCGTAACGACGGCGGG
GTGACCCCGCAGCCGGAGAGCCTCTCCCCGTCGGGAAAGGAGCCCGCCGCGTCGTCGCCCAG
CTCGAACAACACGGCGCCACAACTGCAGCGATCGTCCCGGGCTCCCAGCTGATGCCGTCGA
AGTCGCCGTCCACGGGAACCACGGAGATCAGCAGTCATGAGTCCTCCCACGGCACCCCCTCG
CAAACGACGGCCAAGAACTGGGAACTCACGGCGTCCGCCTCCCACCAGCCGCCGGGGGTGTA
TCCGCAAGGCCCGAAGTCCTGCGACAAGACGCACACGTGCCCTCCCTGCCCGGCGCCCGAGC
TGCTGGGAGGTCCGAGCGTGTTCCTCTTCCCGCCCAAGCCGAAGGACACGCTCATGATCTCG
CGGACTCCCGAGGTCACCTGCGTCGTGGTAGACGTCAGCCACGAGGACCCGGAGGTCAAGTT
CAACTGGTACGTTGACGGCGTAGAGGTGCACAACGCGAAGACGAAGCCGCGGGAGGAGCAGT
ACAACTCGACGTACCGAGTCGTGTCGGTCCTGACCGTCCTGCACCAGGACTGGCTCAACGGG
AAGGAGTACAAGTGCAAGGTGTCGAACAAGGCGCTCCCTGCCCCGATCGAGAAGACGATCTC
GAAGGCGAAGGGCCAGCCCAGGGAGCCCCAGGTCTACACGCTCCCGCCATCGCGGGACGAGC

EXAMPLES OF SEQUENCES

```
TGACGAAGAACCAGGTTTCCCTGACGTGCCTCGTCAAGGGCTTCTACCCATCGGACATCGCG
GTGGAGTGGGAGAGCAACGGGCAGCCGGAGAACAACTACAAGACCACGCCTCCGGTGCTCGA
CTCCGACGGGTCGTTCTTCCTCTACTCGAAGCTGACCGTCGACAAGAGCCGGTGGCAGCAGG
GCAACGTGTTCTCCTGCTCGGTGATGCACGAGGCCCTCCACAACCACTACACCCAGAAGTCG
CTCAGTCTGAGCCCGGGGAAGTAATGAggatccgaattcgcggatatcggttaacggatcca
gatctgctgtgccttctagttgccagccatctgttgtttgccccccccgtgccttccttg
accctggaaggtgccactcccactgtcctttcctaataaaatgaggaaattgcatcgcattg
tctgagtaggtgtcattctattctgggggtgggggtggggcaggacagcaaggggggaggatt
gggaagacaatagcaggcatgctggggatgcggtgggctctatgggtacccaggtgctgaag
aattgacccggttcctcctgggccagaaagaagcaggcacatccccttctctgtgacacacc
ctgtccacgccctggttcttagttccagcccactcataggacactcatagctcaggaggg
ctccgccttcaatcccaccgctaaagtacttggagcggtctctccctccctcatcagccca
ccaaaccaaacctagcctccaagagtgggaagaaattaaagcaagataggctattaagtgca
gagggagagaaaatgcctccaacatgtgaggaagtaatgagagaaatcatagaatttcttcc
gcttcctcgctcactgactcgctgcgctcggtcgttcggctgcggcgagcggtatcagctca
ctcaaaggcggtaatacggttatccacagaatcagggataacgcaggaaagaacatgtgag
caaaaggccagcaaaaggccaggaaccgtaaaaaggccgcgttgctggcgtttttccatagg
ctccgcccccctgacgagcatcacaaaaatcgacgctcaagtcagaggtggcgaaacccgac
aggactataaagataccaggcgtttccccctggaagctccctcgtgcgctctcctgttccga
ccctgccgcttaccggatacctgtccgcctttctcccttcgggaagcgtggcgctttctcat
agctcacgctgtaggtatctcagttcggtgtaggtcgttcgctccaagctgggctgtgtgca
cgaaccccccgttcagcccgaccgctgcgccttatccggtaactatcgtcttgagtccaacc
cggtaagacacgacttatcgccactggcagcagccactggtaacaggattagcagagcgagg
tatgtaggcggtgctacagagttcttgaagtggtggcctaactacggctacactagaagaac
agtatttggtatctgcgctctgctgaagccagttaccttcggaaaaagagttggtagctctt
gatccggcaaacaaaccaccgctggtagcggtggtttttttgtttgcaagcagcagattacg
cgcagaaaaaaaggatctcaagaagatcctttgatcttttctacggggtctgacgctcagtg
gaacgaaaactcacgttaagggattttggtcatgagattatcaaaaaggatcttcacctaga
tccttttaaattaaaaatgaagttttaaatcaatctaaagtatatatgagtaaacttggtct
gacagttaccaatgcttaatcagtgaggcacctatctcagcgatctgtctatttcgttcatc
catagttgcctgactcgggggggggggcgctgaggtctgcctcgtgaagaaggtgttgctg
actcataccaggcctgaatcgccccatcatccagccagaaagtgagggagccacggttgatg
agagctttgttgtaggtggaccagttggtgattttgaacttttgctttgccacggaacggtc
tgcgttgtcgggaagatgcgtgatctgatccttcaactcagcaaaagttcgatttattcaac
aaagccgccgtcccgtcaagtcagcgtaatgctctgccagtgttacaaccaattaaccaatt
ctgattagaaaaactcatcgagcatcaaatgaaactgcaatttattcatatcaggattatca
ataccatattttgaaaaagccgtttctgtaatgaaggagaaaacttcaccgaggcagttcca
taggatggcaagatcctggtatcggtctgcgattccgactcgtccaacatcaatacaaccta
ttaatttcccctcgtcaaaaataaggttatcaagtgagaaatcaccatgagtgacgactgaa
tccggtgagaatggcaaaagcttatgcatttctttccagacttgttcaacaggccagccatt
acgctcgtcatcaaaatcactcgcatcaaccaaaccgttattcattcgtgattgcgcctgag
cgagacgaaatacgcgatcgctgttaaaaggacaattacaaacaggaatcgaatgcaaccgg
cgcaggaacactgccagcgcatcaacaatattttcacctgaatcaggatattcttctaatac
ctggaatgctgtttttcccggggatcgcagtggtgagtaaccatgcatcatcaggagtacgga
taaaatgcttgatggtcggaagaggcataaattccgtcagccagtttagtctgaccatctca
tctgtaacatcattggcaacgctacctttgccatgtttcagaaacaactctggcgcatcggg
cttcccatacaatcgatagattgtcgcacctgattgcccgacattatcgcgagcccatttat
acccatataaatcagcatccatgttggaatttaatcgcggcctcgagcaagacgtttcccgt
tgaatatggctcataacaccccttgtattactgtttatgtaagcagacagttttattgttca
tgatgatatattttatcttgtgcaatgtaacatcagagattttgagacacaacgtggatca
tccagacatgataagatacattgatgagtttggacaaaccacaactagaatgcagtgaaaaa
aatgctttatttgtgaaatttgtgatgctattgctttatttgtaaccattataagctgcaat
aaacaagttaacaacaacaattgcattcattttatgtttcaggttcagggggaggtgtggga
ggttttttaaagcaagtaaaacctctacaaatgtggtatggctgattatgatcgtcgaggat
ctggatccgttaaccgatatccgcgaattcggcgcgccgggcccTCACGACGTGTTGATGAA
CATCTGGACGATGTGCACGAACGACTGCAGGAACTCCTTGATGTTCTTCTCCTCCAGCTCCT
CGCACTCCTTGCAGCCCGACTCCGTGACGTTCCCGTTCGACGACAGCGAGTTGTTCGCCAGG
ATGATCAGGTTCTCCACCGTGTCGTGGATCGACGCGTCCCCGACTCGAGCGAGATGACTTG
GAGCTCCAGGAGGAAGCACTTCATCGCCGTGACCTTGCACGACGGGTGGACGTCCGACTCCG
TGTACAGCGTCGCGTCGATGTGCATCGACTGGATGAGGTCCTCGATCTTCTTCAGGTCCGAG
ATCACGTTCACCCAGTTCGAGATGCTGCAGGCCACCGTCCCCAGGAGTAGCAGGCTCTGGAG
CCACATttcttgtcgacagatccaaacgctcctccgacgtccccaggcagaatggcggttcc
ctaaacgagcattgcttatatagacctcccattaggcacgcctaccgcccatttacgtcaat
ggaacgccccatttgcgtcattgccccctccccattgacgtcaatggggatgtacttggcagcc
atcgcgggccatttaccgccattgacgtcaatgggagtactgccaatgtaccctggcgtact
tccaatagtaatgtacttgccaagttactattaatagatattgatgtactgccaagtgggcc
atttaccgtcattgacgtcaataggggcgtgagaacggatatgaatgggcaatgagccatc
ccattgacgtcaatggtgggtggtcctattgacgtcaatgggcattgagccaggcggccat
ttaccgtaattgacgtcaatggggaggcgccatatacgttaataggaaccgcccatatgacg
tcaataggtaagaccatgaggccctttcgtctcgcgcgtttcggtgatgacggtgaaaacct
ctgacacatgcagctcccggagacggtcacagcttgtctgtaagcggatgccgggagcagac
aagcccgtcagggcgcgtcagcgggtgttggcgggtgtcggggctggcttaactatgcggca
tcagagcagattgtactgagagtgcaccatatgcggtgtgaaataccgcacagatgcgtaag
gagaaaataccgcatcagattggctattgg
```

EXAMPLES OF SEQUENCES

SEQ ID NO: 20--huIL15sRa200-Fc

M A P R R A R G C R T L G L P A L L L L L
L L R P P A T R G I T C P P P M S V E H A
D I W V K S Y S L Y S R E R Y I C N S G F
K R K A G T S S L T E C V L N K A T N V A
H W T T P S L K C I R D P A L V H Q R P A
P P S T V T T A G V T P Q P E S L S P S G
K E P A A S S P S S N N T A A T T A A I V
P G S Q L M P S K S P S T G T T E I S S H
E S S H G T P S Q T T A K N W E L T A S A
S H Q P P G V Y P Q G P K S C D K T H T C
P P C P A P E L L G G P S V F L F P P K P
K D T L M I S R T P E V T C V V V D V S H
E D P E V K F N W Y V D G V E V H N A K T
K P R E E Q Y N S T Y R V V S V L T V L H
Q D W L N G K E Y K C K V S N K A L P A P
I E K T I S K A K G Q P R E P Q V Y T L P
P S R D E L T K N Q V S L T C L V K G F Y
P S D I A V E W E S N G Q P E N N Y K T T
P P V L D S D G S F F L Y S K L T V D K S
R W Q Q G N V F S C S V M H E A L H N H Y
T Q K S L S L S P G K

What is claimed is:

1. An IL-15/IL-15Rα-Fc heterodimer comprising IL-15Rα-Fc bound to IL-15, wherein the IL-15Rα-Fc comprises the amino acids 31 to 431 of SEQ ID NO:20.

2. The IL-15/IL-15Rα-Fc heterodimer of claim 1, wherein the IL-15 comprises an amino sequence that is at least 95% identical to amino acids 49 to 162 of SEQ ID NO:2.

3. The IL-15/IL-15Rα-Fc heterodimer of claim 2, wherein the IL-15 comprises an amino acid sequence of amino acids 49 to 162 of SEQ ID NO:2.

4. A composition comprising the IL-15/IL-15Rα-Fc heterodimer of claim 1.

5. The composition of claim 4, further comprising a chemotherapeutic agent.

6. The composition of claim 5, wherein the chemotherapeutic agent is an anticancer agent.

7. The composition of claim 6, wherein the anticancer agent is a chemical agent.

8. The composition of claim 7, wherein the chemical agent is vinblastine, fludarabine, aclarubicin, doxorubicin, exemestane, alefacept, alemtuzumab, pamidronate, idarubicin, or cyclophosphamide.

9. The composition of claim 5, further comprising a glucocorticoid.

10. The composition of claim 4, wherein the composition is formulated for intravenous, intramuscular, subcutaneous, intradermal, intranasal, or inhalational delivery.

11. The composition of claim 4, wherein the composition is administered daily, weekly, bi-weekly, monthly, or as needed.

12. The composition of claim 4, further comprising a glucocorticoid.

* * * * *

SEQUENCE LISTING

<160> NUMBER OF SEQ ID NOS: 20

<210> SEQ ID NO 1
<211> LENGTH: 489
<212> TYPE: DNA
<213> ORGANISM: Homo sapiens
<220> FEATURE:
<223> OTHER INFORMATION: human wild-type interleukin-15 (IL-15)

<400> SEQUENCE: 1

```
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca aagtaacagc aatgaagtgc tttctcttgg agttacaagt tatttcactt     300
gagtctggag atgcaagtat tcatgataca gtagaaaatc tgatcatcct agcaaacaac     360
agtttgtctt ctaatgggaa tgtaacagaa tctggatgca agaatgtga ggaactggag      420 gaaaaaaata ttaaagaatt tttgcagagt tttgtacata ttgtccaaat gttcatcaac     480
acttcttga                                                            489
```

<210> SEQ ID NO 2
<211> LENGTH: 162
<212> TYPE: PRT
<213> ORGANISM: Homo sapiens
<220> FEATURE:
<223> OTHER INFORMATION: human wild-type interleukin-15 (IL-15)

<400> SEQUENCE: 2

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

```
Asn Trp Val Asn Val Ile Ser Asp Leu Lys Lys Ile Glu Asp Leu Ile
 50                  55                  60
Gln Ser Met His Ile Asp Ala Thr Leu Tyr Thr Glu Ser Asp Val His
 65                  70                  75                  80
Pro Ser Cys Lys Val Thr Ala Met Lys Cys Phe Leu Leu Glu Leu Gln
                 85                  90                  95
Val Ile Ser Leu Glu Ser Gly Asp Ala Ser Ile His Asp Thr Val Glu
            100                 105                 110
Asn Leu Ile Ile Leu Ala Asn Asn Ser Leu Ser Ser Asn Gly Asn Val
            115                 120                 125
Thr Glu Ser Gly Cys Lys Glu Cys Glu Glu Leu Glu Glu Lys Asn Ile
130                 135                 140
Lys Glu Phe Leu Gln Ser Phe Val His Ile Val Gln Met Phe Ile Asn
145                 150                 155                 160
Thr Ser

<210> SEQ ID NO 3
<211> LENGTH: 489
<212> TYPE: DNA
<213> ORGANISM: Artificial Sequence
<220> FEATURE:
<223> OTHER INFORMATION: synthetic improved human interleukin-15 (IL-15)
      (opt1)

<400> SEQUENCE: 3
atgcggatct cgaagccgca cctgcggtcg atatcgatcc agtgctacct gtgcctgctc      60
ctgaactcgc acttcctcac ggaggccggt atacacgtct tcatcctggg ctgcttctcg    120
gcggggctgc cgaagacgga ggcgaactgg gtgaacgtga tctcggacct gaagaagatc    180
gaggacctca tccagtcgat gcacatcgac gcgacgctgt acacggagtc ggacgtccac    240
ccgtcgtgca aggtcacggc gatgaagtgc ttcctcctgg agctccaagt catctcgctc    300
gagtcggggg acgcgtcgat ccacgacacg gtggagaacc tgatcatcct ggcgaacaac    360
tcgctgtcgt cgaacgggaa cgtcacggag tcgggctgca aggagtgcga ggagctggag    420
gagaagaaca tcaaggagtt cctgcagtcg ttcgtgcaca tcgtccagat gttcatcaac    480
acgtcgtga                                                            489

<210> SEQ ID NO 4
<211> LENGTH: 489
<212> TYPE: DNA
<213> ORGANISM: Artificial Sequence
<220> FEATURE:
<223> OTHER INFORMATION: synthetic improved human interleukin-15 (IL-15)
      (opt2)

<400> SEQUENCE: 4
atgaggatca gcaagcccca cctgaggagc atcagcatcc agtgctacct gtgcctgctg      60
ctgaacagcc acttcctgac cgaggccggt atacacgtgt tcatcctggg ctgctttagc    120
gccggactgc ccaagaccga ggccaattgg gtgaacgtga tcagcgacct gaagaagatc    180
gaggacctca tccagagcat gcacatcgac gccaccctgt acaccgagag cgatgtgcac    240
cccagctgta aggtgaccgc catgaagtgc tttctgctgg agctgcaagt gatcagcctg    300
gagagcggcg acgccagcat ccacgacacc gtggagaacc tgatcatcct ggccaacaac    360
agcctgagca gcaacggcaa tgtgaccgag agcggctgta aggagtgtga ggagctggag    420
```

```
gagaagaaca tcaaggagtt tctgcagagc ttcgtgcaca tcgtgcagat gttcatcaac    480
accagctga                                                             489

<210> SEQ ID NO 5
<211> LENGTH: 1610
<212> TYPE: DNA
<213> ORGANISM: Homo sapiens
<220> FEATURE:
<223> OTHER INFORMATION: human interleukin-15 receptor, alpha (IL15RA),
      transcript variant 1 cDNA
<220> FEATURE:
<221> NAME/KEY: CDS
<222> LOCATION: (83)..(886)
<223> OTHER INFORMATION: interleukin-15 receptor, alpha (IL15RA),
      isoform 1 precursor

<400> SEQUENCE: 5
cccagagcag cgctcgccac ctccccccgg cctgggcagc gctcgcccgg ggagtccagc     60
ggtgtcctgt ggagctgccg ccatggcccc gcggcgggcg cgcggctgcc ggaccctcgg    120
tctcccggcg ctgctactgc tgctgctgct ccggccgccg cgacgcggg gcatcacgtg    180 ccctcccccc atgtccgtgg aacacgcaga catctgggtc aagagctaca gcttgtactc    240
cagggagcgg tacatttgta actctggttt caagcgtaaa gccggcacgt ccagcctgac    300
ggagtgcgtg ttgaacaagg ccacgaatgt cgcccactgg acaacccca gtctcaaatg    360 cattagagac cctgccctgg ttcaccaaag gccagcgcca ccctccacag taacgacggc    420
aggggtgacc ccacagccag agagcctctc cccttctgga aaagagcccg cagcttcatc    480
tcccagctca acaacacag cggccacaac agcagctatt gtcccgggct cccagctgat    540
gccttcaaaa tcaccttcca caggaaccac agagataagc agtcatgagt cctcccacgg    600 cacccccctct cagacaacag ccaagaactg gaaactcaca gcatccgcct cccaccagcc    660
gccaggtgtg tatccacagg ccacagcga caccactgtg gctatctcca cgtccactgt    720
cctgctgtgt gggctgagcg ctgtgtctct cctggcatgc tacctcaagt caaggcaaac    780
tcccccgctg ccagcgttg aaatggaagc catggaggct ctgccggtga cttgggggac    840
cagcagcaga gatgaagact tggaaaactg ctctcaccac ctatgaaact cggggaaacc    900
agcccagcta agtccggagt gaaggagcct ctctgcttta gctaaagacg actgagaaga    960
ggtgcaagga agcgggctcc aggagcaagc tcaccaggcc tctcagaagt cccagcagga   1020
tctcacggac tgccgggtcg gcgcctcctg cgcgagggag caggttctcc gcattcccat   1080
gggcaccacc tgcctgcctg tcgtgccttg gacccagggc ccagcttccc aggagagacc   1140
aaaggcttct gagcaggatt tttatttcat tacagtgtga gctgcctgga atacatgtgg   1200
taatgaaata aaaaccctgc ccgaatcttc ccgtccctca tcctaacttt cagttcacag   1260
agaaaagtga catacccaaa gctctctgtc aattacaagg cttctcctgg cgtgggagac   1320
gtctacaggg aagacaccag cgtttgggct tctaaccacc tgtctccag ctgctctgca   1380 cacatggaca gggacctggg aaaggtggga gagatgctga gcccagcgaa tcctctccat   1440
tgaaggattc aggaagaaga aaactcaact cagtgccatt ttacgaatat atgcgtttat   1500
atttatactt ccttgtctat tatatctata cattatatat tatttgtatt ttgacattgt   1560
accttgtata aacaaaataa aacatctatt ttcaatattt ttaaaatgca              1610

<210> SEQ ID NO 6
<211> LENGTH: 267
<212> TYPE: PRT
<213> ORGANISM: Homo sapiens
```

<220> FEATURE:
<223> OTHER INFORMATION: human interleukin-15 receptor, alpha (IL15RA), isoform 1 precursor

<400> SEQUENCE: 6

```
Met Ala Pro Arg Arg Ala Arg Gly Cys Arg Thr Leu Gly Leu Pro Ala
1               5                   10                  15

Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

<210> SEQ ID NO 7
<211> LENGTH: 1843
<212> TYPE: DNA
<213> ORGANISM: Homo sapiens
<220> FEATURE:
<223> OTHER INFORMATION: human interleukin-15 receptor, alpha (IL15RA), transcript variant 2 cDNA
<220> FEATURE:
<221> NAME/KEY: CDS
<222> LOCATION: (424)..(1119)
<223> OTHER INFORMATION: interleukin-15 receptor, alpha (IL15RA), isoform 2

<400> SEQUENCE: 7

```
caggaattcg gcgaagtggc ggagctgggg ccccagcggg cgccgggggc gcgggagcc        60 agcaggtggc gggggctgcg ctccgcccgg gccagcgcgc accaggcagg tgcccgcgcc      120
tccgcaccgc ggcgacacct ccgcgggcac tcacccaggc cggccgctca caaccgagcg      180
```

```
cagggccgcg agggagacc aggaaagccg aaggcggagc agctggaggc gaccagcgcc    240
gggcgaggtc aagtggatcc gagccgcaga gaggctgga gagagtctgc tctccgatga    300
ctttgcccac tctcttcgca gtggggacac cggaccgagt gcacactgga ggtcccagag    360
cacgacgagc gcggaggacc gggaggctcc cgggcttgcg tgggcatcac gtgccctccc    420
cccatgtccg tggaacacgc agacatctgg gtcaagagct acagcttgta ctccagggag    480
cggtacattt gtaactctgg tttcaagcgt aaagccggca cgtccagcct gacggagtgc    540
gtgttgaaca aggccacgaa tgtcgccac tggacaaccc ccagtctcaa atgcattaga    600
gaccctgccc tggttcacca aaggccagcc cacccctcca cagtaacgac ggcaggggtg    660
accccacagc cagagagcct ctcccccttct ggaaaagagc ccgcagcttc atctcccagc    720
tcaaacaaca cagcggccac aacagcagct attgtcccgg gctcccagct gatgccttca    780
aaatcacctt ccacaggaac cacagagata agcagtcatg agtcctccca cggcaccccc    840
tctcagacaa cagccaagaa ctgggaactc acagcatccg cctcccacca gccgccaggt    900
gtgtatccac agggccacag cgacaccact gtggctatct ccacgtccac tgtcctgctg    960
tgtgggctga gcgctgtgtc tcctggca tgctacctca agtcaaggca aactcccccg    1020
ctggccagcg ttgaaatgga agccatggag gctctgccgg tgacttgggg gaccagcagc    1080
agagatgaag acttggaaaa ctgctctcac cacctatgaa actcggggaa accagcccag    1140
ctaagtccgg agtgaaggag cctctctgct ttagctaaag acgactgaga agaggtgcaa    1200
ggaagcgggc tccaggagca agctcaccag gcctctcaga agtcccagca ggatctcacg    1260
gactgccggg tcgcgcctc ctgcgcgagg gagcaggttc tccgcattcc catgggcacc    1320
acctgcctgc ctgtcgtgcc ttggacccag ggcccagctt cccaggagag accaaaggct    1380
tctgagcagg attttttattt cattacagtg tgagctgcct ggaatacatg tggtaatgaa    1440
ataaaaaccc tgccccgaat cttccgtccc tcatcctaac tttcagttca cagagaaaag    1500
tgacataccc aaagctctct gtcaattaca aggcttctcc tggcgtggga gacgtctaca    1560
gggaagacac cagcgtttgg gcttctaacc accctgtctc cagctgctct gcacacatgg    1620
acagggacct gggaaaggtg ggagagatgc tgagcccagc gaatcctctc cattgaagga    1680
ttcaggaaga agaaaactca actcagtgcc attttacgaa tatatgcgtt tatatttata    1740
cttccttgtc tattatatct atacattata tattatttgt attttgacat tgtaccttgt    1800
ataaacaaaa taaacatct attttcaata tttttaaaat gca                      1843
```

<210> SEQ ID NO 8
<211> LENGTH: 231
<212> TYPE: PRT
<213> ORGANISM: Homo sapiens
<220> FEATURE:
<223> OTHER INFORMATION: human interleukin-15 receptor, alpha (IL15RA), isoform 2

<400> SEQUENCE: 8

```
Met Ser Val Glu His Ala Asp Ile Trp Val Lys Ser Tyr Ser Leu Tyr
1               5                   10                  15

Ser Arg Glu Arg Tyr Ile Cys Asn Ser Gly Phe Lys Arg Lys Ala Gly
            20                  25                  30

Thr Ser Ser Leu Thr Glu Cys Val Leu Asn Lys Ala Thr Asn Val Ala
        35                  40                  45

His Trp Thr Thr Pro Ser Leu Lys Cys Ile Arg Asp Pro Ala Leu Val
    50                  55                  60
```

His Gln Arg Pro Ala Pro Pro Ser Thr Val Thr Thr Ala Gly Val Thr
 65                  70                  75                  80

Pro Gln Pro Glu Ser Leu Ser Pro Ser Gly Lys Glu Pro Ala Ala Ser
                 85                  90                  95

Ser Pro Ser Ser Asn Asn Thr Ala Ala Thr Thr Ala Ala Ile Val Pro
            100                 105                 110

Gly Ser Gln Leu Met Pro Ser Lys Ser Pro Ser Thr Gly Thr Thr Glu
        115                 120                 125

Ile Ser Ser His Glu Ser Ser His Gly Thr Pro Ser Gln Thr Thr Ala
130                 135                 140

Lys Asn Trp Glu Leu Thr Ala Ser Ala Ser His Gln Pro Pro Gly Val
145                 150                 155                 160

Tyr Pro Gln Gly His Ser Asp Thr Thr Val Ala Ile Ser Thr Ser Thr
                165                 170                 175

Val Leu Leu Cys Gly Leu Ser Ala Val Ser Leu Leu Ala Cys Tyr Leu
            180                 185                 190

Lys Ser Arg Gln Thr Pro Pro Leu Ala Ser Val Glu Met Glu Ala Met
        195                 200                 205

Glu Ala Leu Pro Val Thr Trp Gly Thr Ser Ser Arg Asp Glu Asp Leu
210                 215                 220

Glu Asn Cys Ser His His Leu
225                 230

<210> SEQ ID NO 9
<211> LENGTH: 807
<212> TYPE: DNA
<213> ORGANISM: Artificial Sequence
<220> FEATURE:
<223> OTHER INFORMATION: synthetic improved human interleukin-15 (IL-15)
      receptor alpha (IL15Ra), transcript variant 1 (OPT)

<400> SEQUENCE: 9 atggcccga ggcgggcgcg aggctgccgg accctcggtc tcccggcgct gctactgctc        60
ctgctgctcc ggccgccggc gacgcggggc atcacgtgcc cgcccccat gtccgtggag       120 cacgcagaca tctgggtcaa gagctacagc ttgtactccc gggagcggta catctgcaac       180
tcgggtttca gcggaaggc cggcacgtcc agcctgacgg agtgcgtgtt gaacaaggcc       240
acgaatgtcg cccactggac gaccccctcg ctcaagtgca tccgcgaccc ggccctggtt       300
caccagcggc ccgcgccacc ctccaccgta acgacggcgg gggtgacccc gcagccggag       360
agcctctccc cgtcgggaaa ggagcccgcc gcgtcgtcgc ccagctcgaa caacacggcg       420
gccacaactg cagcgatcgt cccgggctcc cagctgatgc cgtcgaagtc gccgtccacg       480
ggaaccacgg agatcagcag tcatgagtcc tcccacggca cccctcgca acgacggcc        540 aagaactggg aactcacggc gtccgcctcc accagccgc cggggtgta tccgcaaggc        600 cacagcgaca ccacggtggc gatctccacg tccacggtcc tgctgtgtgg gctgagcgcg       660
gtgtcgctcc tggcgtgcta cctcaagtcg aggcagactc cccgctggc cagcgttgag       720 atggaggcca tggaggctct gccggtgacg tgggggacca gcagcaggga tgaggacttg       780
gagaactgct cgcaccacct ataatga                                           807

<210> SEQ ID NO 10
<211> LENGTH: 267
<212> TYPE: PRT
<213> ORGANISM: Artificial Sequence
<220> FEATURE:
<223> OTHER INFORMATION: synthetic improved human interleukin-15 (IL-15)
      receptor alpha (IL15Ra), isoform 1 (OPT)

<400> SEQUENCE: 10

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

<210> SEQ ID NO 11
<211> LENGTH: 621
<212> TYPE: DNA
<213> ORGANISM: Artificial Sequence
<220> FEATURE:
<223> OTHER INFORMATION: synthetic improved human soluble interleukin-15
      (IL-15) receptor alpha (IL-15sRa) (OPT)

<400> SEQUENCE: 11

```
atggccccga ggcgggcgcg aggctgccgg accctcggtc tcccggcgct gctactgctc    60
ctgctgctcc ggccgccggc gacgcggggc atcacgtgcc cgcccccat gtccgtggag   120 cacgcagaca tctgggtcaa gagctacagc ttgtactccc gggagcggta catctgcaac   180
tcgggtttca gcggaaggc cggcacgtc agcctgacgg agtgcgtgtt gaacaaggcc    240
acgaatgtcg cccactggac gaccccctcg ctcaagtgca tccgcgaccc ggccctggtt   300
caccagcggc ccgcgccacc ctccaccgta acgacggcgg gggtgacccc gcagccggag   360
```

```
agcctctccc cgtcgggaaa ggagcccgcc gcgtcgtcgc ccagctcgaa caacacggcg    420
gccacaactg cagcgatcgt cccgggctcc cagctgatgc cgtcgaagtc gccgtccacg    480
ggaaccacgg agatcagcag tcatgagtcc tcccacggca ccccctcgca aacgacggcc    540
aagaactggg aactcacggc gtccgcctcc caccagccgc cggggggtgta tccgcaaggc    600 cacagcgaca ccacgtaatg a                                              621
```

<210> SEQ ID NO 12
<211> LENGTH: 205
<212> TYPE: PRT
<213> ORGANISM: Artificial Sequence
<220> FEATURE:
<223> OTHER INFORMATION: synthetic improved human soluble interleukin-15
      (IL-15) receptor alpha (IL-15sRa) (OPT)

<400> SEQUENCE: 12

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205
```

<210> SEQ ID NO 13
<211> LENGTH: 5958
<212> TYPE: DNA
<213> ORGANISM: Artificial Sequence
<220> FEATURE:
<223> OTHER INFORMATION: synthetic dual expression plasmid vector human
      IL15Ra+IL15

<400> SEQUENCE: 13

```
cctggccatt gcatacgttg tatccatatc ataatatgta catttatatt ggctcatgtc    60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
```

```
tagtaacgcc aatagggact ttccattgac gtcaatgggt ggagtattta cggtaaactg      300
cccacttggc agtacatcaa gtgtatcata tgccaagtac gcccctatt gacgtcaatg       360 acggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540 tcaatggag tttgttttgg caccaaaatc aacgggactt tccaaaatgt cgtaacaact      600
ccgccccatt gacgcaaatg gcggtaggc gtgtacggtg ggaggtctat ataagcagag      660
ctcgtttagt gaaccgtcag atcgcctgga cgccatcc acgctgtttt gacctccata       720
gaagacaccg ggaccgatcc agcctccgcg ggcgcgcgtc gaggaattcg ctagcaagaa     780
atggccccga ggcgggcgcg aggctgccgg accctcggtc tcccggcgct gctactgctc    840
ctgctgctcc ggccgccggc gacgcggggc atcacgtgcc cgcccccat gtccgtggag     900 cacgcagaca tctgggtcaa gagctacagc ttgtactccc gggagcggta catctgcaac     960
tcgggtttca gcggaaggc cggcacgtcc agcctgacgg agtgcgtgtt gaacaaggcc     1020
acgaatgtcg cccactggac gacccctcg ctcaagtgca tccgcgaccc ggccctggtt     1080
caccagcggc ccgcgccacc ctccaccgta acgacgcgg gggtgacccc gcagccggag    1140
agcctctccc cgtcgggaaa ggagcccgcc gcgtcgtcgc ccagctcgaa caacacggcg    1200
gccacaactg cagcgatcgt cccgggctcc cagctgatgc cgtcgaagtc gccgtccacg    1260
ggaaccacgg agatcagcag tcatgagtcc tcccacggca cccctcgca aacgacggcc    1320 aagaactggg aactcacggc gtccgcctcc caccagccgc cggggggtgta tccgcaaggc    1380 cacagcgaca ccacggtggc gatctccacg tccacggtcc tgctgtgtgg gctgagcgcg    1440
gtgtcgctcc tggcgtgcta cctcaagtcg aggcagactc cccgctggc cagcgttgag    1500 atggaggcca tggaggctct gccggtgacg tgggggacca gcagcaggga tgaggacttg    1560
gagaactgct cgcaccacct ataatgagaa ttcacgcgtg gatctgatat cggatctgct    1620
gtgccttcta gttgccagcc atctgttgtt tgcccctccc ccgtgccttc cttgaccctg    1680
gaaggtgcca ctcccactgt cctttcctaa taaaatgagg aaattgcatc gcattgtctg    1740
agtaggtgtc attctattct gggggtggg gtggggcagg acagcaaggg ggaggattgg    1800
gaagacaata gcaggcatgc tggggatgcg gtgggctcta tgggtaccca ggtgctgaag    1860
aattgacccg gttcctcctg ggccagaaag aagcaggcac atccccttct ctgtgacaca    1920
ccctgtccac gcccctggtt cttagttcca gccccactca taggacactc atagctcagg    1980
agggctccgc cttcaatccc acccgctaaa gtacttggag cggtctctcc ctccctcatc    2040
agcccaccaa accaaaccta gcctccaaga gtgggaagaa attaaagcaa gataggctat    2100
taagtgcaga gggagagaaa atgcctccaa catgtgagga agtaatgaga gaaatcatag    2160
aatttcttcc gcttcctcgc tcactgactc gctgcgctcg gtcgttcggc tgcggcgagc    2220
ggtatcagct cactcaaagg cggtaatacg gttatccaca gaatcagggg ataacgcagg    2280
aaagaacatg tgagcaaaag gccagcaaaa ggccaggaac cgtaaaaagg ccgcgttgct    2340 ggcgttttc cataggctcc gccccctga cgagcatcac aaaaatcgac gctcaagtca    2400
gaggtggcga aacccgacag gactataaag ataccaggcg tttcccctg gaagctccct    2460 cgtgcgctct cctgttccga ccctgccgct taccggatac ctgtccgcct ttctcccttc    2520
gggaagcgtg gcgctttctc aatgctcacg ctgtaggtat ctcagttcgg tgtaggtcgt    2580
tcgctccaag ctgggctgtg tgcacgaacc ccccgttcag cccgaccgct gcgccttatc    2640
```

```
cggtaactat cgtcttgagt ccaacccggt aagacacgac ttatcgccac tggcagcagc    2700
cactggtaac aggattagca gagcgaggta tgtaggcggt gctacagagt tcttgaagtg    2760
gtggcctaac tacggctaca ctagaaggac agtatttggt atctgcgctc tgctgaagcc    2820
agttaccttc ggaaaaagag ttggtagctc ttgatccggc aaacaaacca ccgctggtag    2880
cggtggtttt tttgtttgca agcagcagat tacgcgcaga aaaaaggat ctcaagaaga     2940 tcctttgatc ttttctacgg ggtctgacgc tcagtggaac gaaaactcac gttaagggat    3000
tttggtcatg agattatcaa aaaggatctt cacctagatc cttttaaatt aaaaatgaag    3060
ttttaaatca atctaaagta tatatgagta aacttggtct gacagttacc aatgcttaat    3120
cagtgaggca cctatctcag cgatctgtct atttcgttca tccatagttg cctgactcgg    3180 ggggggggg cgctgaggtc tgcctcgtga agaaggtgtt gctgactcat accaggcctg     3240
aatcgcccca tcatccagcc agaaagtgag ggagccacgg ttgatgagag ctttgttgta    3300
ggtggaccag ttggtgattt tgaactttg ctttgccacg gaacggtctg cgttgtcggg     3360
aagatgcgtg atctgatcct tcaactcagc aaaagttcga tttattcaac aaagccgccg    3420
tcccgtcaag tcagcgtaat gctctgccag tgttacaacc aattaaccaa ttctgattag    3480
aaaaactcat cgagcatcaa atgaaactgc aatttattca tatcaggatt atcaatacca    3540
tatttttgaa aaagccgttt ctgtaatgaa ggagaaaact caccgaggca gttccatagg    3600
atggcaagat cctggtatcg gtctgcgatt ccgactcgtc aacatcaat acaacctatt     3660 aatttcccct cgtcaaaaat aaggttatca agtgagaaat caccatgagt gacgactgaa    3720
tccggtgaga atggcaaaag cttatgcatt tctttccaga cttgttcaac aggccagcca    3780
ttacgctcgt catcaaaatc actcgcatca accaaaccgt tattcattcg tgattgcgcc    3840
tgagcgagac gaaatacgcg atcgctgtta aaaggacaat tacaaacagg aatcgaatgc    3900
aaccggcgca ggaacactgc cagcgcatca acaatatttt cacctgaatc aggatattct    3960 tctaataccct ggaatgctgt tttcccgggg atcgcagtgg tgagtaacca tgcatcatca    4020
ggagtacgga taaatgctt gatggtcgga agaggcataa attccgtcag ccagtttagt     4080
ctgaccatct catctgtaac atcattggca acgctacctt tgccatgttt cagaaacaac    4140
tctggcgcat cgggcttccc atacaatcga tagattgtcg cacctgattg cccgacatta    4200
tcgcgagccc atttataccc atataaatca gcatccatgt tggaatttaa tcgcggcctc    4260
gagcaagacg tttcccgttg aatatggctc ataacacccc ttgtattact gtttatgtaa    4320
gcagacagtt ttattgttca tgatgatata ttttatctt gtgcaatgta acatcagaga     4380
ttttgagaca caacgtggat catccagaca tgataagata cattgatgag tttggacaaa    4440
ccacaactag aatgcagtga aaaaatgct tatttgtga aatttgtgat gctattgctt      4500
tatttgtaac cattataagc tgcaataaac aagttaacaa caacaattgc attcatttta    4560 tgttcaggt tcaggggag gtgtgggagg ttttttaaag caagtaaaac ctctacaaat      4620
gtggtatggc tgattatgat cgtcgaggat ctggatccgt taaccgatat ccgcgaattc    4680
ggcgcgccgg gcctcacga cgtgttgatg aacatctgga cgatgtgcac gaacgactgc    4740
aggaactcct tgatgttctt ctcctccagc tcctcgcact ccttgcagcc cgactccgtg    4800
acgttcccgt tcgacgacag cgagttgttc gccaggatga tcaggttctc caccgtgtcg    4860
tggatcgacg cgtcccccga ctcgagcgag atgacttgga gctccaggag gaagcacttc    4920
atcgccgtga ccttgcacga cggggtggacg tccgactccg tgtacagcgt cgcgtcgatg    4980
tgcatcgact ggatgaggtc ctcgatcttc ttcaggtccg agatcacgtt cacccagttc    5040
```

```
gcctccgtct tcggcagccc cgccgagaag cagcccagga tgaagacgtg tataccggcc    5100
tccgtgagga agtgcgagtt caggagcagg cacaggtagc actggatcga tatcgaccgc    5160
aggtgcggct tcgagatccg catttcttgt cgacactcga cagatccaaa cgctcctccg    5220
acgtccccag gcagaatggc ggttccctaa acgagcattg cttatataga cctcccatta    5280
ggcacgccta ccgcccattt acgtcaatgg aacgcccatt tgcgtcattg cccctcccca    5340
ttgacgtcaa tggggatgta cttggcagcc atcgcgggcc atttaccgcc attgacgtca    5400
atgggagtac tgccaatgta ccctggcgta cttccaatag taatgtactt gccaagttac    5460
tattaataga tattgatgta ctgccaagtg ggcatttac cgtcattgac gtcaataggg     5520
ggcgtgagaa cggatatgaa tggcaatga gccatcccat tgacgtcaat ggtgggtggt     5580
cctattgacg tcaatgggca ttgagccagg cgggccattt accgtaattg acgtcaatgg    5640
gggaggcgcc atatacgtca ataggaccgc ccatatgacg tcaataggaa agaccatgag    5700
gcccttttcgt ctcgcgcgtt tcggtgatga cggtgaaaac ctctgacaca tgcagctccc    5760
ggagacggtc acagcttgtc tgtaagcgga tgccgggagc agacaagccc gtcagggcgc    5820
gtcagcgggt gttggcgggt gtcggggctg gcttaactat gcggcatcag agcagattgt    5880
actgagagtg caccatatgc ggtgtgaaat accgcacaga tgcgtaagga gaaataccg     5940
catcagattg gctattgg                                                  5958

<210> SEQ ID NO 14
<211> LENGTH: 5918
<212> TYPE: DNA
<213> ORGANISM: Artificial Sequence
<220> FEATURE:
<223> OTHER INFORMATION: synthetic dual expression plasmid vector human
      IL15Ra+IL15tPA6

<400> SEQUENCE: 14
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
acggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga dacgccatcc acgctgtttt gacctccata    720
gaagacaccg ggaccgatcc agcctccgcg gccgcgcgtc gaggaattcg ctagcaagaa    780
atggccccga gcgggcgcg aggctgccgg accctcggtc tccggcgct gctactgctc     840
ctgctgctcc ggccgccggc gacgcgggc atcacgtgcc cgccccccat gtccgtggag    900
cacgcagaca tctgggtcaa gagctacagc ttgtactccc gggagcgta catctgcaac    960
tcgggtttca gcggaaggc cggcacgtcc agctgacgg agtgcgtgtt gaacaaggcc    1020
acgaatgtcg cccactggac gacccctcg ctcaagtgca tccgcgaccc ggccctggtt    1080
```

```
caccagcggc ccgcgccacc ctccaccgta acgacggcgg gggtgacccc gcagccggag    1140
agcctctccc cgtcgggaaa ggagcccgcc gcgtcgtcgc ccagctcgaa caacacggcg    1200
gccacaactg cagcgatcgt cccgggctcc cagctgatgc cgtcgaagtc gccgtccacg    1260
ggaaccacgg agatcagcag tcatgagtcc tcccacggca cccctcgca aacgacggcc     1320
aagaactggg aactcacggc gtccgcctcc caccagccgc cggggtgta tccgcaaggc     1380
cacagcgaca ccacggtggc gatctccacg tccacggtcc tgctgtgtgg gctgagcgcg    1440
gtgtcgctcc tggcgtgcta cctcaagtcg aggcagactc ccccgctggc cagcgttgag    1500
atggaggcca tggaggctct gccggtgacg tggggaccca gcagcaggga tgaggacttg    1560
gagaactgct cgcaccacct ataatgagaa ttcacgcgtg gatctgatat cggatctgct    1620
gtgccttcta gttgccagcc atctgttgtt tgcccctccc ccgtgccttc cttgaccctg    1680
gaaggtgcca ctcccactgt cctttcctaa taaaatgagg aaattgcatc gcattgtctg    1740
agtaggtgtc attctattct gggggtggg gtggggcagg acagcaaggg ggaggattgg     1800
gaagacaata gcaggcatgc tggggatgcg gtgggctcta tgggtaccca ggtgctgaag    1860
aattgacccg gttcctcctg ggccagaaag aagcaggcac atccccttct ctgtgacaca    1920
ccctgtccac gcccctggtt cttagttcca gccccactca taggacactc atagctcagg    1980
agggctccgc cttcaatccc acccgctaaa gtacttggag cggtctctcc ctccctcatc    2040
agcccaccaa accaaaccta gcctccaaga gtgggaagaa attaaagcaa gataggctat    2100
taagtgcaga gggagagaaa atgcctccaa catgtgagga agtaatgaga gaaatcatag    2160
aatttcttcc gcttcctcgc tcactgactc gctgcgctcg tcgttcggc tgcggcgagc     2220
ggtatcagct cactcaaagg cggtaatacg gttatccaca gaatcagggg ataacgcagg    2280
aaagaacatg tgagcaaaag gccagcaaaa ggccaggaac cgtaaaaagg ccgcgttgct    2340
ggcgtttttc cataggctcc gcccccctga cgagcatcac aaaaatcgac gctcaagtca    2400
gaggtggcga aacccgacag gactataaag ataccaggcg tttccccctg gaagctccct    2460
cgtgcgctct cctgttccga ccctgccgct taccggatac ctgtccgcct ttctcccttc    2520
gggaagcgtg gcgctttctc aatgctcacg ctgtaggtat ctcagttcgg tgtaggtcgt    2580
tcgctccaag ctgggctgtg tgcacgaacc ccccgttcag cccgaccgct gcgccttatc    2640
cggtaactat cgtcttgagt ccaacccggt aagacacgac ttatcgccac tggcagcagc    2700
cactggtaac aggattagca gagcgaggta tgtaggcggt gctacagagt tcttgaagtg    2760
gtggcctaac tacggctaca ctagaaggac agtatttggt atctgcgctc tgctgaagcc    2820
agttaccttc ggaaaaagag ttggtagctc ttgatccggc aaacaaacca ccgctggtag    2880
cggtggtttt tttgtttgca agcagcagat tacgcgcaga aaaaaaggat ctcaagaaga    2940
tcctttgatc ttttctacgg ggtctgacgc tcagtggaac gaaaactcac gttaagggat    3000
tttggtcatg agattatcaa aaaggatctt cacctagatc cttttaaatt aaaaatgaag    3060
ttttaaatca atctaaagta tatatgagta aacttggtct gacagttacc aatgcttaat    3120
cagtgaggca cctatctcag cgatctgtct atttcgttca tccatagttg cctgactcgg    3180
ggggggggg cgctgaggtc tgcctcgtga agaaggtgtt gctgactcat accaggcctg    3240
aatcgcccca tcatccagcc agaaagtgag ggagccacgg ttgatgagag ctttgttgta    3300
ggtggaccag ttggtgattt tgaacttttg ctttgccacg gaacggtctg cgttgtcggg    3360
aagatgcgtg atctgatcct tcaactcagc aaaagttcga tttattcaac aaagccgccg    3420
tcccgtcaag tcagcgtaat gctctgccag tgttacaacc aattaaccaa ttctgattag    3480
```

```
aaaaactcat cgagcatcaa atgaaactgc aatttattca tatcaggatt atcaatacca    3540
tatttttgaa aaagccgttt ctgtaatgaa ggagaaaact caccgaggca gttccatagg    3600
atggcaagat cctggtatcg gtctgcgatt ccgactcgtc aacatcaat acaacctatt     3660 aatttcccct cgtcaaaaat aaggttatca agtgagaaat caccatgagt gacgactgaa    3720
tccggtgaga atggcaaaag cttatgcatt tctttccaga cttgttcaac aggccagcca    3780
ttacgctcgt catcaaaatc actcgcatca accaaaccgt tattcattcg tgattgcgcc    3840
tgagcgagac gaaatacgcg atcgctgtta aaaggacaat tacaaacagg aatcgaatgc    3900
aaccggcgca ggaacactgc cagcgcatca acaatatttt cacctgaatc aggatattct    3960
tctaatacct ggaatgctgt tttcccgggg atcgcagtgg tgagtaacca tgcatcatca    4020
ggagtacgga taaatgctt gatggtcgga agaggcataa attccgtcag ccagtttagt      4080
ctgaccatct catctgtaac atcattggca acgctacctt tgccatgttt cagaaacaac    4140
tctggcgcat cgggcttccc atacaatcga tagattgtcg cacctgattg cccgacatta    4200
tcgcgagccc atttataccc atataaatca gcatccatgt tggaatttaa tcgcggcctc    4260
gagcaagacg tttcccgttg aatatggctc ataacacccc ttgtattact gtttatgtaa    4320
gcagacagtt ttattgttca tgatgatata tttttatctt gtgcaatgta acatcagaga    4380
ttttgagaca caacgtggat catccagaca tgataagata cattgatgag tttggacaaa    4440
ccacaactag aatgcagtga aaaaatgct ttatttgtga aatttgtgat gctattgctt      4500
tatttgtaac cattataagc tgcaataaac aagttaacaa caacaattgc attcatttta    4560
tgtttcaggt tcaggggggag gtgtgggagg tttttaaag caagtaaaac ctctacaaat      4620
gtggtatggc tgattatgat cgtcgaggat ctggatctgg atccgttaac cgatatccgc    4680
gaattcggcg cgccgggccc tcacgacgtg ttgatgaaca tctggacgat gtgcacgaac    4740
gactgcagga actccttgat gttcttctcc tccagctcct cgcactcctt gcagcccgac    4800
tccgtgacgt tcccgttcga cgacagcgag ttgttcgcca ggatgatcag gttctccacc    4860
gtgtcgtgga tcgacgcgtc ccccgactcg agcgagatga cttggagctc caggaggaag    4920
cacttcatcg ccgtgacctt gcacgacggg tggacgtccg actccgtgta cagcgtcgcg    4980
tcgatgtgca tcgactggat gaggtcctcg atcttcttca ggtccgagat cacgttcacc    5040
cagtttctgg ctcctcttct gaatcgggca tggatttcct ggctgggcga acgaagact     5100 gctccacaca gcagcagcac acagcagagc cctctcttca ttgcatccat ttcttgtcga    5160
cagatccaaa cgctcctccg acgtccccag gcagaatggc ggttccctaa cgagcattg    5220 cttatataga cctcccatta ggcacgccta ccgcccattt acgtcaatgg aacgcccatt    5280
tgcgtcattg cccctcccca ttgacgtcaa tgggatgta cttggcagcc atcgcgggcc      5340
atttaccgcc attgacgtca atgggagtac tgccaatgta ccctggcgta cttccaatag    5400
taatgtactt gccaagttac tattaataga tattgatgta ctgccaagtg gccatttac     5460 cgtcattgac gtcaataggg ggcgtgagaa cggatatgaa tgggcaatga ccatcccat     5520 tgacgtcaat ggtgggtggt cctattacg tcaatgggca ttgagccagg cgggccatt       5580 accgtaattg acgtcaatgg gggaggcgcc atatacgtca ataggaccgc ccatatgacg    5640
tcaataggaa agaccatgag gccctttcgt ctcgcgcgtt tcggtgatga cggtgaaaac    5700
ctctgacaca tgcagctccc ggagacggtc acagcttgtc tgtaagcgga tgccgggagc    5760
agacaagccc gtcagggcgc gtcagcgggt gttggcgggt gtcgggctg gcttaactat     5820
```
gcggcatcag agcagattgt actgagagtg caccatatgc ggtgtgaaat accgcacaga    5880
tgcgtaagga gaaataccg catcagattg gctattgg    5918

<210> SEQ ID NO 15
<211> LENGTH: 5736
<212> TYPE: DNA
<213> ORGANISM: Artificial Sequence
<220> FEATURE:
<223> OTHER INFORMATION: synthetic dual expression plasmid vector human
      IL15sRa(soluble)+IL15tPA6

<400> SEQUENCE: 15
cctggccatt gcatacgttg tatccatatc ataatatgta catttatatt ggctcatgtc    60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
acggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga cgccatcc acgctgtttt gacctccata    720
gaagacaccg ggaccgatcc agcctccgcg gcgcgcgtc gaggaattcg ctagcaagaa    780
atggccccga gcgggcgcg aggctgccgg accctcggtc tcccggcgct gctactgctc    840
ctgctgctcc ggccgccggc gacgcgggc atcacgtgcc cgcccccat gtccgtggag    900 cacgcagaca tctgggtcaa gagctacagc ttgtactccc gggagcggta catctgcaac    960
tcgggtttca gcggaaggc cggcacgtcc agcctgacgg agtgcgtgtt gaacaaggcc    1020
acgaatgtcg cccactggac gacccccctcg ctcaagtgca tccgcgaccc ggccctggtt    1080
caccagcggc ccgcgccacc ctccaccgta acgacggcgg gggtgacccc gcagccggag    1140
agcctctccc cgtcgggaaa ggagcccgcc gcgtcgtcgc ccagctcgaa caacacggcg    1200
gccacaactg cagcgatcgt cccgggctcc cagctgatgc cgtcgaagtc gccgtccacg    1260
ggaaccacgg agatcagcag tcatgagtcc tcccacggca cccctcgca acgacggcc    1320 aagaactggg aactcacggc gtccgcctcc caccagccgc cggggggtgta tccgcaaggc    1380 cacagcgaca ccacgtaatg agaattcgcg gatatcggtt aacggatcca gatctgctgt    1440
gccttctagt tgccagccat ctgttgtttg ccctccccc gtgccttcct tgaccctgga    1500
aggtgccact cccactgtcc tttcctaata aaatgaggaa attgcatcgc attgtctgag    1560
taggtgtcat tctattctgg ggggtggggt ggggcaggac agcaagggg aggattggga    1620 agacaatagc aggcatgctg gggatgcggt ggctctatg ggtacccagg tgctgaagaa    1680
ttgacccggt tcctcctggg ccagaaagaa gcaggcacat ccccttctct gtgacacacc    1740
ctgtccacgc ccctggttct tagttccagc cccactcata ggacactcat agctcaggag    1800
ggctccgcct tcaatcccac ccgctaaagt acttggagcg gtctctccct ccctcatcag    1860
cccaccaaac caaacctagc ctccaagagt gggaagaaat taaagcaaga taggctatta    1920

```
agtgcagagg gagagaaaat gcctccaaca tgtgaggaag taatgagaga aatcatagaa    1980
tttcttccgc ttcctcgctc actgactcgc tgcgctcggt cgttcggctg cggcgagcgg    2040
tatcagctca ctcaaaggcg gtaatacggt tatccacaga atcaggggat aacgcaggaa    2100
agaacatgtg agcaaaaggc cagcaaaagg ccaggaaccg taaaaaggcc gcgttgctgg    2160
cgttttccca taggctccgc cccctgacg agcatcacaa aaatcgacgc tcaagtcaga    2220
ggtggcgaaa cccgacagga ctataaagat accaggcgtt tccccctgga agctccctcg    2280
tgcgctctcc tgttccgacc ctgccgctta ccggatacct gtccgccttt ctcccttcgg    2340
gaagcgtggc gctttctcaa tgctcacgct gtaggtatct cagttcggtg taggtcgttc    2400
gctccaagct gggctgtgtg cacgaacccc ccgttcagcc cgaccgctgc gccttatccg    2460
gtaactatcg tcttgagtcc aacccggtaa gacacgactt atcgccactg gcagcagcca    2520
ctggtaacag gattagcaga gcgaggtatg taggcggtgc tacagagttc ttgaagtggt    2580
ggcctaacta cggctacact agaaggacag tatttggtat ctgcgctctg ctgaagccag    2640
ttaccttcgg aaaaagagtt ggtagctctt gatccggcaa acaaaccacc gctggtagcg    2700
gtggtttttt tgtttgcaag cagcagatta cgcgcagaaa aaaggatctc aagaagatc     2760
ctttgatctt ttctacgggg tctgacgctc agtggaacga aaactcacgt taagggattt    2820
tggtcatgag attatcaaaa aggatcttca cctagatcct tttaaattaa aaatgaagtt    2880
ttaaatcaat ctaagtata tatgagtaaa cttggtctga cagttaccaa tgcttaatca     2940
gtgaggcacc tatctcagcg atctgtctat ttcgttcatc catagttgcc tgactcgggg    3000
gggggggcg ctgaggtctg cctcgtgaag aaggtgttgc tgactcatac caggcctgaa     3060
tcgccccatc atccagccag aaagtgaggg agccacggtt gatgagagct tgttgtagg     3120
tggaccagtt ggtgattttg aacttttgct ttgccacgga acgtctgcg ttgtcgggaa     3180
gatgcgtgat ctgatccttc aactcagcaa aagttcgatt tattcaacaa agccgccgtc    3240
ccgtcaagtc agcgtaatgc tctgccagtg ttacaaccaa ttaaccaatt ctgattagaa    3300
aaactcatcg agcatcaaat gaaactgcaa tttattcata tcaggattat caataccata    3360
tttttgaaaa agccgtttct gtaatgaagg agaaaactca ccgaggcagt tccataggat    3420
ggcaagatcc tggtatcggt ctgcgattcc gactcgtcca acatcaatac aacctattaa    3480
tttcccctcg tcaaaaataa ggttatcaag tgagaaatca ccatgagtga cgactgaatc    3540
cggtgagaat ggcaaaagct tatgcatttc tttccagact tgttcaacag gccagccatt    3600
acgctcgtca tcaaaatcac tcgcatcaac caaaccgtta ttcattcgtg attgcgcctg    3660
agcgagacga aatacgcgat cgctgttaaa aggacaatta caaacaggaa tcgaatgcaa    3720
ccggcgcagg aacactgcca gcgcatcaac aatattttca cctgaatcag gatattcttc    3780
taatacctgg aatgctgttt tcccggggat cgcagtggtg agtaaccatg catcatcagg    3840
agtacggata aaatgcttga tggtcggaag aggcataaat tccgtcagcc agtttagtct    3900
gaccatctca tctgtaacat cattggcaac gctacctttg ccatgtttca gaaacaactc    3960
tggcgcatcg ggcttcccat acaatcgata gattgtcgca cctgattgcc cgacattatc    4020
gcgagcccat ttatacccat ataaatcagc atccatgttg gaatttaatc gcggcctcga    4080
gcaagacgtt tcccgttgaa tatggctcat aacaccccctt gtattactgt ttatgtaagc    4140
agacagtttt attgttcatg atgatatatt tttatcttgt gcaatgtaac atcagagatt    4200
ttgagacaca acgtggatca tccagacatg ataagataca ttgatgagtt tggacaaacc    4260
acaactagaa tgcagtgaaa aaaatgcttt atttgtgaaa tttgtgatgc tattgcttta    4320
```

| | |
|---|---:|
| tttgtaacca ttataagctg caataaacaa gttaacaaca acaattgcat tcattttatg | 4380 |
| tttcaggttc aggggaggt gtgggaggtt ttttaaagca agtaaaacct ctacaaatgt | 4440 |
| ggtatggctg attatgatcg tcgaggatct ggatctggat ccgttaaccg atatccgcga | 4500 |
| attcggcgcg ccgggccctc acgacgtgtt gatgaacatc tggacgatgt gcacgaacga | 4560 |
| ctgcaggaac tccttgatgt tcttctcctc cagctcctcg cactccttgc agcccgactc | 4620 |
| cgtgacgttc ccgttcgacg acagcgagtt gttcgccagg atgatcaggt tctccaccgt | 4680 |
| gtcgtggatc gacgcgtccc ccgactcgag cgagatgact tggagctcca ggaggaagca | 4740 |
| cttcatcgcc gtgaccttgc acgacgggtg gacgtccgac tccgtgtaca gcgtcgcgtc | 4800 |
| gatgtgcatc gactggatga ggtcctcgat cttcttcagg tccgagatca cgttcaccca | 4860 |
| gtttctggct cctcttctga atcgggcatg gatttcctgg ctgggcgaaa cgaagactgc | 4920 |
| tccacacagc agcagcacac agcagagccc tctcttcatt gcatccattt cttgtcgaca | 4980 |
| gatccaaacg ctcctccgac gtccccaggc agaatggcgg ttccctaaac gagcattgct | 5040 |
| tatatagacc tcccattagg cacgcctacc gcccatttac gtcaatggaa cgcccatttg | 5100 |
| cgtcattgcc cctccccatt gacgtcaatg ggatgtact tggcagccat cgcgggccat | 5160 |
| ttaccgccat tgacgtcaat gggagtactg ccaatgtacc ctggcgtact ccaatagta | 5220 |
| atgtacttgc aagttacta ttaatagata ttgatgtact gccaagtggg ccatttaccg | 5280 |
| tcattgacgt caatagggg cgtgagaacg atatgaatg gcaatgagc catcccattg | 5340 |
| acgtcaatgg tgggtggtcc tattgacgtc aatgggcatt gagccaggcg gccatttac | 5400 |
| cgtaattgac gtcaatgggg gaggcgccat atacgtcaat aggaccgccc atatgacgtc | 5460 |
| aataggaaag accatgaggc cctttcgtct cgcgcgtttc ggtgatgacg gtgaaaacct | 5520 |
| ctgacacatg cagctcccgg agacggtcac agcttgtctg taagcggatg ccgggagcag | 5580 |
| acaagcccgt cagggcgcgt cagcgggtgt tggcgggtgt cggggctggc ttaactatgc | 5640 |
| ggcatcagag cagattgtac tgagagtgca ccatatgcgg tgtgaaatac cgcacagatg | 5700 |
| cgtaaggaga aaataccgca tcagattggc tattgg | 5736 |

<210> SEQ ID NO 16
<211> LENGTH: 6369
<212> TYPE: DNA
<213> ORGANISM: Artificial Sequence
<220> FEATURE:
<223> OTHER INFORMATION: synthetic sIL-15Ralpha-Fc fusion protein
      plasmid vector DPhuIL15sRa205FC+huGMIL15

<400> SEQUENCE: 16

| | |
|---|---:|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |

```
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg ggcgcgcgtc gacgctagca agaaatggcc    780
ccgaggcggg cgcgaggctg ccggaccctc ggtctcccgg cgctgctact gctcctgctg    840
ctccggccgc cggcgacgcg gggcatcacg tgcccgcccc catgtccgt ggagcacgca     900 gacatctggg tcaagagcta cagcttgtac tcccgggagc ggtacatctg caactcgggt    960
ttcaagcgga aggccggcac gtccagcctg acggagtgcg tgttgaacaa ggccacgaat   1020
gtcgcccact ggacgacccc ctcgctcaag tgcatccgcg acccggccct ggttcaccag   1080
cggcccgcgc caccctccac cgtaacgacg gcgggggtga ccccgcagcc ggagagcctc   1140
tccccgtcgg gaaaggagcc cgccgcgtcg tcgcccagct cgaacaacac ggcggccaca   1200
actgcagcga tcgtcccggg ctcccagctg atgccgtcga agtcgccgtc cacgggaacc   1260
acggagatca gcagtcatga gtcctcccac ggcaccccct cgcaaacgac ggccaagaac   1320
tgggaactca cggcgtccgc ctcccaccag ccgccggggg tgtatccgca aggccacagc   1380
gacaccacgc cgaagtcctg cgacaagacg cacacgtgcc ctccctgccc ggcgcccgag   1440
ctgctgggag gtccgagcgt gttcctcttc ccgcccaagc cgaaggacac gctcatgatc   1500
tcgcggactc ccgaggtcac ctgcgtcgtg gtagacgtca gccacgagga cccggaggtc   1560
aagttcaact ggtacgttga cggcgtagag gtgcacaacg cgaagacgaa gccgcgggag   1620
gagcagtaca actcgacgta ccgagtcgtg tcggtcctga ccgtcctgca ccaggactgg   1680
ctcaacggga aggagtacaa gtgcaaggtg tcgaacaagg cgctccctgc cccgatcgag   1740
aagacgatct cgaaggcgaa gggccagccc agggagcccc aggtctacac gctcccgcca   1800
tcgcgggaca gctgacgaa gaaccaggtt ccctgacgt gcctcgtcaa gggcttctac    1860
ccatcggaca tcgcggtgga gtgggagagc aacgggcagc cggagaacaa ctacaagacc   1920
acgcctccgg tgctcgactc ggacgggtcg ttcttcctct actcgaagct gaccgtcgac   1980
aagagccggt ggcagcaggg caacgtgttc tcctgctcgg tgatgcacga ggccctccac   2040
aaccactaca cccagaagtc gctcagtctg agcccgggga gtaatgagg atccgaattc    2100 gcggatatcg gttaacggat ccagatctgc tgtgccttct agttgccagc catctgttgt   2160
ttgcccctcc cccgtgcctt ccttgaccct ggaaggtgcc actcccactg tcctttccta   2220
ataaaatgag gaaattgcat cgcattgtct gagtaggtgt cattctattc tggggggtgg   2280
ggtggggcag gacagcaagg gggaggattg ggaagacaat agcaggcatg ctggggatgc   2340
ggtgggctct atgggtaccc aggtgctgaa gaattgaccc ggttcctcct gggccagaaa   2400
gaagcaggca catccccttc tctgtgacac accctgtcca cgcccctggt tcttagttcc   2460
agccccactc ataggacact catagctcag gagggctccg ccttcaatcc cacccgctaa   2520
agtacttgga gcggtctctc cctccctcat cagcccacca aaccaaacct agcctccaag   2580
agtgggaaga aattaaagca agataggcta ttaagtgcag agggagagaa aatgcctcca   2640
acatgtgagg aagtaatgag agaaatcata gaatttcttc cgcttcctcg ctcactgact   2700
cgctgcgctc ggtcgttcgg ctgcggcgag cggtatcagc tcactcaaag gcggtaatac   2760
ggttatccac agaatcaggg gataacgcag gaaagaacat gtgagcaaaa ggccagcaaa   2820
aggccaggaa ccgtaaaaag gccgcgttgc tggcgttttt ccataggctc cgcccccctg   2880
acgagcatca caaaaatcga cgctcaagtc agaggtggcg aaacccgaca ggactataaa   2940
gataccaggc gtttccccct ggaagctccc tcgtgcgctc tcctgttccg accctgccgc   3000
```

```
ttaccggata cctgtccgcc tttctcccft cgggaagcgt ggcgctttct catagctcac    3060
gctgtaggta tctcagttcg gtgtaggtcg ttcgctccaa gctgggctgt gtgcacgaac    3120
cccccgttca gcccgaccgc tgcgccttat ccggtaacta tcgtcttgag tccaacccgg    3180
taagacacga cttatcgcca ctggcagcag ccactggtaa caggattagc agagcgaggt    3240
atgtaggcgg tgctacagag ttcttgaagt ggtggcctaa ctacggctac actagaagaa    3300
cagtatttgg tatctgcgct ctgctgaagc cagttacctt cggaaaaaga gttggtagct    3360
cttgatccgg caaacaaacc accgctggta gcggtggttt ttttgtttgc aagcagcaga    3420
ttacgcgcag aaaaaaagga tctcaagaag atcctttgat cttttctacg ggtctgacg    3480 ctcagtggaa cgaaaactca cgttaaggga ttttggtcat gagattatca aaaggatct    3540 tcacctagat ccttttaaat taaaaatgaa gttttaaatc aatctaaagt atatatgagt    3600
aaacttggtc tgacagttac caatgcttaa tcagtgaggc acctatctca gcgatctgtc    3660
tatttcgttc atccatagtt gcctgactcg ggggggggg gcgctgaggt ctgcctcgtg    3720
aagaaggtgt tgctgactca taccaggcct gaatcgcccc atcatccagc cagaaagtga    3780
gggagccacg gttgatgaga gctttgttgt aggtggacca gttggtgatt ttgaactttt    3840
gctttgccac ggaacggtct gcgttgtcgg aagatgcgt gatctgatcc ttcaactcag    3900
caaaagttcg atttattcaa caaagccgcc gtcccgtcaa gtcagcgtaa tgctctgcca    3960
gtgttacaac caattaacca attctgatta gaaaaactca tcgagcatca aatgaaactg    4020
caatttattc atatcaggat tatcaatacc atattttga aaaagccgtt tctgtaatga    4080
aggagaaaac tcaccgaggc agttccatag gatggcaaga tcctggtatc ggtctgcgat    4140
tccgactcgt ccaacatcaa tacaacctat taatttcccc tcgtcaaaaa taaggttatc    4200
aagtgagaaa tcaccatgag tgacgactga atccggtgag aatggcaaaa gcttatgcat    4260
ttctttccag acttgttcaa caggccagcc attacgctcg tcatcaaaat cactcgcatc    4320
aaccaaaccg ttattcattc gtgattgcgc ctgagcgaga cgaaatacgc gatcgctgtt    4380
aaaaggacaa ttacaaacag gaatcgaatg caaccggcgc aggaacactg ccagcgcatc    4440
aacaatattt tcacctgaat caggatattc ttctaatacc tggaatgctg ttttcccggg    4500
gatcgcagtg gtgagtaacc atgcatcatc aggagtacgg ataaaatgct tgatggtcgg    4560
aagaggcata aattccgtca gccagtttag tctgaccatc tcatctgtaa catcattggc    4620
aacgctacct ttgccatgtt tcagaaacaa ctctggcgca tcgggcttcc catacaatcg    4680
atagattgtc gcacctgatt gcccgacatt atcgcgagcc catttatacc catataaatc    4740
agcatccatg ttggaattta atcgcggcct cgagcaagac gtttcccgtt gaatatggct    4800
cataacaccc cttgtattac tgtttatgta agcagacagt tttattgttc atgatgatat    4860
atttttatct tgtgcaatgt aacatcagag attttgagac acaacgtgga tcatccagac    4920
atgataagat acattgatga gtttggacaa accacaacta gaatgcagtg aaaaaaatgc    4980
tttatttgtg aaatttgtga tgctattgct ttatttgtaa ccattataag ctgcaataaa    5040
caagttaaca acaacaattg cattcatttt atgtttcagg ttcagggga ggtgtgggag    5100 gttttttaaa gcaagtaaaa cctctacaaa tgtggtatgg ctgattatga tcgtcgagga    5160
tctggatccg ttaaccgata tccgcgaatt cggcgcgccg ggccctcacg acgtgttgat    5220
gaacatctgg acgatgtgca cgaacgactg caggaactcc ttgatgttct tctcctccag    5280
ctcctcgcac tccttgcagc ccgactccgt gacgttcccg ttcgacgaca gcgagttgtt    5340
cgccaggatg atcaggttct ccaccgtgtc gtggatcgac gcgtccccg actcgagcga    5400
```

```
gatgacttgg agctccagga ggaagcactt catcgccgtg accttgcacg acgggtggac    5460
gtccgactcc gtgtacagcg tcgcgtcgat gtgcatcgac tggatgaggt cctcgatctt    5520
cttcaggtcc gagatcacgt tcacccagtt cgagatgctg caggccaccg tccccaggag    5580
tagcaggctc tggagccaca tttcttgtcg acagatccaa acgctcctcc gacgtcccca    5640
ggcagaatgg cggttcccta acgagcatt gcttatatag acctcccatt aggcacgcct     5700
accgcccatt tacgtcaatg aacgcccat ttgcgtcatt gcccctcccc attgacgtca     5760
atggggatgt acttggcagc catcgcgggc catttaccgc cattgacgtc aatgggagta    5820
ctgccaatgt accctggcgt acttccaata gtaatgtact tgccaagtta ctattaatag    5880
atattgatgt actgccaagt gggccattta ccgtcattga cgtcaatagg gggcgtgaga    5940
acggatatga atgggcaatg agccatccca ttgacgtcaa tggtgggtgg tcctattgac    6000
gtcaatgggc attgagccag cgggccatt taccgtaatt gacgtcaatg ggggaggcgc     6060
catatacgtc aataggaccg cccatatgac gtcaataggt aagaccatga ggccctttcg    6120
tctcgcgcgt ttcggtgatg acggtgaaaa cctctgacac atgcagctcc cggagacggt    6180
cacagcttgt ctgtaagcgg atgccgggag cagacaagcc cgtcagggcg cgtcagcggg    6240
tgttggcggg tgtcggggct ggcttaacta tgcggcatca gagcagattg tactgagagt    6300
gcaccatatg cggtgtgaaa taccgcacag atgcgtaagg agaaaatacc gcatcagatt    6360
ggctattgg                                                             6369
```

<210> SEQ ID NO 17
<211> LENGTH: 436
<212> TYPE: PRT
<213> ORGANISM: Artificial Sequence
<220> FEATURE:
<223> OTHER INFORMATION: synthetic sIL-15Ralpha-Fc fusion protein
      huIL15sRa205-Fc

<400> SEQUENCE: 17

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175
```

Gln Thr Thr Ala Lys Asn Trp Glu Leu Thr Ala Ser Ala Ser His Gln
                180                 185                 190

Pro Pro Gly Val Tyr Pro Gln Gly His Ser Asp Thr Thr Pro Lys Ser
            195                 200                 205

Cys Asp Lys Thr His Thr Cys Pro Pro Cys Pro Ala Pro Glu Leu Leu
        210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Asp Glu Leu Thr Lys Asn Gln Val
            340                 345                 350

Ser Leu Thr Cys Leu Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys
        435

<210> SEQ ID NO 18
<211> LENGTH: 131
<212> TYPE: PRT
<213> ORGANISM: Artificial Sequence
<220> FEATURE:
<223> OTHER INFORMATION: synthetic human GMCSF-IL15 fusion protein
      huGMCSF-IL15

<400> SEQUENCE: 18

Met Trp Leu Gln Ser Leu Leu Leu Leu Gly Thr Val Ala Cys Ser Ile
1               5                   10                  15

Ser Asn Trp Val Asn Val Ile Ser Asp Leu Lys Lys Ile Glu Asp Leu
            20                  25                  30

Ile Gln Ser Met His Ile Asp Ala Thr Leu Tyr Thr Glu Ser Asp Val
        35                  40                  45

His Pro Ser Cys Lys Val Thr Ala Met Lys Cys Phe Leu Leu Glu Leu
    50                  55                  60

Gln Val Ile Ser Leu Glu Ser Gly Asp Ala Ser Ile His Asp Thr Val
65                  70                  75                  80

Glu Asn Leu Ile Ile Leu Ala Asn Asn Ser Leu Ser Ser Asn Gly Asn
                85                  90                  95

```
Val Thr Glu Ser Gly Cys Lys Glu Cys Glu Leu Glu Glu Lys Asn
            100                 105                 110

Ile Lys Glu Phe Leu Gln Ser Phe Val His Ile Val Gln Met Phe Ile
        115                 120                 125

Asn Thr Ser
    130

<210> SEQ ID NO 19
<211> LENGTH: 6354
<212> TYPE: DNA
<213> ORGANISM: Artificial Sequence
<220> FEATURE:
<223> OTHER INFORMATION: synthetic IL-15Ralpha-Fc fusion protein plasmid
      vector AG256DPhuIL15sRA200FC+huGMIL15

<400> SEQUENCE: 19
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg gcggtaggc gtgtacggtg gaggtctat ataagcagag      660 ctcgtttagt gaaccgtcag atcgcctgga cgccatcc acgctgtttt gacctccata     720
gaagacaccg ggaccgatcc agcctccgcg gcgcgcgtc gacgctagca agaaatggcc      780
ccgaggcggg cgcgaggctg ccggaccctc ggtctcccgg cgctgctact gctcctgctg     840
ctccggccgc cggcgacgcg gggcatcacg tgcccgcccc ccatgtccgt ggagcacgca     900
gacatctggg tcaagagcta cagcttgtac tcccgggagc ggtacatctg caactcgggt     960
ttcaagcgga aggccggcac gtccagcctg acggagtgcg tgttgaacaa ggccacgaat    1020
gtcgcccact ggacgacccc ctcgctcaag tgcatccgcg accggccct ggttcaccag    1080 cggcccgcgc acctcccac cgtaacgacg gcggggtga ccccgcagcc ggagagcctc     1140
tccccgtcgg gaaaggagcc cgccgcgtcg tcgcccagct cgaacaacac ggcggccaca    1200
actgcagcga tcgtccccggg ctcccagctg atgccgtcga gtcgccgtc cacgggaacc    1260 acggagatca gcagtcatga gtcctcccac ggcacccct cgcaaacgac ggccaagaac    1320
tgggaactca cggcgtccgc ctcccaccag ccgccggggg tgtatccgca aggcccgaag    1380
tcctgcgaca gacgcacac gtgccctccc tgccggcgc ccgagctgct gggaggtccg     1440
agcgtgttcc tcttcccgcc caagccgaag gacacgctca tgatctcgcg gactcccgag    1500
gtcacctgcg tcgtggtaga cgtcagccac gaggacccgg aggtcaagtt caactggtac    1560
gttgacggcg tagaggtgca caacgcgaag acgaagccgc gggaggagca gtacaactcg    1620
acgtaccgag tcgtgtcggt cctgaccgtc ctgcaccagg actggctcaa cgggaaggag    1680
tacaagtgca aggtgtcgaa caaggcgctc cctgccccga tcgagaagac gatctcgaag    1740
gcgaagggcc agcccaggga gccccaggtc tacacgctcc cgccatcgcg ggacgagctg    1800
```

-continued

| | |
|---|---|
| acgaagaacc aggtttccct gacgtgcctc gtcaagggct tctacccatc ggacatcgcg | 1860 |
| gtggagtggg agagcaacgg gcagccggag aacaactaca agaccacgcc tccggtgctc | 1920 |
| gactcggacg ggtcgttctt cctctactcg aagctgaccg tcgacaagag ccggtggcag | 1980 |
| cagggcaacg tgttctcctg ctcggtgatg cacgaggccc tccacaacca ctacacccag | 2040 |
| aagtcgctca gtctgagccc ggggaagtaa tgaggatccg aattcgcgga tatcggttaa | 2100 |
| cggatccaga tctgctgtgc cttctagttg ccagccatct gttgtttgcc cctcccccgt | 2160 |
| gccttccttg accctggaag gtgccactcc cactgtcctt tcctaataaa atgaggaaat | 2220 |
| tgcatcgcat tgtctgagta ggtgtcattc tattctgggg gtgggggtgg ggcaggacag | 2280 |
| caaggggag gattgggaag acaatagcag gcatgctggg gatgcggtgg gctctatggg | 2340 |
| tacccaggtg ctgaagaatt gacccggttc ctcctgggcc agaaagaagc aggcacatcc | 2400 |
| ccttctctgt gacacaccct gtccacgccc ctggttctta gttccagccc cactcatagg | 2460 |
| acactcatag ctcaggaggg ctccgccttc aatcccaccc gctaaagtac ttggagcggt | 2520 |
| ctctccctcc ctcatcagcc caccaaacca aacctagcct ccaagagtgg gaagaaatta | 2580 |
| aagcaagata ggctattaag tgcagaggga gagaaaatgc ctccaacatg tgaggaagta | 2640 |
| atgagagaaa tcatagaatt tcttccgctt cctcgctcac tgactcgctg cgctcggtcg | 2700 |
| ttcggctgcg cgagcggta tcagctcact caaaggcggt aatacggtta tccacagaat | 2760 |
| caggggataa cgcaggaaag aacatgtgag caaaaggcca gcaaaggcc aggaaccgta | 2820 |
| aaaaggccgc gttgctggcg ttttccata ggctccgccc ccctgacgag catcacaaaa | 2880 |
| atcgacgctc aagtcagagg tggcgaaacc cgacaggact ataaagatac caggcgtttc | 2940 |
| cccctggaag ctccctcgtg cgctctcctg ttccgaccct gccgcttacc ggatacctgt | 3000 |
| ccgcctttct cccttcggga agcgtggcgc tttctcatag ctcacgctgt aggtatctca | 3060 |
| gttcggtgta ggtcgttcgc tccaagctgg gctgtgtgca cgaaccccc gttcagcccg | 3120 |
| accgctgcgc cttatccggt aactatcgtc ttgagtccaa cccggtaaga cacgacttat | 3180 |
| cgccactggc agcagccact ggtaacagga ttagcagagc gaggtatgta ggcggtgcta | 3240 |
| cagagttctt gaagtggtgg cctaactacg gctacactag aagaacagta tttggtatct | 3300 |
| gcgctctgct gaagccagtt accttcggaa aaagagttgg tagctcttga tccggcaaac | 3360 |
| aaaccaccgc tggtagcggt ggtttttttg tttgcaagca gcagattacg cgcagaaaaa | 3420 |
| aaggatctca agaagatcct ttgatctttt ctacggggtc tgacgctcag tggaacgaaa | 3480 |
| actcacgtta agggattttg gtcatgagat tatcaaaaag gatcttcacc tagatccttt | 3540 |
| taaattaaaa atgaagtttt aaatcaatct aaagtatata tgagtaaact tggtctgaca | 3600 |
| gttaccaatg cttaatcagt gaggcaccta tctcagcgat ctgtctattt cgttcatcca | 3660 |
| tagttgcctg actcgggggg gggggcgct gaggtctgcc tcgtgaagaa ggtgttgctg | 3720 |
| actcatacca ggcctgaatc gccccatcat ccagccagaa agtgagggag ccacggttga | 3780 |
| tgagagcttt gttgtaggtg gaccagttgg tgattttgaa cttttgcttt gccacggaac | 3840 |
| ggtctgcgtt gtcgggaaga tgcgtgatct gatccttcaa ctcagcaaaa gttcgattta | 3900 |
| ttcaacaaag ccgccgtccc gtcaagtcag cgtaatgctc tgccagtgtt acaaccaatt | 3960 |
| aaccaattct gattagaaaa actcatcgag catcaaatga aactgcaatt tattcatatc | 4020 |
| aggattatca ataccatatt tttgaaaaag ccgtttctgt aatgaaggag aaaactcacc | 4080 |
| gaggcagttc cataggatgg caagatcctg gtatcggtct gcgattccga ctcgtccaac | 4140 |
| atcaatacaa cctattaatt tcccctcgtc aaaaataagg ttatcaagtg agaaatcacc | 4200 |

| | |
|---|---|
| atgagtgacg actgaatccg gtgagaatgg caaaagctta tgcatttctt ccagacttg | 4260 |
| ttcaacaggc cagccattac gctcgtcatc aaaatcactc gcatcaacca aaccgttatt | 4320 |
| cattcgtgat tgcgcctgag cgagacgaaa tacgcgatcg ctgttaaaag acaattaca | 4380 |
| aacaggaatc gaatgcaacc ggcgcaggaa cactgccagc gcatcaacaa tattttcacc | 4440 |
| tgaatcagga tattcttcta atacctggaa tgctgttttc ccggggatcg cagtggtgag | 4500 |
| taaccatgca tcatcaggag tacgataaaa atgcttgatg gtcggaagag gcataaattc | 4560 |
| cgtcagccag tttagtctga ccatctcatc tgtaacatca ttggcaacgc tacctttgcc | 4620 |
| atgtttcaga acaactctg gcgcatcggg cttcccatac aatcgataga ttgtcgcacc | 4680 |
| tgattgcccg acattatcgc gagcccattt atacccatat aaatcagcat ccatgttgga | 4740 |
| atttaatcgc ggcctcgagc aagacgtttc ccgttgaata tggctcataa cacccccttgt | 4800 |
| attactgttt atgtaagcag acagttttat tgttcatgat gatatatttt tatcttgtgc | 4860 |
| aatgtaacat cagagatttt gagacacaac gtggatcatc cagacatgat aagatacatt | 4920 |
| gatgagtttg gacaaaccac aactagaatg cagtgaaaaa aatgctttat ttgtgaaatt | 4980 |
| tgtgatgcta ttgctttatt tgtaaccatt ataagctgca ataaacaagt taacaacaac | 5040 |
| aattgcattc attttatgtt tcaggttcag ggggaggtgt gggaggtttt ttaaagcaag | 5100 |
| taaaacctct acaaatgtgg tatggctgat tatgatcgtc gaggatctgg atccgttaac | 5160 |
| cgatatccgc gaattcggcg cgccgggccc tcacgacgtg ttgatgaaca tctgacgat | 5220 |
| gtgcacgaac gactgcagga actccttgat gttcttctcc tccagctcct cgcactcctt | 5280 |
| gcagcccgac tccgtgacgt tcccgttcga cgacagcgag ttgttcgcca ggatgatcag | 5340 |
| gttctccacc gtgtcgtgga tcgacgcgtc ccccgactcg agcgagatga cttggagctc | 5400 |
| caggaggaag cacttcatcg ccgtgacctt gcacgacggg tggacgtccg actccgtgta | 5460 |
| cagcgtcgcg tcgatgtgca tcgactggat gaggtcctcg atcttcttca ggtccgagat | 5520 |
| cacgttcacc cagttcgaga tgctgcaggc caccgtcccc aggagtagca ggctctggag | 5580 |
| ccacatttct tgtcgacaga tccaaacgct cctccgacgt ccccaggcag aatggcggtt | 5640 |
| ccctaaacga gcattgctta tagacctcc ccattaggca cgcctaccgc ccatttacgt | 5700 |
| caatggaacg cccatttgcg tcattgcccc tccccattga cgtcaatggg gatgtacttg | 5760 |
| gcagccatcg cgggccattt accgccattg acgtcaatgg gagtactgcc aatgtaccct | 5820 |
| ggcgtacttc caatagtaat gtacttgcca agttactatt aatagatatt gatgtactgc | 5880 |
| caagtgggcc atttaccgtc attgacgtca ataggggcg tgagaacgga tatgaatggg | 5940 |
| caatgagcca tcccattgac gtcaatggtg ggtggtccta ttgacgtcaa tgggcattga | 6000 |
| gccaggcggg ccatttaccg taattgacgt caatggggga ggcgccatat acgtcaatag | 6060 |
| gaccgcccat atgacgtcaa taggtaagac catgaggccc tttcgtctcg cgcgtttcgg | 6120 |
| tgatgacggt gaaaacctct gacacatgca gctcccggag acgtcacag cttgtctgta | 6180 |
| agcggatgcc gggagcagac aagcccgtca gggcgcgtca gcgggtgttg gcgggtgtcg | 6240 |
| gggctggctt aactatgcgg catcagagca gattgtactg agagtgcacc atatgcggtg | 6300 |
| tgaaataccg cacagatgcg taaggagaaa ataccgcatc agattggcta ttgg | 6354 |

<210> SEQ ID NO 20
<211> LENGTH: 431
<212> TYPE: PRT
<213> ORGANISM: Artificial Sequence
<220> FEATURE:
<223> OTHER INFORMATION: synthetic sIL-15Ralpha-Fc fusion protein huIL15sRa200-Fc

<400> SEQUENCE: 20

| | | | | | | | | | | | | | | |
|---|---|---|---|---|---|---|---|---|---|---|---|---|---|---|
| Met | Ala | Pro | Arg | Arg | Ala | Arg | Gly | Cys | Arg | Thr | Leu | Gly | Leu | Pro | Ala |
| 1 | | | | 5 | | | | | 10 | | | | | 15 | |
| Leu | Leu | Leu | Leu | Leu | Leu | Leu | Arg | Pro | Ala | Thr | Arg | Gly | Ile | Thr |
| | | | 20 | | | | | 25 | | | | | 30 | |
| Cys | Pro | Pro | Met | Ser | Val | Glu | His | Ala | Asp | Ile | Trp | Val | Lys | Ser |
| | | 35 | | | | 40 | | | | | 45 | | | |
| Tyr | Ser | Leu | Tyr | Ser | Arg | Glu | Arg | Tyr | Ile | Cys | Asn | Ser | Gly | Phe | Lys |
| | 50 | | | | | 55 | | | | | 60 | | | | |
| Arg | Lys | Ala | Gly | Thr | Ser | Ser | Leu | Thr | Glu | Cys | Val | Leu | Asn | Lys | Ala |
| 65 | | | | | 70 | | | | | 75 | | | | | 80 |
| Thr | Asn | Val | Ala | His | Trp | Thr | Thr | Pro | Ser | Leu | Lys | Cys | Ile | Arg | Asp |
| | | | | 85 | | | | | 90 | | | | | 95 | |
| Pro | Ala | Leu | Val | His | Gln | Arg | Pro | Ala | Pro | Pro | Ser | Thr | Val | Thr | Thr |
| | | | | 100 | | | | | 105 | | | | | 110 | |
| Ala | Gly | Val | Thr | Pro | Gln | Pro | Glu | Ser | Leu | Ser | Pro | Ser | Gly | Lys | Glu |
| | | | 115 | | | | | 120 | | | | | 125 | | |
| Pro | Ala | Ala | Ser | Ser | Pro | Ser | Ser | Asn | Asn | Thr | Ala | Ala | Thr | Thr | Ala |
| | 130 | | | | | 135 | | | | | 140 | | | | |
| Ala | Ile | Val | Pro | Gly | Ser | Gln | Leu | Met | Pro | Ser | Lys | Ser | Pro | Ser | Thr |
| 145 | | | | | 150 | | | | | 155 | | | | | 160 |
| Gly | Thr | Thr | Glu | Ile | Ser | Ser | His | Glu | Ser | Ser | His | Gly | Thr | Pro | Ser |
| | | | | 165 | | | | | 170 | | | | | 175 | |
| Gln | Thr | Thr | Ala | Lys | Asn | Trp | Glu | Leu | Thr | Ala | Ser | Ala | Ser | His | Gln |
| | | | | 180 | | | | | 185 | | | | | 190 | |
| Pro | Pro | Gly | Val | Tyr | Pro | Gln | Gly | Pro | Lys | Ser | Cys | Asp | Lys | Thr | His |
| | | | 195 | | | | | 200 | | | | | 205 | | |
| Thr | Cys | Pro | Pro | Cys | Pro | Ala | Pro | Glu | Leu | Leu | Gly | Gly | Pro | Ser | Val |
| | 210 | | | | | 215 | | | | | 220 | | | | |
| Phe | Leu | Phe | Pro | Pro | Lys | Pro | Lys | Asp | Thr | Leu | Met | Ile | Ser | Arg | Thr |
| 225 | | | | | 230 | | | | | 235 | | | | | 240 |
| Pro | Glu | Val | Thr | Cys | Val | Val | Val | Asp | Val | Ser | His | Glu | Asp | Pro | Glu |
| | | | | 245 | | | | | 250 | | | | | 255 | |
| Val | Lys | Phe | Asn | Trp | Tyr | Val | Asp | Gly | Val | Glu | Val | His | Asn | Ala | Lys |
| | | | | 260 | | | | | 265 | | | | | 270 | |
| Thr | Lys | Pro | Arg | Glu | Glu | Gln | Tyr | Asn | Ser | Thr | Tyr | Arg | Val | Val | Ser |
| | | | | 275 | | | | | 280 | | | | | 285 | |
| Val | Leu | Thr | Val | Leu | His | Gln | Asp | Trp | Leu | Asn | Gly | Lys | Glu | Tyr | Lys |
| | | | 290 | | | | | 295 | | | | | 300 | | |
| Cys | Lys | Val | Ser | Asn | Lys | Ala | Leu | Pro | Ala | Pro | Ile | Glu | Lys | Thr | Ile |
| 305 | | | | | 310 | | | | | 315 | | | | | 320 |
| Ser | Lys | Ala | Lys | Gly | Gln | Pro | Arg | Glu | Pro | Gln | Val | Tyr | Thr | Leu | Pro |
| | | | | 325 | | | | | 330 | | | | | 335 | |
| Pro | Ser | Arg | Asp | Glu | Leu | Thr | Lys | Asn | Gln | Val | Ser | Leu | Thr | Cys | Leu |
| | | | 340 | | | | | 345 | | | | | 350 | | |
| Val | Lys | Gly | Phe | Tyr | Pro | Ser | Asp | Ile | Ala | Val | Glu | Trp | Glu | Ser | Asn |
| | | | 355 | | | | | 360 | | | | | 365 | | |
| Gly | Gln | Pro | Glu | Asn | Asn | Tyr | Lys | Thr | Thr | Pro | Pro | Val | Leu | Asp | Ser |
| | 370 | | | | | 375 | | | | | 380 | | | | |

-continued

```
Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
            420                 425                 430
```